United States Patent
Croteau et al.

(10) Patent No.: US 6,451,576 B1
(45) Date of Patent: Sep. 17, 2002

(54) SESQUITERPENE SYNTHASES FROM GRAND FIR (ABIES GRANDIS), AND METHODS OF USE

(75) Inventors: Rodney Bruce Croteau, Pullman, WA (US); Jörg Bohlmann, Jena (DE); John E. Crock, Moscow, ID (US); Christopher L. Steele, Admore, OK (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/865,171

(22) Filed: May 24, 2001

Related U.S. Application Data

(62) Division of application No. 09/234,393, filed on Jan. 20, 1999, now Pat. No. 6,265,639.
(60) Provisional application No. 60/072,204, filed on Jan. 22, 1998.

(51) Int. Cl.[7] .............................. C12N 9/88; C07H 21/04
(52) U.S. Cl. ....................................... 435/232; 536/23.2
(58) Field of Search ................................ 435/232, 440; 536/23.2

(56) References Cited

PUBLICATIONS

Salin, F., et al., "Purification and Characterization of Trans–β–farnesene Synthase from Maritime Pine (*Pinus pinaster* Ait.) Needles", *J. Plant Physiol.*, vol, 146, pp. 203–209, 1995.

(List continued on next page.)

*Primary Examiner*—Ponnathapu Achutamurthy
*Assistant Examiner*—Yong Pak
(74) *Attorney, Agent, or Firm*—Christensen O'Connor Johnson Kindness PLLC

(57) ABSTRACT cDNAs encoding, E-α-bisabolene synthase, δ-selinene synthase and γ-humulene synthase from Grand Fir (*Abies grandis*) have been isolated and sequenced, and the corresponding amino acid sequences have been determined. Accordingly, isolated DNA sequences (SEQ ID No:12; SEQ ID No:19 and SEQ ID No:23) are provided which code for the expression of E-α-bisabolene synthase (SEQ ID No:13), δ-selinene synthase (SEQ ID No:20) and γ-humulene synthase (SEQ ID No:24), respectively, from Grand Fir (*Abies grandis*). In other aspects, replicable recombinant cloning vehicles are provided which code for E-α-bisabolene synthase, δ-selinene synthase and γ-humulene synthase, or for a base sequence sufficiently complementary to at least a portion of E-α-bisabolene synthase, δ-selinene synthase or γ-humulene synthase DNA or RNA to enable hybridization therewith. In yet other aspects, modified host cells are provided that have been transformed, transfected, infected and/or injected with a recombinant cloning vehicle and/or DNA sequence encoding E-α-bisabolene synthase, δ-selinene synthase or ,γ-humulene synthase. Thus, systems and methods are provided for the recombinant expression of the aforementioned recombinant sesquiterpene syntheses that may be used to facilitate their production, isolation and purification in significant amounts. Recombinant E-α-bisabolene synthase, δ-selinene synthase and γ-humulene synthase may be used to obtain expression or enhanced expression of E-α-bisabolene synthase, δ-selinene synthase and γ-humulene synthase in plants in order to enhance the production of sesquiterpenoids, or may be otherwise employed for the regulation or expression of E-α-bisabolene synthase, δ-selinene synthase and γ-humulene synthase, or the production of their products.

1 Claim, 4 Drawing Sheets

OTHER PUBLICATIONS

Dehal, S.S. & Croteau, R., "Partial Purification and Characterization of Two Sesquiterpene Cyclases from Sage (Saliva officinalis) Which Catalyze the Respective Conversion of Farnesyl Pyrophosphate to Humulene and Caryophyllene", *Arch. Biochem. Biophys.*, vol. 261, No. 2, pp. 346–356, 1988.

Munck, S.L. & Croteau, R., "Purification and Characterization of the Sesquiterpene Cyclase Patchoulol Synthase from *Pogostemon cablin*", *Arch. Biochem. Biophys.*, vol. 282, No. 1, pp. 58–64, Oct. 1990.

Belingheri, L., et al., "Partial Purification and Properties of the Sesquiterpene β–Selinene Cyclase from *Citrofortunella mitis* fruits", *Plant Sci.*, vol. 84, pp. 129–136, 1992.

Facchini, P. J. & Chappell J., "Gene Family for an Elicitor–Induced Sesquiterpene Cyclase in Tobacco", *Proc. Natl. Acad. Sci. USA*, vol. 89, pp. 11088–11092, Nov. 1992.

Back, K. & Chappell, J., "Cloning and Bacterial Expression of a Sesquiterpene Cyclase from *Hyoscyamus muticus* and Its Molecular Comparison to Related Terpene Cyclases", *J. Biol. Chem.*, vol. 270, No. 13, pp. 7375–7381, Mar. 31, 1995.

Chen, X.-Y., et al., "Cloning, Expression, and Characterization of (+)-δ-Cadinene Synthase: A Catalyst for Cotton Phytoalexin Biosynthesis", *Arch. Biochem. Biophys.*, vol. 324, No. 2, pp. 255–266, Dec. 20, 1995.

Lewinsohn, E., et al., "Simultaneous Analysis of Monoterpenes and Diterpenoids of Conifer Oleoresin", *Phytochem. Anal.*, vol. 4, pp. 220–225, 1993.

Smedman, L.A., et al., "Oxygenated Monoterpenoids and Sesquiterpenoid Hydrocarbons of the Cortical Turpentine From Different Abies Species", *Phytochemistry*, vol. 8, pp. 1471–1479, 1969.

Funk, C., et al., Regulation of Oleoresinosis in Grand Fir (Abies grandis), *Plant Physiol.*, vol. 106, pp. 999–1005, 1994.

Gijzen, M., et al., Characterization of the Constitutive and Wound–Inducible Monoterpene Cyclases of Grand Fir (Abies grandis), *Arch. Biochem. Biophys.*, vol. 289, No. 2, pp. 267–273, Sep. 1991.

Colby, S. M., et al., 4S–Limonene Synthase from the Oil Glands of Spearmint (Mentha spicata) *J. Biol. Chem.*, vol. 268, No. 31, pp. 23016–23024, Nov. 5, 1993.

Mau, C. J. D., and West, C. A., "Cloning of Casbene Synthase cDNA: Evidence for Conserved Structural Features among Terpenoid Cyclases in Plants", *Proc. Natl. Acad. Sci. USA*, vol. 91, pp. 8497–8501, Aug. 1994.

Steele, C. L., et al., "Induced Oleoresin Biosynthesis in Grand Fir as a Defense Against Bark Beetles", *Proc. Natl. Acad. Sci. USA*, vol. 92, pp. 4164–4168, May 1995.

Chen, X.-Y., et al., Cloning and Heterologous Expression of a Second (+)-δ-Cadinene Synthase from *Gossypium arboreum*, *J. Nat. Prod.*, vol. 59, pp. 944–951, 1996.

Wildung, M.R. & Croteau, R., "A cDNA Clone for Taxadiene Synthase, the Diterpene Cyclase That Catalyzes the Committed Step of Taxol Biosynthesis", *J. Biol. Chem.*, vol. 271, No. 16, pp. 9201–9204, Apr. 19, 1996.

Sun. T. & Kamiya, Y., "The Arabidopsis GA1 Locus Encodes the Cyclase ent–Kaurene Synthetase A of Gibberellin Biosynthesis", *Plant Cell*, vol. 6, pp. 1509–1518, Oct. 1994.

Bensen, R.J., "Cloning and Characterization of the Maize An1 Gene", *Plant Cell*, vol. 7, pp. 75–84, Jan. 1995.

Dudareva, N., et al., "Evolution of Floral Scent in Clarkia: Novel Patterns of S–Linalool Synthase Gene Expression in the C. breweri Flower", *Plant Cell*, vol. 8, pp. 1137–1148, Jul. 1996.

Yamaguchi, S., et al., Molecular Cloning and Characterization of a cDNA Encoding the Gibberellin Biosynthetic Enzyme ent–kaurene Synthase B from Pumpkin (*Cucurbita maxima* L.), *Plant Journal*, vol. 10, No. 2, pp. 203–210, 1996.

Yuba, A., et al., "cDNA Cloning, Characterization, and Functional Expression of 4S–(–)–Limonene Synthase from *Perilla frutescens*", *Arch. Biochem. Biophys.*, vol. 332, No. 21, pp. 280–287, Aug. 15, 1996.

Vogel, B.S., et al., "Abietadiene Synthase from Grand Fir (Abies grandis)", *J. Biol. Chem.* vol. 271, No. 38, pp. 23262–23268, Sep. 20, 1996.

Lewinsohn, E., et al., "Simple Isolation of Functional RNA from Woody Stems of Gymnosperms", *Plant Mol. Biol. Rep.*, vol. 12, No. 1, pp. 20–25, Mar. 1994.

Bohlmann, J., et al., "Monoterpene Synthases from Grand Fir (Abies grandis)", *J. Biol. Chem.*, vol. 272, No. 35, pp. 21784–21792, Aug. 29, 1997.

DeBlock, M., "The cell biology of plant transformation: Current state problems, prospects and the implications for the plant breeding," *Euphytica*, vol. 72, pp. 1–14 1993.

Back, K. et al., "Expression of a Plant Sesquiterpene Cyclase Gene in *Escherichia coli*," *Arch. Biochem. Biophys.*, vol. 315, No. 2, pp. 527–532, 1994.

Davis, E.M., "Purification of (+)-δ-Cadinene Synthase, A Sesquiterpene Cyclase from Bacteria–Inoculated Cotton Foliar Tissue," *Phytochemistry*, vol. 41, No. 4, pp. 1047–1055, 1996.

E-α-bisabolene

R = H   Todomatuic Acid

R = CH3   Juvabione

Juvenile Hormone III

α-Cubebene
(4.6%)

α-Copaene
(7.9%)

β-Caryophyllene
(8.7%)

α-Muurolene
(13.1%)

δ-Cadinene
(7.75%)

*E,E*-Germacrene B
(19.1%)

SESQUITERPENE SYNTHASES FROM GRAND FIR (ABIES GRANDIS), AND METHODS OF USE

RELATED APPLICATIONS

This application is a divisional of prior application Ser. No. 09/234,393, filed Jan. 20, 1999 now U.S. Pat. No. 6,265,639, priority from the filing date of which is hereby claimed under 35 U.S.C. §120, and further claims the benefit of provisional application No. 60/072,204, filed Jan. 22, 1998, the benefit of which is hereby claimed under 35 U.S.C. §119. The entire disclosure of the prior applications, from which priority is claimed, is considered as being part of the disclosure of this application and is hereby incorporated by reference herein.

GOVERNMENT RIGHTS

This invention was supported in part by grant numbers NIH GM-31354, USDA NRI 97-35302-4432 and Hatch Project 10A-3037-0268. The United States government has certain rights in the invention.

FIELD OF THE INVENTION

The present invention relates to nucleic acid sequences which code for sesquiterpene synthases (cyclases) from Grand Fir (Abies grandis), and to vectors containing the sequences, host cells containing the sequences and methods of producing recombinant sesquiterpene synthases and their mutants.

BACKGROUND OF THE INVENTION

Conifer oleoresin is a mixture of turpentine and rosin that functions in insect defense and in wound sealing (Johnson, M. & Croteau, R. (1987) in *Ecology and Metabolism of Plant Lipids* (Fuller, G. & Nes, W. D., eds) pp 76–91, ACS Symposium Series 325, American Chemical Society, Washington, D.C.; Gijzen, M., et al., (1993) in *Bioactive Volatile Compounds from Plants* (Teranishi, R., et al., eds) pp 8–22, ACS Symposium Series 525, American Chemical Society, Washington, D.C.). Turpentine is composed of monoterpene ($C_{10}$) and sesquiterpene ($C_{15}$) olefins, while rosin is composed of diterpene ($C_{20}$) resin acids (FIG. 1). The volatile turpentine fraction of conifer oteoresin, which may consist of up to 30 different monoterpenes (Lewinsohn, E., et al., (1993) *Phytochem. Anal.* 4, 220–225) and an even larger number of sesquiterpenes (See Example 1, herein) furnishes a solvent for the diterpene resin acids which, upon stem wounding, harden to form a mechanical barrier thereby sealing the wound site (Johnson, M. A. & Croteau, R. (1987) in *Ecology and Metabolism of Plant Lipids* eds. Fuller, G. & Nes, W. D. (Am. Chem. Soc., Washington, D.C.), ACS Symp. Series 325, pp. 67–91).

Grand fir (Abies grandis) has been developed as a model system for the study of both constitutive and wound-induced oleoresin formation (oleoresinosis). The composition of the monoterpene olefin and the diterpene resin acid fractions of grand fir oleoresin has been defined (Lewinsohn, E., et al., (1993) *Phytochem. Anal.* 4, 220–225), and the induced biosynthesis of these natural products upon stem wounding has been described in detail (Gijzen, M., et al., (1993) in *Bioactive Volatile Compounds from Plants* (Teranishi, R., et al., eds) pp 8–22, ACS Symposium Series 525, American Chemical Society, Washington, D.C.; Lewinsohn, E., et al., (1992) in *Regulation of Isopentenoid Metabolism* (Nes, W. D., et al., eds) pp 8–17, ACS Symposium Series 497, American Chemical Society, Washington, D.C.; Gijzen, M., et al., (1992) *Arch. Biochem. Biophys.* 294, 670–674; Funk, C., et al., (1994) *Plant Physiol.* 106, 999–1005). The time-course of induction, after wounding, of the monoterpene synthases involved in turpentine formation has been analyzed by immunoblotting techniques and the process of induced oleoresinosis was thus shown to involve de novo synthesis of these enzymes (Gijzen, M., et al., (1992) *Arch. Biochem. Biophys.* 294, 670–674). The cDNA sequence of abietadiene synthase, a diterpene cyclase from grand fir that is involved in resin acid biosynthesis (LaFever, R. E., et al., (1994) *Arch. Biochem. Biophys.* 313, 139–149)) has been reported (Stofer Vogel, B., et al., (1996) *J. Biol. Chem.* 271, 23262–23268), and several cDNA clones encoding monoterpene synthases from this conifer species have recently become available (Bohlmann, J., et al., (1997) *J. Biol. Chem.* 272, 21784–21792).

In comparison with the monoterpenes and diterpenes of conifer oleoresin, the sesquiterpenes of conifer turpentine have received relatively little experimental attention because they constitute less than 10% of the oleoresin. The relatively low concentrations of sesquiterpenes in conifer oleoresin may, however, belie their biological significance. Sesquiterpenoid phytoalexins, i.e., antibiotic compounds, are well known in angiosperm species (Threlfall, D. R. & Whitehead, I. M. (1991) in *Ecological Chemistry and Biochemistry of Plant Terpenoids* (Harborne, J B. & Tomas-Barberan, F. A., eds) pp 159–208, Clarendon Press, Oxford, UK), suggesting that the sesquiterpenes of conifer oleoresin may play a similar role in antibiosis.

A conifer oleoresin sesquiterpene that has been relatively well-characterized is juvabione. Juvabione is the methylester of todomatuic acid, an oxygenated derivative of the sesquiterpene olefin bisabolene (FIG. 2). The conifer sesquiterpene juvabione resembles insect juvenile hormones and, thus, can disrupt insect development and reproduction at metamorphosis and diapause (Bowers, W. S., et al., (1976) *Science* 193, 542–547; Bowers, W. S. (1991) in *Herbivores: Their Interaction with Secondary Plant Metabolites*, Vol. I, G. A. Rosenthal and M. R. Berenbaum, eds. (Acad. Press, San Diego), pp. 431–456). Juvabione is sometimes referred to as "paper factor" because its presence in paper made from trees of the genus Abies inhibits maturation of insect larvae reared in contact with the paper (Slama, K. & Williams, C. M. (1965) *Proc. Natl. Acad. Sci. USA* 54, 411–414; Slama, K. & Williams, C. M. (1966) *Nature* 210, 329–330; Bowers, W. S., et al., (1966) *Science* 154, 1020–1021). Accumulation of todomatuic acid, the precursor of juvabione, in grand fir after insect feeding suggests that biosynthesis of the juvenile hormone analogue is induced de novo in response to insect attack (Puritch, G. S. & Nijholt, W. W. (1974) *Can. J. Bot.* 52, 585–587).

Only a single sesquiterpene synthase, E-β-farnesene synthase, from a gymnosperm source, maritime pine (Pinus pinaster), has been reported (Salin, F., et al., (1995) *J. Plant Physiol.* 146, 203–209). In contrast, several sesquiterpene synthases from angiosperms have been described (Dehal, S. S. & Croteau, R. (1988) *Arch. Biochem. Biophys.* 261, 346–356; Munck, S. L. & Croteau, R. (1990) *Arch. Biochem. Biophys.* 282, 58–64; Belingheri, L., et al., (1992) *Plant Sci.* 84, 129–136), and a number of genes encoding sesquiterpene synthases involved in phytoalexin biosynthesis in angiosperms have been isolated (Facchini, P. J. & Chappell, J. (1992) *Proc. Natl. Acad. Sci. USA* 89, 11088–11092; Back, K. & Chappell, J. (1995) *J. Biol. Chem.* 270, 7375–7381; Chen, X.-Y., et al., (1995) *Arch. Biochem. Biophys.* 324, 255–266).

SUMMARY OF THE INVENTION

In accordance with the foregoing, the present invention relates to isolated nucleic acids that encode gymnosperm sesquiterpene synthases, to isolated, recombinant gymnosperm sesquiterpene synthases, to replicable, recombinant expression vectors that include a nucleic acid sequence that encodes a gymnosperm sesquiterpene synthase, to cells that have been transformed, transfected or otherwise manipulated to include one or more nucleic acids of the present invention, and to methods for imparting or enhancing the production of a gymnosperm sesquiterpene synthase in a host cell including the step of introducing into the host cell an expression vector of the present invention under conditions enabling expression of the sesquiterpene synthase protein in the host cell. Representative cDNAs encoding the gymnosperm sesquiterpene synthases E-α-bisabolene synthase, δ-selinene synthase and γ-humulene synthase have been isolated from Grand Fir (*Abies grandis*) and sequenced, and the corresponding amino acid sequences have been deduced. Accordingly, in preferred embodiments, the present invention relates to isolated DNA sequences which code for the expression of E-α-bisabolene synthase, such as the sequence designated SEQ ID No:12 which encodes E-α-bisabolene synthase (SEQ ID No:13) from Grand Fir (*Abies grandis*), for the expression of δ-selinene synthase, such as the sequence designated SEQ ID No:19, which encodes δ-selinene synthase (SEQ ID No:20) from Grand Fir (*Abies grandis*), and for the expression of γ-humulene synthase, such as the sequence designated SEQ ID No:23, which encodes the γ-humulene synthase (SEQ ID No:24) from Grand Fir (*Abies grandis*).

In other aspects, the present invention is directed to replicable recombinant cloning vehicles comprising a nucleic acid sequence which codes for a E-α-bisabolene synthase, δ-selinene synthase or γ-humulene synthase. The present invention is also directed to a base sequence sufficiently complementary to at least a portion of a nucleic acid encoding a E-α-bisabolene synthase, δ-selinene synthase or γ-humulene synthase, to enable hybridization therewith. The aforesaid complementary base sequences include, but are not limited to: antisense RNA complementary to all or part of a nucleic acid sequence encoding a E-α-bisabolene synthase, δ-selinene synthase or γ-humulene synthase; fragments of DNA that are complementary to part of a nucleic acid sequence encoding an E-α-bisabolene synthase, δ-selinene synthase or γ-humulene synthase, and which are therefore useful as polymerase chain reaction primers, or as probes for genes encoding E-α-bisabolene synthase, δ-selinene synthase or γ-humulene synthase, or related genes.

In yet other aspects of the invention, modified host cells are provided that have been transformed, transfected, infected and/or injected with a recombinant cloning vehicle and/or DNA sequence of the invention. Thus, the present invention provides for the recombinant expression of gymnosperm E-α-bisabolene synthase, δ-selinene synthase and γ-humulene synthase, preferably Grand fir (*Abies grandis*) E-α-bisabolene synthase, δ-selinene synthase and γ-humulene synthase, and the inventive concepts may be used to facilitate the production, isolation and purification of significant quantities of recombinant E-α-bisabolene synthase, δ-selinene synthase and γ-humulene synthase (or of their primary enzyme products) for subsequent use, to obtain expression or enhanced expression of E-α-bisabolene synthase, δ-selinene synthase or γ-humulene synthase in plants, microorganisms or animals, or may be otherwise employed in an environment where the regulation or expression of E-α-bisabolene synthase, δ-selinene synthase or γ-humulene synthase is desired for the production of these synthases, or their enzyme products, or derivatives thereof.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
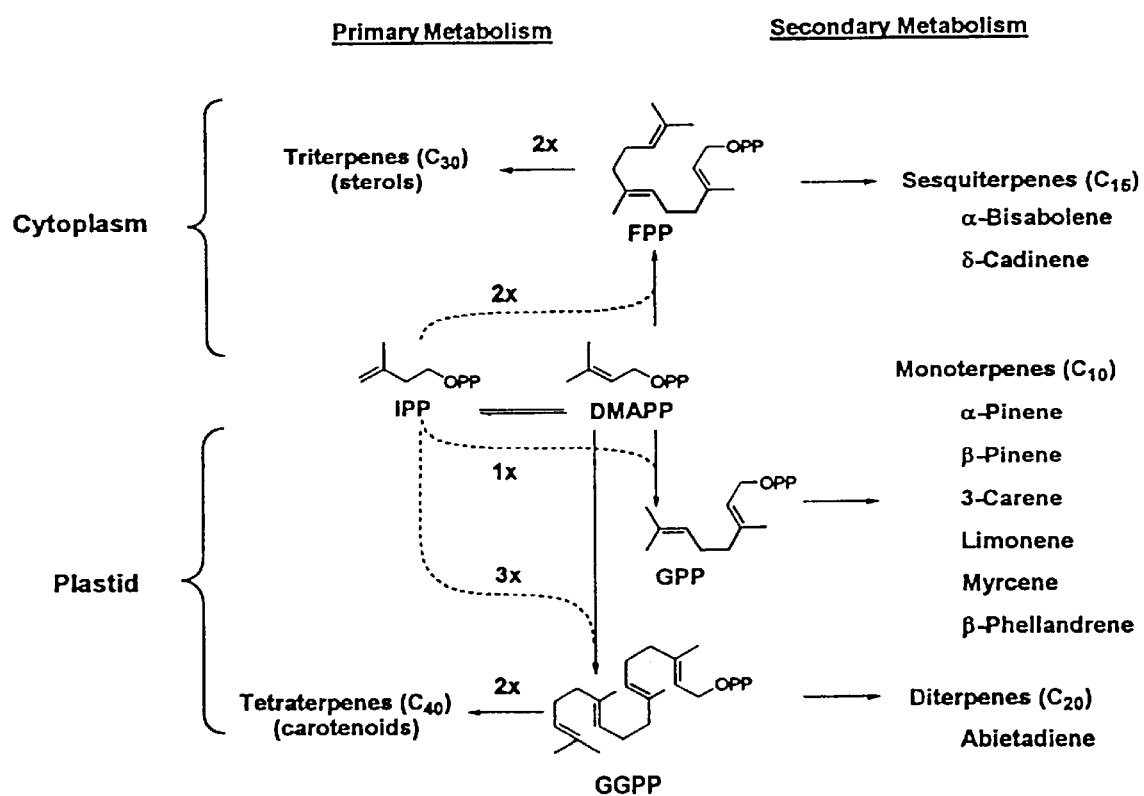
FIG. 1 shows the biosynthesis of monoterpenes, sesquiterpenes and diterpenes and their relationship to primary metabolism. The abbreviations used are: IPP, isopentenyl diphosphate; DMAPP, dimethylallyl diphosphate; GPP, geranyl diphosphate; FPP, farnesyl diphosphate; GGPP, geranylgeranyl diphosphate.

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|-----|---|---------------|-----|---|------------|
| Thr | T | threonine     | Leu | L | leucine    |
| Ser | S | serine        | Tyr | Y | tyrosine   |
| Glu | E | glutamic acid | Phe | F | phenylalanine |
| Pro | P | proline       | His | H | histidine  |
| Gly | G | glycine       | Lys | K | lysine     |
| Ala | A | alanine       | Arg | R | arginine   |
| Cys | C | cysteine      | Trp | W | tryptophan |
| Val | V | valine        | Gln | Q | glutamine  |
| Met | M | methionine    | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" (%I) means the percentage of amino acids or nucleotides that occupy the same relative position when two amino acid sequences, or two nucleic acid sequences, are aligned side by side.

The term "percent similarity" (%S) is a statistical measure of the degree o[0086]relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (Henikoff, S. and Henikoff, J. G., *Proc. Nat'l Acad Sci USA* 89: 10915–10919, 1992).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "E-α-bisabolene synthase" is used herein to mean an enzyme capable of generating multiple sesquiterpenes from farnesyl diphosphate. The principal and characteristic sesquiterpene synthesized by E-α-bisabolene synthase is E-α-bisabolene, which comprises at least 90% of the sesquiterpene mixture synthesized by E-α-bisabolene synthase from farnesyl diphosphate.

The term "δ-selinene synthase" is used herein to mean an enzyme capable of generating multiple sesquiterpenes from farnesyl diphosphate. The principal and characteristic sesquiterpene synthesized by δ-selinene synthase is δ-selinene, which comprises at least 20% of the sesquiterpene mixture synthesized by δ-selinene synthase from farnesyl diphosphate.

The term "γ-humulene synthase" is used herein to mean an enzyme capable of generating multiple sesquiterpenes from farnesyl diphosphate. The principal and characteristic sesquiterpene synthesized by γ-humulene synthase is γ-humulene, which comprises at least 20% of the sesquiterpene mixture synthesized by γ-humulene synthase from farnesyl diphosphate.

The terms "alteration", "amino acid sequence alteration", "variant" and "amino acid sequence variant" refer to E-α-bisabolene synthase, δ-selinene synthase or γ-humulene synthase molecules with some differences in their amino acid sequences as compared to native E-α-bisabolene synthase, δ-selinene synthase or γ-humulene synthase molecules. Ordinarily, the variants will possess at least about 70% homology with native E-α-bisabolene synthase, δ-selinene synthase or γ-humulene synthase, and preferably they will be at least about 80% homologous with native E-α-bisabolene synthase, δ-selinene synthase or γ-humulene synthase. The amino acid sequence variants of E-α-bisabolene synthase, δ-selinene synthase or γ-humulene synthase falling within this invention possess substitutions, deletions, and/or insertions at certain positions. Sequence variants of E-α-bisabolene synthase, δ-selinene synthase or γ-humulene synthase may be used to attain desired enhanced or reduced enzymatic activity, modified regiochemistry or stereochemistry, or altered substrate utilization or product distribution.

Substitutional E-α-bisabolene synthase, δ-selinene synthase or γ-humulene synthase variants are those that have at least one amino acid residue in the native E-α-bisabolene synthase, δ-selinene synthase or γ-humulene synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the E-α-bisabolene synthase, δ-selinene synthase or γ-humulene synthase molecules may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the E-α-bisabolene synthase, δ-selinene synthase or γ-humulene synthase molecules would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional E-α-bisabolene synthase, δ-selinene synthase or γ-humulene synthase variants are those with one or more amino acids inserted immediately adjacent to an amino acid at a particular position in the native E-α-bisabolene synthase, δ-selinene synthase or γ-humulene synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native E-α-bisabolene synthase, δ-selinene synthase or γ-humulene synthase molecule have been removed. Ordinarily, deletional variants will have one or two amino acids deleted in a particular region of the E-α-bisabotene synthase, δ-selinene synthase or γ-humulene synthase molecule.

The terms "biological activity", "biologically active", "activity" and "active" refer to the ability of E-α-bisabolene synthase, δ-selinene synthase and γ-humulene synthase molecules to convert farnesyl diphosphate to a group of sesquiterpenes, of which E-α-bisabolene is the principal and characteristic sesquiterpene synthesized by E-α-bisabolene synthase, δ-selinene is the principal and characteristic sesquiterpene synthesized by δ-selinene synthase and γ-humulene is the principal and characteristic sesquiterpene synthesized by γ-humulene synthase, as measured in an enzyme activity assay, such as the assay described in Example 2 below. Amino acid sequence variants of E-α-bisabolene synthase, δ-selinene synthase and γ-humulene synthase may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. -The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA encoding a fill-length, wound-inducible E-α-bisabolene synthase was cloned by 5'-RACE. A partial-length, wound-inducible, putative sesquiterpene synthase cDNA, designated AG1.28 (SEQ ID No:1), had previously been isolated from a wounded Grand Fir cDNA library by utilizing PCR primers C (SEQ ID No:2) and D (SEQ ID NO:3) to amplify a 110 bp cDNA fragment, designated probe 1 (SEQ ID NO:4). Probe 1 (SEQ ID No:4) was, in turn, used to screen the Grand Fir cDNA library and identify CDNA AG1.28 (SEQ ID No:1). In order to obtain the missing 5'-sequence of clone AG1.28 (SEQ ID No:1), a 5'-RACE reaction was performed utilizing adaptor-ligated cDNA isolated from wounded Grand Fir stems. The sequence of the adaptor oligonucleotide is set forth in (SEQ ID No:5). The 5'-RACE reaction utilized primer AP1 (SEQ ID No:6) and reverse RACE primer RJ1 (SEQ ID No:7).

An internal 404 bp cDNA fragment, designated RJ8 (SEQ ID No:8), of the resulting PCR product was amplified using primers RJ1(SEQ ID No:7) and RJ2 (SEQ ID No:9). Primer RJ2 (SEQ ID No:9) incorporated a BamHI restriction site for subcloning of RJ8 (SEQ ID No:8) into the pBluescript SK(+)-derived plasmid pAG1.28 containing cDNA AG1.28 (SEQ ID No:1).

A HincII site at nucleotide position 2382 of the cDNA insert in pAG1.28 (SEQ ID No:1), 32 nucleotides downstream of the stop codon of the 2350 bps open reading frame, was eliminated by site directed mutagenesis using mutagenesis primer F (SEQ ID No:10) and primer R (SEQ ID No:11). cDNA fragment RJ8 (SEQ ID No:8) was digested with BamHI and HincII and ligated into BamHI/HincII-digested pAG1.28, resulting in plasmid pAG1. The nucleotide sequence of the full-length E-α-bisabolene synthase cDNA insert of plasmid pAG1 is set forth in (SEQ ID No: 12). For functional expression, the 2528 bp BamHI/XhoI cDNA insert of pAG1 (SEQ ID No:12) was subcloned into BamHI/XhoI-digested pGEX-4T-2 resulting in plasmid pGAG1.

A cDNA encoding a full-length δ-selinene synthase was cloned by 5'-RACE. A partial-length, putative sesquiterpene synthase cDNA, designated ag4.30 (SEQ ID No:14), had previously been isolated from a wounded Grand Fir cDNA library by utilizing PCR primers C (SEQ ID No:2) and D (SEQ ID NO:3) to amplify a 110 bp cDNA fragment, designated probe 4 (SEQ ID NO:15). Probe 4 (SEQ ID No: 15) was, in turn, used to screen the Grand Fir cDNA library and identify cDNA ag4.30 (SEQ ID No:14). Since ag4.30 (SEQ ID No:14) did not encode a starting methionine, 5'-RACE was carried out to generate a cDNA fragment containing the missing 5'-end of ag4.30 (SEQ ID No:14). The 5'-RACE reaction utilized polyA$^+$ mRNA isolated from wounded Grand Fir saplings and a reverse RACE primer specific for ag4.30 (SEQ ID No:17).

A 5'-specific primer (SEQ ID No:17), and a 3'-specific primer (SEQ ID No:18), were designed based on the sequences of ag4.30 (SEQ ID No:14) and the 5'-RACE product containing the missing 5'-end of ag4.30. The ag4.30-specific 5' primer (SEQ ID No:17) -incorporated a BamHI restriction endonuclease site immediately upstream of the starting methionine codon. The 3'-specific primer (SEQ ID No-18) was designed to encompass the stop codon, and included a XhoI site to facilitate ligation into the pGEX-4T-1 expression vector. The resulting PCR product AG4 (SEQ ID No:19) encoded a full-length δ-selinene synthase protein (SEQ ID No:20) and was sequentially cloned first into pbluescript (SK-), then into a pGEX vector designated as pGAG4. For further subcloning of the amplified, full-length cDNA (SEQ ID No:19) into the pSBETa vector for high-level expression, the pGAG4 insert was amplified by PCR using primer combinations 4-NdeI (SEQ ID No:21) and 4-BamHI (SEQ ID No:22). The PCR product was digested with BamHI and NdeI and then ligated into NdeI/BamHI-digested pSBETa to yield expression plasmid pSBAG4.

A γ-humulene synthase cDNA, AG5, (SEQ ID No:23) was cloned in the same way as the δ-selinene synthase cDNA (SEQ ID No:19) except that PCR primers C (SEQ ID No:2) and D (SEQ ID No:3) were used to amplify a 110 bp cDNA fragment designated probe 5 (SEQ ID NO:25). Probe 5 (SEQ ID No:25) was used to screen the Grand Fir cDNA library and identify a cDNA molecule designated ag5.9 (SEQ ID No:26). Since ag5.9 (SEQ ID No: 26) did not encode a starting methionine, 5'-RACE was carried out using polyA$^+$ mRNA isolated from wounded Grand Fir saplings. The 5'-RACE reaction utilized a reverse RACE primer specific for ag5.9 (SEQ ID No:27).

A 5'-specific primer (SEQ ID No:28) and a 3'-specific primer (SEQ ID No:29) were designed based on the sequences of ag5.9 and the 5'-RACE product containing the missing 5'-end of ag5.9. The ag5.9-specific 5' primer (SEQ ID No:28) incorporated a BamHI restriction endonuclease site immediately upstream of the starting methionine codon. The 3'-specific primer (SEQ ID No:29) was designed to encompass the stop codon, and included an EcoRI site to facilitate ligation into the pGEX-4T-1 expression vector. The resulting PCR product encoded a fill-length γ-humulene synthase cDNA, AG5, (SEQ ID No:23) and was sequentially cloned first into pBluescript (SK-), then into a pGEX vector designated as pGAG5. For further subcloning of the amplified, full-length cDNA into the pSBETa vector for high-level expression, the pGAG5 insert was amplified by PCR using primer combinations 5-NdeI (SEQ ID No:30) and 5-BamHI (SEQ ID No:31). The PCR product was digested with BamHI and NdeI and then ligated into NdeI/BamHI-digested pSBETa to yield expression plasmid pSBAG5.

Unlike the protein sequences of monoterpene synthases, the deduced amino acid sequences of the cloned sesquiterpene syntlhases, i.e., E-α-bisabolene synthase (SEQ ID No:13), δ-selinene synthase (SEQ ID No:20) and γ-humulene synthase (SEQ ID No:24), each lack an N-terminal, plastidial targeting sequence. The absence of a plastidial targeting sequence in each of the cloned proteins is consistent with the fact that all sesquiterpene synthases are cytosolic enzymes. Addition of an N-terminal targeting sequence selected from transport sequences well known in the art (see, e.g., von Heijne G et al., *Eur. J. Biochem* 180: 535–545, 1989; Stryer, *Biochemistry* W. H. Freeman and Company, New York, N.Y., p. 769 [1988]) may be employed to direct the cloned sesquiterpene synthases of the present invention to other intracellular or extracellular locations.

In addition to the amino acid sequences of native E-α-bisabolene synthase (SEQ ID No:13), native δ-selinene synthase (SEQ ID No:20) and native γ-humulene synthase (SEQ ID No:24), encoded by the cDNA sequences set forth in SEQ ID Nos:12, 19 and 23, respectively, sequence variants produced by deletions, substitutions, mutations and/or insertions are intended to be within the scope of the invention except insofar as limited by the prior art. E-α-bisabolene synthase, δ-selinene synthase or γ-humulene synthase amino acid sequence variants may be constructed by mutating the DNA sequence that encodes wild-type E-α-bisabolene synthase, δ-selinene synthase or γ-humulene synthase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform *E. coli*, such as strain *E. coli* BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product distribution can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate E-α-bisabolene synthase, δ-selinene synthase or γ-humulene synthase deletion variants, as described in section 15.3 of Sambrook et al. (*Molecular Cloning: A Laboratory Manual*, 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the E-α-bisabolene synthase, δ-selinene synthase or γ-humulene synthase molecule. An optimal oligonucleotide will have 12 to 15 perfectly matched nucleotides on either side of the nucleotides coding for the mutation. To mutagenize the wild-type E-α-bisabolene synthase, δ-selinene synthase or γ-humulene synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type E-α-bisabolene synthase, δ-selinene synthase or γ-humulene synthase inserted in the vector, and the second strand of DNA encodes the mutated form of E-α-bisabolene synthase, δ-selinene synthase or γ-humulene synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type E-α-bisabolene synthase, δ-selinene synthase or γ-humulene synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Eukaryotic expression systems may be utilized for E-α-bisabolene synthase, δ-selinene synthase or γ-humulene synthase production since they are capable of carrying out any required posttranslational modifications, and of directing a modified E-α-bisabolene synthase, δ-selinene synthase or γ-humulene synthase, bearing an N-terminal targeting. sequence, to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Biotechnology* 6:47–55 [1987]) for expression of the E-α-bisabolene synthase, δ-selinene synthase or γ-humulene synthase of the invention. Infection of insect cells (such as cells of the species *Spodoptera frugiperda*) with the recombinant baculoviruses allows for the production of large amounts of the E-α-bisabolene synthase, δ-selinene synthase or γ-humulene synthase protein. In addition, the baculovirus system has other important advantages for the production of recombinant E-α-bisabolene synthase, δ-selinene synthase or γ-humulene synthase. For example, baculoviruses do not infect humans and can therefore be safely handled in large quantities. In the baculovirus system, a DNA construct is prepared including a DNA segment encoding E-α-bisabolene synthase, δ-selinene synthase or γ-humulene synthase and a vector. The vector may comprise the polyhedron gene promoter region of a baculovirus, the baculovirus flanking sequences necessary for proper crossover during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent to (or operably linked or "downstream" or "under the control of") to the polyhedron gene promoter and (ii) the promoter/E-α-bisabolene synthase, δ-selinene synthase or γ-humulene synthase combination is flanked on both sides by 200–300 base pairs of baculovirus DNA (the flanking sequences).

To produce the E-α-bisabolene synthase, δ-selinene synthase or γ-humulene synthase DNA construct, a cDNA clone encoding the full length E-α-bisabolene synthase, δ-selinene synthase or γ-humulene synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full E-α-bisabolene synthase, δ-selinene synthase or γ-humulene synthase. For example, an insect host cell can be cotransfected or transfected separately with the DNA construct and a functional baculovirus. Resulting recombinant baculoviruses can then be isolated and used to infect cells to effect production of the E-α-bisabolene synthase, δ-selinene synthase or γ-humulene synthase. Host insect cells include, for example, *Spodoptera frugiperda* cells, that are capable of producing a baculovirus-expressed E-α-bisabolene synthase, δ-selinene synthase or γ-humulene synthase. Insect host cells infected with a recombinant baculovirus of the present invention are then cultured under conditions allowing expression of the baculovirus-encoded E-α-bisabolene synthase, δ-selinene synthase or γ-humulene synthase. E-α-bisabolene synthase, δ-selinene synthase or γ-humulene synthase thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Succharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]. Additional yeast transformation protocols are set forth in Gietz et al., *N.A.R.* 20(17):1425, 1992; Reeves et al., FEMS 99:193–197, 1992.

Suitable promoting sequences in yeast vectors include the promoters for 3-phosphoglycerate kinase (Hitzeman et al.,*J.*

*Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode E-α-bisabolene synthase, δ-selinene synthase or γ-humulene synthase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Additionally, animal transformation strategies are reviewed in Monastersky G. M. and Robl, J. M., *Strategies in Transgenic Animal Science*, ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating E-α-bisabolene synthase, δ-selinene synthase or γ-humulene synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a E-α-bisabolene synthase, δ-selinene synthase or γ-humulene synthase gene that previously has had its native promoter removed. This engineered gene is the combination of a promoter that responds to an external chemical stimulus and a gene responsible for successful production of E-α-bisabolene synthase, δ-selinene synthase or γ-humulene synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993]). Representative examples include electroporation-facilitated DNA uptake by protoplasts (Rhodes et al., *Science* 240(4849):204–207 [1988]); treatment of protoplasts with polyethylene glycol (Lyznik et al., *Plant Molecular Biology* 13:151–161 [1989]); and bombardment of cells with DNA laden microprojectiles (Klein et al., *Plant Physiol.* 91:440–444 [1989] and Boynton et al., *Science* 240(4858):1534–1538 [1988]). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide gluiosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23;243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273.113 [1978]). Smaller or larger SV40 DNA fragments may also be used, provided they contain the approximately 250-bp sequence extending from the HindIII site toward the BgII site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of E-α-bisabolene synthase, δ-selinene synthase or γ-humulene synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM539, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enxymol.*, 204:63, 1991.

As a representative example, cDNA sequences encoding E-α-bisabolene synthase, δ-selinene synthase or γ-humulene synthase may be transferred to the $(His)_6$·Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the E-α-bisabolene synthase, δ-selinene synthase or γ-humulene synthase again purified by immobilized metal ion affinity chromatography, this time using a shallower imidazole gradient to elute the recombinant synthase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUC118, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm, such as the sesquiterpene synthases of the present invention, can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

The sesquiterpene synthases of the present invention lack an N-terminal targeting sequence. Nonetheless, N-terminal targeting sequences from plants, animals and microbes can be employed in the practice of the invention to direct the sesquiterpene synthases to the endoplasmic reticulum, mitochondria or other cellular compartments, or to target the protein for export to the medium. These considerations apply to the overexpression of E-α-bisabolene synthase, δ-selinene synthase or γ-humulene synthase, and to direction of expression within cells or intact organisms to permit gene product function in any desired location.

The construction of suitable vectors containing DNA encoding replication sequences, regulatory sequences, phenotypic selection genes and the E-α-bisabolene synthase, δ-selinene synthase or γ-humulene synthase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, E-α-bisabolene synthase, δ-selinene synthase or γ-humulene synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The isolation of the E-α-bisabolene synthase cDNA, δ-selinene synthase cDNA and γ-humulene synthase cDNA permits the development of efficient expression systems for these functional enzymes; provides useful tools for examining the developmental regulation of sesquiterpene biosynthesis and permits the isolation of other genes encoding E-ax-bisabolene synthase, δ-selinene synthase or γ-humulene synthases. The isolation of the E-α-bisabolene synthase, δ-selinene synthase and γ-humulene synthase cDNAs also permits the transformation of a wide range of organisms.

The genes encoding E-α-bisabolene synthase, δ-selinene synthase and γ-humulene synthase may be incorporated into any organism (intact plant, animal, microbe), or cell culture derived therefrom, that produces farnesyl diphosphate to effect the conversion of this primary substrate to E-α-bisabolene, δ-selinene or γ-humulene, and their subsequent metabolic products, depending on the organism. The E-α-bisabolene synthase, δ-selinene synthase or γ-humulene synthase genes may be introduced into any organism for a variety of purposes including, but not limited to: the introduction of sesquiterpene biosynthesis de novo; the modification of endogenous sesquiterpene biosynthesis, for example, to alter the fragrance and/or flavor profile of plant material, or to produce plants which provide an abundant source of flavor and/or fragrance compounds; the improvement of defense capability by, for example, producing sesquiterpene products which act as insect repellants, feeding deterrents, oviposition deterrents, toxins, or which act as precursors to phytoalexins (antibiotics) or hormone analogs; the alteration of other ecological interactions mediated by farnesyl diphosphate and its derivatives, for example, the genetic alteration of plants to produce volatile sesquiterpenes which act as pollenator attractors, or as competitive phytotoxins.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.) "Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 (1982)), and Goeddel et al. (*Nucleic Acids Res.*, supra).

The following examples merely illustrate the various embodiments now contemplated for practicing the invention, but should not be construed to limit the invention. All literature citations herein are expressly incorporated by reference.

EXAMPLE 1

Analysis of Oleoresin Sesquiterpenes Extracted From Unwounded Grand Fir (*Abies grandis*) Saplings Oleoresin Isolation and Analysis—Grand fir sapling stems were sectioned into 2–3 mm discs and extracted overnight with pentane (3.0 ml/g tissue) at room temperature. The pentane extract was decolorized with activated charcoal, washed with water, and passed over a column of $MgSO_4$ and silica gel (Mallinckrodt, Type 60A) to remove any traces of water and to bind oxygenated metabolites, thereby providing the turpentine fraction. The oxygenated metabolites were then released from the column by rinsing with diethyl ether. Capillary GLC (flame ionization detector) was utilized for identification and quantification of the turpentine monoterpene and sesquiterpene olefin components [Hewlett Packard Model 5890 with cool (40° C.) on-column injection, detector at 300° C. and $H_2$ carrier at 14 psi., column:0.25 mm i.d.×30 m fused silica with 0.25 μm film of FFAP (Alltech) programmed from 35° C. to 50° C. at 50° C./min (5 min hold) then to 230° C. at 10° C./min]. Capillary GLC-MS was employed to confirm identifications by comparison of retention times and 70 eV mass spectra to those of authentic standards [Hewlett Packard Model 6890 gas chromatograph coupled to a Hewlett Packard Model 5872 mass spectrometer with cool (40° C.) on-column injection, and He carrier at 0.7 m/min, column:0.25 mm i.d.×30 m fused silica with 0.25 μm film of 5MS (Hewlett Packard) or polyethyleneglycol ester (AT1000, Alltech) and programmed from 40° C. to 50° C. at 50° C./min (5 min hold) then to 230° C. at 10° C./min.].

The sources of authentic terpene standards were as follows: α-longipinene, cyclosativene, sativene and α-ylangene were from *Abies balsamea* oleoresin; δ-selinene was from *Abies alba* oleoresin; α-, β-, and γ-himachalene, α- and δ-amorphene, α-muurolene, guaia-6,9-diene, α-cadinene, δ-selinene, germacrene A, β-ylangene, β-longipinene, E-α- and β-bisabolene were gifts from Larry Cool (University of California, Berkeley); germacrene B, and black pepper oleoresin containing a-cubebene and α-copaene, were gifts from Robert Adams (Baylor University); γ-humulene was from allspice seeds and as a gift from Ron Binder (USDA, Albany, Cailf.); sibirene and longicyclene were from *Pinus sibirica* oleoresin; longifolene was purchased from Sigma Chemical Co.; E-β-farnesene was from parsley leaf oil; germacrene D was from the essential oil of caraway and *Nepeta mussini*; β-caryophyllene was a gift from Rudolf Hopp (Haarmann and Reimer GmbH); γ-bisabolene was isolated from carrot roots; α-humulene was purchased from Fluka Chemical Co.; α-cubebene was from the essential oil of Valencia orange peels; α-selinene and seli-3,7(11)-diene were from celery seed; δ-cadinene was a gift from Margaret Essenberg (Oklahoma State University); α-guaiene was from patchouli essential oil; germacrene C was isolated from tomato leaf oil; bicyclogermacrene was from the essential oil of marjoram; and β-gurjunene was from ginger root. All other biochemicals and reagents were purchased from Sigma Chemical Co. or Aldrich Chemical Co., unless otherwise noted.

Figure 3:
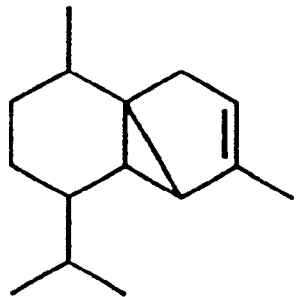
FIG. 3 shows the chemical structures of the six major sesquiterpenes present in the turpentine fraction of oleoresin extracted from unwounded Grand Fir (*Abies grandis*). The stereochemistry illustrated is relative. The percentage values represent the percentage contribution of each sesquiterpene to the sesquiterpene componenet of the turpentine fraction.
Figure 3:
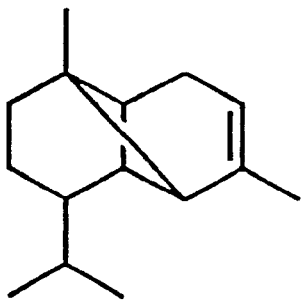
Figure 3:
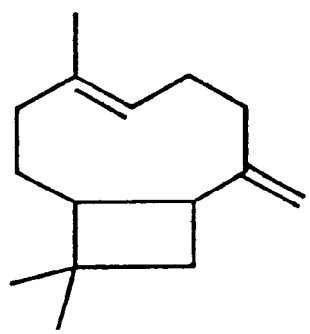
Figure 3:
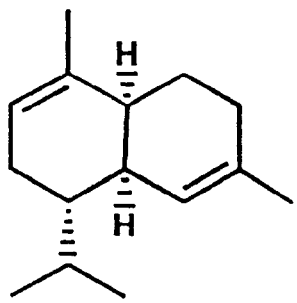
Figure 3:
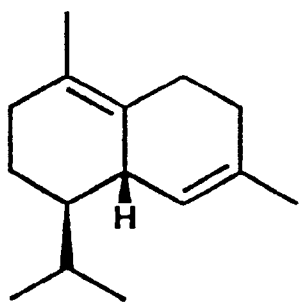
Figure 3:
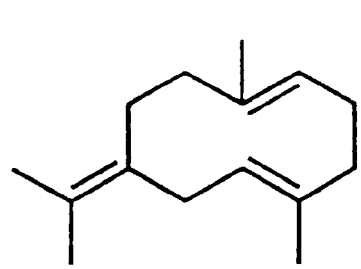

Sesquiterpene Composition of Oleoresin. Capillary GLC-MS analysis of grand fir stem turpentine revealed a minimum of 38 sesquiterpenes constituting approximately 12.5% of this material, with the remaining 87.5% composed of previously identified monoterpenes (Lewinsohn, E., et al., (1993) *Phytochem. Anal.* 4, 220–225). The six major sesquiterpenes present are α-cubebene, α-copaene, β-caryophyllene, α-muurolene, δ-cadinene and E,E-germacrene B, representing 62% of the total sesquiterpene fraction (FIG. 3). δ-Selinene, guaia-6,9-diene, δ-amorphene, sibirene, γ-humulene, longifolene, α-, β-, and γ-himachalene, α-longipinene, β-bisabolene, α-ylangene, sativene and cyclosativene were also identified (~33% of the sesquiterpene fraction), with the remaining minor fraction (~5%) composed of some 20 as yet unidentified sesquiterpene olefins.

The analysis of the sesquiterpene fraction of grand fir oleoresin reported here for the Rocky Mountain ecotype agrees well with a previous analysis of this material from the coastal ecotype (Smedman, L. A., et al., (1969) *Phytochemistry* 8, 1471–1479) with but minor differences between the former (19% germacrene B without detectable β-elemene) and the latter (8% β-elemene without detectable germacrene B). The discrepancy is likely the result of misidentification due to methodology (identification of β-elemene by retention time only), and has been rectified by recent re-analysis of the oleoresin of the coastal ecotype 3.

EXAMPLE 2

Sesquiterpene Synthase Activity in Wounded and Unwounded Grand Fir (*Abies grandis*) Sailing Stems Enzyme Isolation—Two-year-old grand fir (*Abies grandis* Lindl.) saplings were purchased from the Forestry Research Nursery, University of Idaho, Moscow, ID. Saplings were grown in standard potting mix (Sals Inc., Puyallup, Wash.) with a 16-h photoperiod (200–300 $\mu E/m^2 s$) and a 26° C. day/15° C. night temperature cycle, and were fertilized [15:30:15 (N:P:K)] weekly and watered daily.

Grand fir saplings in active growth were used as the enzyme source for determination of constitutive terpenoid synthases and of terpenoid synthases which had been induced in wounded stems by a standard wounding protocol (Funk, C., et al., (1994) *Plant Physiol.* 106, 999–1005). Stems from control saplings and saplings eight days after wounding (usually ten saplings) were harvested by removing the top and lateral growth, and cutting at about 5 cm from the base. The stems were chopped into 5–7 cm segments, frozen in liquid $N_2$ and, following removal of any needles, were ground to a powder in a liquid $N_2$-chilled No. 1 Wiley mill. The frozen powder was added to chilled extraction buffer (5 ml/g fresh tissue weight) consisting of 10 mM dibasic potassium phosphate and 1.8 mM monobasic potassium phosphate (pH 7.3), 140 mM NaCl, 20 mM β-mercaptoethanol, 10 mM $MgCl_2$, 5 mM $MnCl_2$, 10% (v/v) glycerol and 1% (w/v) each of polyvinylpyrrolidone ($M_r$ 40,000) and polyvinylpolypyrrolidone. The extract was stirred for 30 min at 0–4° C. and then clarified by centrifugation at 5000×g and filtration through Miracloth (Calbiochem). Partial purification of the extract was achieved by chromatography on O-diethylaminoethyl-cellulose (Whatman DE-52) as described previously (Gijzen, M., et al., (1991) *Arch. Biochem. Biophys.* 289, 267–273).

Enzyme Assay—The syntheses of [1-$^3$H]farnesyl diphosphate (125 Ci/mol) (Dehal, S. S. and Croteau, R., *Arch. Biochem. Biophys.* 261: 346–356 (1988)), [1-$^3$H] geranylgeranyl diphosphate (120 Ci/mol) (LaFever et al., *Arch. Biochem. Biophys.* 313: 139–149 (1994), and [1-$^3$H] geranyl diphosphate (250 Ci/mol) (Croteau, R., et al., (1994) *Arch. Biochem. Biophys.* 309, 184–192) have been reported previously. The sources of authentic terpene standards are as set forth in EXAMPLE 1.

The assay for recombinant sesquiterpene synthase (cyclase) activity was performed in 1 ml of buffer (extraction buffer without $MnCl_2$ or the polymeric adsorbents) containing 3.5 μM [1-$^3$H]farnesyl diphosphate and the total protein extracted from a 5 ml bacterial culture to produce $10^5$–$10^6$ dpm of product in 2 h at 31° C. The incubation mixture was overlaid with 1 ml pentane to trap volatile products. After incubation, the reaction mixture was extracted with pentane (3×1 ml) and the combined extract was passed through a $MgSO_4$-silica gel column to provide the terpene hydrocarbon fractions as before. The columns were subsequently eluted with 3×1 ml of ether to collect any oxygenated products, and an aliquot of each fraction was taken for liquid scintillation counting to determine conversion rate. The monoterpene synthase and diterpene synthase activity assays were similarly performed as described in detail elsewhere (LaFever, R. E., et al., (1994) *Arch. Biochem. Biophys.* 313, 139–149; Bohlmann, J., et al., (1997) *J. Biol. Chem.* 272, 21784–21792; Lewinsohn, E., et al., (1991) *Plant Physiol.* 96, 38–43).

For preparative incubations, the assay was scaled to 5 ml containing the total protein extracted from 100 ml of bacterial culture and 30 μM [1-$^3$H]farnesyl diphosphate, and the incubation time was extended to 8 h. Aliquots of the olefin fraction and the fraction containing oxygenated metabolites (diethyl ether eluate) were evaluated by liquid scintillation counting, and were analyzed by radio-GLC (Croteau, R. & Cane. D. E. (1985) *Methods Enzymol.* 110, 383–405; Satterwhite, D. M. & Croteau, R. (1988) *J. Chromatogr.* 452, 61–73) using a Gow-Mac 550P chromatograph that was equipped with a 3.18 mm×3.66 m stainless steel column packed with 5% OV17 (50% phenyl:50% methylsiloxane) on 100/120 mesh Gas Chrom Q (Alltech) and programmed from 150° C. to 220° C. at 2° C./min with He as carrier. The elution of co-injected standards was monitored with the Gow-Mac thermal conductivity detector (250° C. and 150 mA) and the radioactivity signal was continuously monitored with a Nuclear Chicago Model 8731 gas proportional counter; output data were processed using Perkin-Elmer Turbochrom Software.

Liquid scintillation counting was performed in 10 ml toluene:ethanol (7:3, v/v) containing 0.4% (w/v) Omnifluor (DuPont-NEN) at a $^3$H counting efficiency of 43%. Protein concentrations were determined by the method of Bradford (Bradford, M. M. (1976) *Anal. Biochem.* 72, 248–254) using the Bio-Rad reagent and bovine serum albumin as standard.

Biological Activity of Sesquiterpene Synthases Isolated From Wounded and Unwounded Grand Fir Stems. The soluble enzyme extract from non-wounded (control) sapling stems catalyzed the divalent metal ion-dependent conversion of [1-$^3$H]farnesyl diphosphate, the universal precursor of sesquiterpenoids (Cane, D. E. (1981) in *Biosynthesis of Isoprenoid Compounds* (Porter, J. W. & Spurgeon, S. L., eds) Vol. 1, pp 283–374, John Wiley and Sons, New York; Cane, D. E. (1990) *Chem. Rev.* 90, 1089–1103), to a labeled olefin fraction (12×2 ml assays yielded ~1.6 nmol of product) that upon radio-GLC analysis was shown to contain the same spectrum of sesquiterpenes found in the oleoresin.

Enzyme extracts were similarly prepared from sapling stems 9 days after wounding, utilizing a standard wounding protocol (Funk, C., et al., (1994) *Plant Physiol.* 106, 999–1005), and were assayed as before (2×2 ml assays yielded 1.8 nmol of product). Radio-GLC analysis of the olefin fraction revealed the presence of an apparently single component with retention time very similar to that of δ-cadinene. Partial purification of the extract from induced saplings to eliminate traces of endogenous oleoresin, followed by preparative-scale assay, provided sufficient material for capillary GLC-MS analysis. This higher resolution method revealed that the product derived from farnesyl diphosphate by the induced enzyme(s) mainly consisted of two components that were identified as δ-cadinene and E-α-bisabolene.

Differential loss of the δ-cadinene synthase activity during storage (data not shown) suggested that δ-cadinene and E-α-bisabolene were the products of two different enzymes. Boiled controls, and control reactions without farnesyl diphosphate, confirmed that both the constitutive and inducible sesquiterpene synthase activities observed were enzymatic and substrate-dependent. The $K_m$ value for [1-$^3$H] farnesyl diphosphate with the partially purified inducible sesquiterpene synthases was determined to be about 0.4 μM. It is of interest, and of probable physiological significance, that the constitutive sesquiterpene synthase activities differ from the wound-induced enzyme activities in product composition. A similar phenomenon has been previously observed with the constitutive and wound-inducible monoterpene and diterpene synthases of this tissue (Funk, C., et al., (1994) *Plant Physiol.* 106, 999–1005; Gijzen, M., et al., (1991) *Arch. Biochem. Biophys.* 289, 267–273).

EXAMPLE 3

Cloning a Full-Length E-α-Bisabolene Synthase cDNA

As set forth in Example 2, extracts of wounded Grand Fir stem are capable of converting farnesyl diphosphate to δ-cadinene and E-α-bisabolene. A PCR cloning strategy was utilized to clone one or both of the wound-inducible enzymes responsible for the formation of δ-cadinene and E-α-bisabolene.

Based on comparison of sequences of limonene synthase from spearmint (Colby, S. M., Alonso, W. R., Katahira, E. J., McGarvey, D. J., and Croteau, R. (1993) *J. Biol. Chem.* 268, 23016–23024), 5-epi-aristolochene synthase from tobacco (Facchini, P. J., and Chappell, J. (1992) *Proc. Natl. Acad.*

Sci. USA 89, 11088–11092), and casbene synthase from castor bean (Mau, C. J. D., and West, C. A. (1994) *Proc. Natl. Acad. Sci. USA* 91, 8497–8501), four conserved regions were identified for which a set of consensus degenerate primers (primers A–D) were synthesized. Primers A, B and C had been described previously (Steele, C. L., et al., (1995) *Proc. Natl. Acad. Sci. USA* 92, 4164–4168); the sequence of primer D had not previously been reported and was designed based on the conserved amino acid sequence motif DD(T/I)(I/Y/F)D(A/V)Y(A/G) (SEQ ID No:32) of the above noted terpene synthases. The sequence of sense primer D was 5'-GA(C/T) GA(C/T) III T(T/A)(T/C) GA(C/T) GCI (C/T)A(C/T) GG-3' (SEQ ID No:3). Each of the sense primers, A, B and D, were used for PCR in combination with antisense primer C (SEQ ID No:2) by employing a broad range of amplification conditions.

PCR was performed in a total volume of 50 µl containing 20 mM Tris/HCl (tris(hydroxymethyl) aminomethane/HCl, pH 8.4), 50 mM KCl, 5 mM MgCl$_2$, 200 µM of each dNTP, 1–5 µM of each primer, 2.5 units of Taq polymerase (BRL) and 5 µl of purified grand fir stem cDNA library phage as template (1.5×10$^9$ pfu/ml). Analysis of the PCR reaction products by agarose gel electrophoresis (Sambrock, J., Fritsch, E. F., and Maniatis, T. (1989) *Molecular Cloning: A Laboratory Manual*, 2nd Ed., Cold Spring Harbor Laboratory, Cold Spring Harbor, N.Y.) revealed that only the combination of primers C (SEQ ID No:2) and D (SEQ ID No:3) generated a specific PCR product of approximately 110 bps. This PCR product was gel purified, ligated into pT7Blue (Novagen), and transformed into *E. coli* XL1-Blue cells. Plasmid DNA was prepared from 41 individual transformants and the inserts were sequenced (DyeDeoxy Terminator Cycle Sequencing, Applied Biosystems). Four different insert sequences were identified, and were designated as probes 1, 2, 4 and 5.

Probe 1 was used to screen 10$^5$ cDNA phage plaques from the aforementioned, wounded grand fir stem library. The largest cDNA corresponding to probe 1, the 2424 bp cDNA AG1.28 (SEQ ID No:1) was recently described as a member of the Tpsd gene family (Bohlmann, J., et al., *J. Biol. Chem.* 272:21784–21792(1997)). The Tpsd gene family consists of genes for monoterpene, sesquiterpene and diterpene synthases from grand fir (*Abies grandis*) and Pacific yew (*Taxus brevifolia*). The members of the Tpsd gene family share at least 40% amino acid identity.

In order to generate a full-length cDNA corresponding to clone AG1.28 (SEQ ID No:1), 5'-RACE was carried out using the Marathon cDNA amplification system (Clontech) following the manufacturer's protocol. The reverse RACE primer specific for AG1.28 (SEQ ID No:1) was RJ1 (5'-AGA CGG TCG GAC AGC AGA AAG TGG G-3') (SEQ ID No:7). RJ1 (SEQ ID No:7) was used in combination with primer AP1 (SEQ ID No:6) (Clontech) and adaptor-ligated, wound-induced, grand fir stem library cDNA for PCR. The sequence of the adaptor ligated to the cDNA is set forth in (SEQ ID No:5) The resulting PCR product was cloned into pT7/Blue-vector (Novagen). An internal 404 bp cDNA fragment RJ8 (SEQ ID No:8) of the cloned PCR product was amplified using primers RJ1 (SEQ ID No:7) and RJ2 (5'-CTT GGA TCC ATG GCT GGC GTT TCT GCT G-3'), (SEQ ID No:9) which was designed to introduce a BamHI restriction site for subcloning of RJ8 (SEQ ID No:9) into the pBluescript SK(+)-derived plasmid pAG1.28 (Bohlmann, J., et al., *J. Biol. Chem.* 272:21784–21792(1997)).

A HincII site at nucleotide position 2382 of the cDNA insert in pAG1.28 (SEQ ID No:1), 32 nucleotides downstream of the stop codon of the 2350 bps ORF, was eliminated by site directed mutagenesis using the QuikChange site directed mutagenesis kit (Stratagene) following manufacturer's instructions using mutagenesis primer F (5'-GTT GCA ATA ATA ATT GAA ATA ATC TCA ACT ATG TTT CAC-3') (SEQ ID No:10) and primer R (5'-GTG AAA CAT AGT TGA GAT TAT TTC AAT TAT TAT TGC AAC-3') (SEQ ID No:11). cDNA fragment RJ8 (SEQ ID No:8) was digested with BamHI and HincII and ligated into BamHI/HincII-digested pAG1.28 resulting in plasmid pAG1. The nucleotide sequence of the cDNA insert of pAG1 is set forth in (SEQ ID No:12). For functional expression, the 2528 bp BamHI/XhoI cDNA insert of pAG1 (SEQ ID No:12) was subcloned into BamHI/XhoI-digested pGEX-4T-2 (Pharmacia) resulting in plasmid pGAG1. Inserts of all recombinant plasmids were completely sequenced on both strands via primer walking using the DyeDeoxy Terminator Cycle Sequencing method (Applied Biosystems). Sequence analysis was done using the Wisconsin Package Version 9.0, Genetics Computer Group (GCG), Madison, Wis.

EXAMPLE 4

Sequence Analysis of cDNA Clone AG1 (SEQ ID No:12)

A 2451 nucleotide ORF of AG1 (SEQ ID No:12) encodes a protein of 817 amino acids (SEQ ID No:13) of molecular weight 93,776 with a calculated pI at 5.03. The deduced amino acid sequence of clone AG1 (SEQ ID No:13) was compared with other cloned plant terpene synthases and resembles most closely two gymnosperm diterpene synthases, grand fir abietadiene synthase (71% similarity, 49% identity) (Stofer Vogel, B., et al., (1996) *J. Biol. Chem.* 271, 23262–23268) and *Taxus brevifolia* taxadiene synthase (71% similarity, 49% identity) (Wildung, M. R. & Croteau, R. (1996) *J. Biol. Chem.* 271, 9201–9204), and the grand fir sesquiterpene synthases AG4 encoding δ-selinene synthase (SEQ ID No:20) (70% similarity, 48% identity) and AG5 (SEQ ID No:23) encoding γ-humulene synthase (SEQ ID No:24) (68% similarity, 47% identity). The AG1 protein (SEQ ID No:13) shares 63–65% similarity and 41–42% identity with grand fir monoterpene synthases (Bohlmann, J., et al., *J. Biol. Chem.* 272:21784–21792(1997)).

Compared to the degree of sequence relatedness (percent identity and percent similarity) between the protein encoded by clone AG1 (SEQ ID No: 13) and gymnosperm terpene synthases, the protein encoded by clone AG1 (SEQ ID No:13) shows lower sequence relatedness with monoterpene synthases, sesquiterpene synthases and diterpene synthases of angiosperm origin (53–59% similarity, 28–34% identity) (Facchini, P. J. & Chappell, J. (1992) *Proc. Natl. Acad. Sci. USA* 89, 11088–11092 (epi-aristolochene synthase, a diterpene synthase, from tobacco); Colby, S. M., et al., (1993) *J. Biol. Chem.* 268, 23016–23024 (limonene synthase, a monoterpene synthase, from spearmint); Mau, C. J. D. & West, C. A. (1994) *Proc. Natl. Acad. Sci. USA* 91, 8497–8501 (casbene synthase, a diterpene synthase, from castor bean); Sun, T. & Kamiya, Y. (1994) *Plant Cell* 6, 1509–1518 (kaurene synthase A, a diterpene synthase, from Arabidopsis); Back, K. & Chappell, J. (1995) *J. Biol. Chem.* 270, 7375–7381 (vetaspiradiene synthase, a sesquiterpene synthase, from henbane); Bensen, R. J., et al., (1995) *Plant Cell* 7, 75–84 (kaurene synthase A, a diterpene synthase, from maize); Chen, X. -Y., et al., (1995) *Arch. Biochem. Biophys.* 324, 255–266 (δ-cadinene synthase, a sesquiterpene synthase, from cotton); Chen, X. -Y., et al., (1996) *J. Nat. Prod.* 59, 944–951 (δ-cadinene synthase, a sesquiterpene synthase, from cotton); Dudareva, N., et al., (1996)

*Plant Cell* 8, 1137–1148 (linalool synthase, a monoterpene synthase, from *Clarkia brewerii*); Yamaguchi, S., et al., (1996) *Plant J.* 10, 203–210 (kaurene synthase B, a diterpene synthase, from pumpkin); Yuba, A., et al., (1996) *Arch. Biochem. Biophys.* 332, 280–287 (limonene synthase, a monoterpene synthase, from Perilla)).

In total length, the AG1 protein (817 residues) (SEQ ID No:13) is closest to abietadiene synthase (868 residues) and taxadiene synthase (862 residues) and is 180–190 residues larger than grand fir monoterpene synthases and 220–230 residues larger than grand fir sesquiterpene synthases encoded by AG4 (SEQ ID No:20) and AG5 (SEQ ID No:24). The difference in length when comparing AG1 protein (SEQ ID No:13), abietadiene synthase and taxadiene synthase with grand fir monoterpene synthases and sesquiterpene synthases, is primarily accounted for by a 214 amino acid region corresponding to $Pro^{81}$-$Tyr^{294}$ of AG1 (SEQ ID No:13). This sequence element is highly conserved among AG1 (SEQ ID No:13) and the two diterpene synthases abietadiene synthase and taxadiene synthase (72–76% similarity, 52–58% identity), but is absent in all previously cloned grand fir monoterpene synthases (Bohlmann, J., et al., *J. Biol. Chem.* 272:21784–21792 (1997)) and in the sesquiterpene synthases AG4 (SEQ ID No:20) and AG5 (SEQ ID No:24).

Monoterpene and diterpene biosynthesis are compartmentalized in plastids whereas sesquiterpene biosynthesis is cytosolic (Kleinig, H. (1989) *Annu. Rev. Plant Physiol. Plant Mol. Biol.* 40, 39–53; Gershenzon, J. & Croteau, R. (1993) in *Lipid Metabolism in Plants* ed. Moore, T. S. Jr. (CRC Press, Boca Raton, Fla.), pp. 339–388; McGarvey, D. J. & Croteau, R. (1995) *Plant Cell* 7, 1015–1026). Thus, all cloned monoterpene synthases (Bohlmann, J., et al., *J. Biol. Chem.* 272:21784–21792(1997); Colby, S. M., et al., (1993) *J. Biol. Chem.* 268, 23016–23024; Dudareva, N., et al., (1996) *Plant Cell* 8, 1137–1148; Yuba, A., et al., (1996) *Arch. Biochem. Biophys.* 332, 280–287) and diterpene synthases (Stofer Vogel, B., et al., (1996) *J. Biol. Chem.* 271, 23262–23268; Wildung, M. R. & Croteau, R. (1996) *J. Biol. Chem.* 271, 9201–9204; Mau, C. J. D. & West, C. A. (1994) *Proc. Natl. Acad. Sci. USA* 91, 8497–8501; Sun, T. & Kamiya, Y. (1994) *Plant Cell* 6, 1509–1518; Bensen, R. J., et al., (1995) *Plant Cell* 7, 75–84; Yamaguchi, S., et al., (1996) *Plant J.* 10: 203–210) are encoded as preproteins bearing N-terminal transit peptides for import of these nuclear gene products into plastids where they are proteolytically processed to the mature form (Keegstra, K., et al., (1989) *Annu. Rev. Plant Physiol. Plant Mol. Biol.* 40, 471–501; von Heijne, G., et al., (1989) *Eur. J. Biochem.* 180, 535–545).

As cytosolic enzymes, all cloned sesquiterpene synthases, including the proteins encoded by clones AG4 (SEQ ID No:19) and AG5 (SEQ ID No:23) are encoded without transit peptides (Facchini, P. J. & Chappell, J. (1992) *Proc. Natl. Acad. Sci. USA* 89, 11088–11092; Back, K. & Chappell, J. (1995) *J. Biol. Chem.* 270, 7375–7381; Chen, X. -Y., et al., (1995) *Arch. Biochem. Biophys.* 324, 255–266; Chen, X. -Y., et al., (1996) *J. Nat. Prod.* 59, 944–951). Despite its high level of similarity with gymnosperm diterpene synthases, the protein encoded by clone AG1 (SEQ ID No:12) does not contain an N-terminal domain with features characteristic of plastidial targeting sequences (Keegstra, K., et al., (1989) *Annu. Rev. Plant Physiol. Plant Mol. Biol.* 40, 471–501; von Heijne, G., et al., (1989) *Eur. J. Biochem.* 180, 535–545). Lack of a transit peptide in the protein encoded by clone AG1 (SEQ ID No:12) explains the size difference (smaller by 45–50 amino acids) when compared with abietadiene synthase and taxadiene synthase. The relative location of the starting methionine of the AG1 protein (SEQ ID No:13) resembles the N-terminus of cytosolic sesquiterpene synthases encoded by clones AG4 (SEQ ID No:19) and AG5 (SEQ ID No:23) from grand fir, and is only 25 residues upstream of an RR-motif ($Arg^{25}$, $Arg^{26}$ in the AG1 protein (SEQ ID No:13)), which is conserved in many plant terpene synthases and is thought to approximate the N-terminus of the mature enzymes. An alignment of all cloned plant terpene synthases (Bohlmann, J., et al., *J. Biol. Chem.* 272:21784–21792(1997); Stofer Vogel, B., et al., (1996) *J. Biol. Chem.* 271, 23262–23268; Wildung, M. R. & Croteau, R. (1996) *J. Biol. Chem.* 271, 9201–9204; Facchini, P. J. & Chappell, J. (1992) *Proc. Natl. Acad. Sci. USA* 89, 11088–11092; Colby, S. M., et al., (1993) *J. Biol. Chem.* 268, 23016–23024; Mau, C. J. D. & West, C. A. (1994) *Proc. Natl. Acad. Sci. USA* 91, 8497–8501; Sun, T. & Kamiya, Y. (1994) *Plant Cell* 6, 1509–1518; Back, K. & Chappell, J. (1995) *J. Biol. Chem.* 270, 7375–7381; Bensen, R. J., et al., (1995) *Plant Cell* 7, 75–84; Chen, X. -Y., et al., (1995) *Arch. Biochem. Biophys.* 324, 255–266: Chen, X. -Y., et al., (1996) *J. Nat. Prod.* 59, 944–951; Dudareva, N., et al., (1996) *Plant Cell* 8, 1137–1148; Yamaguchi, S., et al., (1996) *Plant J.* 10: 203–210; Yuba, A., et al., (1996) *Arch. Biochem. Biophys.* 332, 280–287) shows little similarity upstream of the RR-motif, and N-terminal deletion analysis with grand fir monoterpene synthases, abietadiene synthase and mint limonene synthase revealed that residues upstream of the the RR-site are not required for catalytic activity.

In summary, comparative sequence analysis reveals features for the AG1 gene product (SEQ ID No:13) of both sesquiterpene and diterpene synthases of the gymnosperm Tpsd gene family and its functional identification therefore required expression of active enzyme.

EXAMPLE 5

Expression of cDNA Clone AG1 (SEQ ID No:12) in *E. coli* and Product Identification Expression of cDNA Clone AG1 (SEQ ID No:12) in *E. coli*. Plasmid pGAG1 was transformed into *E. coli* XL1-Blue (Sambrook, J., et al., (1989) *Molecular Cloning: A Laboratory Manual* (Cold Spring Harbor Lab., Cold Spring Harbor, N.Y.), 2nd Ed). The resulting bacterial strain *E. coli* XL1-Blue/pGAG1 was grown at 37° C. in 5 ml of LB medium (Sambrock, J., et al., (1989) *Molecular Cloning. A Laboratory Manual* (Cold Spring Harbor Lab., Cold Spring Harbor, N.Y.), 2nd Ed) supplemented with 100 µg ampicillin/ml and 12.5 µg tetracycline/ml to $A_{600}$=1.0, then induced by addition of 1 mM isopropyl-1-thio-β-D-galactopyranoside and grown for another 12 h at 20° C. Cells were harvested by centrifugation (2000×g, 10 min) and resuspended in either 1 ml monoterpene synthase assay buffer, 1 ml sesquiterpene synthase assay buffer, or 1 ml diterpene synthase assay buffer (Bohlmann, J., et al., *J. Biol. Chem.* 272:21784–21792(1997)).

Cells were disrupted by sonication (Braun-Sonic 2000 with microprobe at maximum power for 15 seconds at 0–4° C.), the homogenates were cleared by centrifugation (18,000×g, 10 min), and 1 ml of the resulting supernatant was assayed for monoterpene synthase activity with 2.5 µM of [1-$^3$H]geranyl diphosphate, for sesquiterpene synthase activity with 3.5 µM [1-$^3$H]farnesyl diphosphate, or for diterpene synthase activity with 5 µM [1-$^3$H]geranylgeranyl diphosphate following standard protocols (Dehal, S. S. & Croteau, R. (1988) *Arch. Biochem. Biophys.* 261, 346–356; LaFever, R. E., et al., (1994) *Arch. Biochem. Biophys.* 313, 139–149; Croteau, R. & Cane, D. E. (1985) *Methods Enzymol.* 110, 383–405). In the case of the monoterpene synthase and sesquiterpene synthase assays, the incubation mixture was overlaid with 1 ml pentane to trap volatile products. In all cases, after incubation at 31° C. for 2 h, the reaction mixture was extracted with pentane (3×1 ml) and the combined extract was passed through a 1.5 ml column of anhydrous $MgSO_4$ and silica gel (Mallinckrodt 60 Å) to provide the terpene hydrocarbon fraction free of oxygenated metabolites. The columns were subsequently eluted with 3×1 ml of ether to collect any oxygenated products, and an aliquot of each fraction was taken for liquid scintillation counting to determine conversion rate.

Characterization of Products of Recombinant E-α-Bisabolene Synthase Encoded by cDNA Clone AG1 (SEQ ID No:12) in *E. coli*. GLC-MS analysis of the sesquiterpene product was performed on a Hewlett-Packard 6890 gas chromatograph installed with a Hewlett-Packard 5MS capillary column (0.25 mm ID×30 m with a 0.25 $\mu$m coating of 5% phenyl methyl-siloxane) or AT-1000 capillary column (0.25 mm ID×30 m with a 0.25 $\mu$m coating of polyethylene), coupled to a 6890 quadrapole mass spectrometer operated at 70 eV. Split injections were made at an injector temperature of 250° C. and the oven followed a temperature program of 40° C., 5 min. hold, 10° C./min. to 250° C., 50° C./min. to 300° C., 1 min. hold Separations were performed under constant flow of 0.7 mL He/min. Monoterpene product analysis was performed on the above GLC-MS system equipped with a $\beta$-cyclodextrin column (0.25 mm ID×30 m with a 0.25 $\mu$m film thickness). Split injections were made with an injector temperature of 230° C. and an oven program as follows: 70° C. for 15 min. hold, 10° C./min. to 210° C., 1 min. hold. Flow rate as above. Mass spectra were compared to those of authentic standards and analyzed by Hewlett-Packard Chemstation software. Stereochemistry was assigned according to retention times of enantiomerically pure standards.

Enzymatic production of terpene olefin was observed only with geranyl diphosphate and farnesyl diphosphate, demonstrating that recombinant AG1 protein (SEQ ID No:13) combines monoterpene synthase and sesquiterpene synthase activity but has no diterpene synthase activity. The sesquiterpene product was identified as E-α-bisabolene by GLC-MS. Geranyl diphosphate was inefficiently converted by extracts of XL1-Blue/pGAG1 into the monoterpene (+)-4R-limonene. Conversion of geranyl diphosphate and farnesyl diphosphate, but not of geranylgeranyl diphosphate, is also a property of both δ-selinene synthase and γ-humulene synthase (SEE EXAMPLE 9) As more fully set forth in EXAMPLE 4, lack of a transit peptide for plastid import, and the higher level of similarity with grand fir sesquiterpene synthases encoded by AG4 (SEQ ID No:19) and AG5 (SEQ ID No:23) as compared to levels of similarity with monoterpene synthases, suggested that AG1 (SEQ ID No:12), in fact, encodes a sesquiterpene synthase, designated as E-α-bisabolene synthase rather than a monoterpene synthase. Under physiological conditions of the intact plant cell, cytosolic E-α-bisabolene synthase is unlikely to encounter geranyl diphosphate, which arises in plastids (Gershenzon, J. & Croteau, R. (1993) in *Lipid Metabolism in Plants* ed. Moore, T. S. Jr. (CRC Press, Boca Raton, Fla.), pp. 339–388), and thus there is no evolutionary pressure to select for discrimination against this adventitious substrate. E-α-Bisabolene synthase (SEQ ID No:13) shares several absolutely or highly conserved residues with other cloned plant terpene synthases : $Arg^{359}$, $His^{361}$, $Phe^{373}$, $Leu^{422}$, $Glu^{509}$, $Trp^{516}$, $Pro^{552}$, $Asp^{566}$, $Asp^{567}$, $Asp^{570}$, $Trp^{647}$, $Pro^{653}$, $Cys^{723}$ (Bohlmann, J., et al., *J. Biol. Chem.* 272:21784–21792(1997)). The conserved DDXXD (SEQ ID No:36) element of terpene synthases ($Asp^{566}$, $Asp^{567}$, $Asp^{570}$ of E-α-bisabolene synthase (SEQ ID No:13)) is involved in binding a divalent metal ion (Starks, C. M., et al., *Science* 277: 1815–1820(1997); Lesburg, C. A., et al., *Science* 277: 1820–1824(1997)), usually $Mn^{2+}$ or $Mg^{2+}$, which is thought to be employed in the ionization step of the reaction sequence to neutralize the negative charge of the diphosphate leaving group (Croteau, R. (1987) *Chem. Rev.* 87, 929–954; Cane, D. E. (1992) *Ciba Found. Symp. Ser.* 171, 163–167).

E-α-bisabolene synthase has not been cloned from any other organism before and is unusual as a terpene synthase which forms a single sesquiterpene product. Many terpene synthases have multiple products (Bohlmann, J., et al., *J. Biol. Chem.* 272:21784–21792(1997); Colby, S. M., et al., (1993) *J. Biol. Chem.* 268, 23016–23024; Munck, S. L. & Croteau, R. (1990) *Arch. Biochem. Biophys.* 282, 58–64; Wagschal, K., et al., (1991) *Tetrahedron* 47, 5933–5944; Savage, T. J., et al., (1994) *J. Biol. Chem.* 269, 4012–4020; Savage, T. J., et al., (1995) *Arch. Biochem. Biophys.* 320, 257–265) as a consequence of the electrophilic reaction mechanism (Gershenzon, J. & Croteau, R. (1993) in *Lipid Metabolism in Plants* ed. Moore, T. S. Jr. (CRC Press, Boca Raton, Fla.), pp. 339–388; Croteau, R. (1987) *Chem. Rev.* 87, 929–954; Cane, D. E. (1992) *Ciba Found. Symp. Ser.* 171, 163–167), whereas formation of a single product requires tight control over the fate of the highly reactive carbocationic reaction intermediate at the active site.

Figure 2:
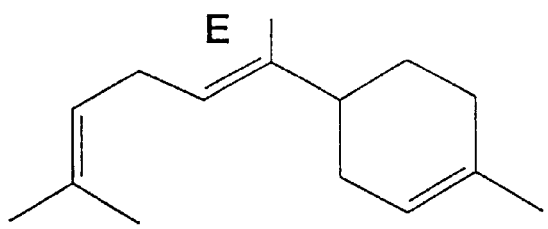
FIG. 2 shows the structures of E-α-bisabolene, juvenile hormone analogues todomatuic acid and juvabione, and insect juvenile hormone III.
Figure 2:
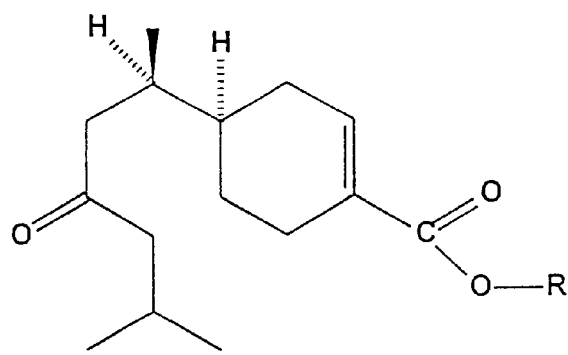
Figure 2:
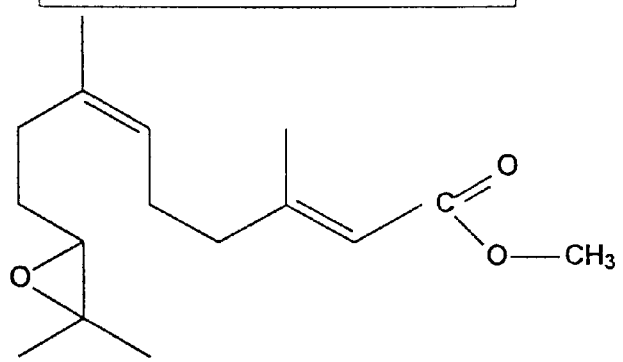

The absolute product specificity of bisabolene synthase is consistent with its role as a precursor to a proposed defensive compound, the juvabione juvenile hormone analogue, that inhibits larval insect development. Juvabione is the methylester of todomatuic acid which is structurally derived from bisabolene (FIG. 2). In Abies species, the sesquiterpene insect juvenile hormone analogue, juvabione, which has severe detrimental effects on insect development and reproduction (Bowers, W. S., et al., (1976) *Science* 193, 542–547; Bowers, W. S. (1991) in *Herbivores: Their Interaction with Secondary Plant Metabolites*, Vol. I, G. A. Rosenthal and M. R. Berenbaum, eds. (Acad. Press, San Diego), pp. 431–456), has been known since the discovery of "paper factor" in the mid 1960s (Slama, K. & Williams, C. M. (1965) *Proc. Natl. Acad. Sci. USA* 54, 411–414; Slama, K. & Williams, C. M. (1966) *Nature* 210, 329–330; Bowers, W. S., et al., (1966) *Science* 154, 1020–1021). In Grand Fir, todomatuic acid was found only after aphid feeding but was not detected in unchallenged trees (Puritch, G. S. & Nijholt, W. W. (1974) *Can. J. Bot.* 52, 585–587) which, together with wound-induction of bisabolene synthase enzyme activity (disclosed in EXAMPLE 6, herein), suggests de novo biosynthesis of the juvenile hormone analogue as an inducible defense response against insect herbivores.

EXAMPLE 6

Wound Induction of AG1 (SEQ ID No:12) mRNA Expression

Grand fir sapling stem tissue was wounded and harvested utilizing a standard procedure (Gijzen, M., et al., (1991) *Arch. Biochem. Biophys.* 289, 267–273). Total RNA was isolated (Lewinsohn, E., et al., (1994) *Plant Mol. Biol. Rep.* 4, 220–225) and 20 $\mu$g of RNA per gel lane was separated under denaturing conditions (Sambrook, J., et al., (1989) *Molecular Cloning: A Laboratory Manual* (Cold Spring Harbor Lab., Cold Spring Harbor, N.Y.), 2nd Ed) and transferred to nitrocellulose membranes (Schleicher and Schuell) according to the manufacturer's protocol. To prepare the hybridization probe, a 622 bp cDNA fragment (SEQ ID No:33) of AG1.28 (SEQ ID No:1) was amplified and labeled with [α-$^{32}$P]dATP by PCR with primer 1.28F (5'-TGA CAT AGT TCA CGA GGT GGC-3') (SEQ. ID No:34) and primer 1.28R (5'-CAG CGG TTC AAT GAG ACA CTC-3')(SEQ ID No:35). Blots were hybridized for 24 h at 60° C. in 3×SSPE and 0. 1% SDS, washed at 60° C. in 1×SSPE and 0.1%, SDS and subjected to autoradiography at −80° C. for 20 h.

Northern blots of total RNA extracted from sapling stems prior to wounding and after wounding were probed with the 622 bp cDNA fragment (SEQ ID No:33) which did not hybridize to any of the previously isolated grand fir terpene synthase cDNAs including abietadiene synthase, the two constitutive sesquiterpene synthase clones AG4 (SEQ ID No:19) and AG5 (SEQ ID No:23) or cloned monoterpene synthases (Bohlmann, J., et al., *J. Biol. Chem.* 272:21784–21792(1997); Stofer Vogel, B., et al., (1996) *J. Biol. Chem.* 271, 23262–23268). Messenger RNA was not detectable for E-α-bisabolene synthase prior to wounding. Following mechanical wounding of sapling stems, levels of E-α-bisabolene synthase mRNA transiently increased to a maximum 11–14 days after treatment, and thus demonstrated that increased mRNA accumulation for E-α-bisabolene synthase is responsible for the induced sesquiterpene defense response in grand fir. The slower increase of mRNA accumulation for E-α-bisabolene synthase as compared to rapid transcriptional activation of monoterpene synthase genes with a maximum mRNA accumulation 1–2 days after wounding (Bohlmann, J., et al., *J. Biol. Chem* 272:21784–21792(1997) shows that both early and late defensive responses in grand fir are triggered by wounding, possibly involving partly independent signalling pathways.

Whereas monoterpene and diterpene defense compounds are directed against insects early. during their attack,. bisabolene-derived phyto-juvenile hormone interferes with insect reproduction and development later during infestation. The inducible terpene-based chemical defense in grand fir is aimed at multiple targets in the physiology of attacking bark beetles and also the pathogenic fungi vectored to the grand fir trees by the bark beetles. The correct timing of each defense component is controlled by differential activation of the. large Tps-gene family. This multicomponent and multitarget chemical defense strategy is an important factor in the more than 300 million years of conifer evolution (Langenheim, J. H. (1969) *Science* 163, 1157–1169; Langenheim, J. H. (1990) *Am. Sci.* 78, 16–24; Langenheim, J. H. (1994) *J. Chem. Ecol.* 20, 1223–1280).

EXAMPLE 7

Isolation of cDNAs Encoding δ-Selinene Synthase and γ-Humulene Synthase cDNA Isolation, 5'-RACE and Construction of expression Vectors—Construction of the wound-induced Grand Fir stem cDNA library has been previously described (Stofer Vogel, B., et al., (1996) *J. Biol. Chem.* 271, 23262–23268), and the details of hybridization probe generation and library screening are set forth in EXAMPLE 3 and in Bohlmann, J., et al., *J. Biol. Chem.* 272, 21784–21792 (1997). As set forth in EXAMPLE 3, only the combination of primers C (SEQ ID No:2) and D (SEQ ID No:3) generated a specific PCR product of approximately 110 bps. Sub-cloning and sequencing of the 110 bp PCR product revealed that it consisted of four distinct sequences which were designated as probes 1, 2, 4 and 5. Upon screening of the wounded grand fir stem cDNA library, probes 4 (SEQ ID No:15) and 5 (SEQ ID No:25) hybridized, respectively, to two unique cDNA species designated ag4.30 (SEQ ID No:14) and ag5.9 (SEQ ID No:26).

Since neither of the cDNA isolates encoded a starting methionine, 5'-RACE was carried out using the. Marathon cDNA amplification kit (Clonetech) by following the manufacturer's protocol with slight modification. Total RNA was extracted from 60 saplings (two year-old; 6 or, 8 days after wounding) by scale-up of a published procedure (Lewinsohn, E., et al., (1994) *Plant Mol. Biol. Rep.* 12, 20–25). PolyA$^+$ mRNA was isolated using Oligotex beads and the spin column procedure described by Qiagen. To prevent RNA secondary structural features from obstructing full-length cDNA synthesis, three different cDNA synthesis reactions were performed by first denaturing the RNA at 42° C. or at 50° C., or by treatment with methylmercury hydroxide (Maniatis, T., et at., (1982) *Molecular Cloning: A Laboratory Manual*, 1st ed., pp 230–232, Cold Spring Harbor Laboratory Press, Cold Spring Harbor, N.Y.). Twice as much mRNA (2 μg) as recommended in the protocol was used, and PCR amplification was performed as indicated, except that a low fidelity Taq polymerase was substituted. The respective cDNA-specific reverse PCR primers were 5'-CTGCGAACCTTGAGAGTGGTCTGCAG-3' (SEQ ID No:16) for ag4.30 (SEQ ID No:14) and 5'-GTCTATCGATTCCCAGCCATTCC-3' (SEQ ID No:27) for ag5.9 (SEQ ID No:26).

The resulting PCR products were cloned into the pT7Blue-vector (Novagen) following standard procedures, and they were partially sequenced to reveal in each case a putative starting methionine codon, thus indicating that successful 5'-RACE syntheses had occurred. Full-length representatives were generated by designing 5'- and 3'-specific PCR primers for each cDNA for subsequent high fidelity amplification. The 5'-specific. primers were designed with a BamHI restriction endonuclease site immediately upstream of the 'starting methionine codon for each cDNA (5'-GGAGGATCCATGGCTGAGATTTCTG-3' (SEQ ID No:17) for ag4.30 (SEQ ID No:14) and 5'-TGGTACCATGGCTGGCGTTTCTGCTGTATC-3' (SEQ ID No:28) for ag5.9 (SEQ ID No:26)). The 3'-specific primers were designed to encompass the stop codon; the ag4.30 primer included a XhoI site whereas the ag5.9 primer included an EcoRI site (5'-AAAGTCTCGAGATATTAATTATTGCC-3' (SEQ ID No:18) for ag4.30 and 5'-TATGAATTCTCAAATAGGCACGGGGAC-3' (SEQ ID No:29) for ag5.9) to facilitate ligation into the pGEX-4T-1 expression vector (Pharmacia).

PCR reactions were performed at 94° C. for 1 min, 50° C. for 1 min, and 72° C. for 6 min, for 30 cycles followed by a 5 min final extension period at 72° C., using Pfu polymerase and the buffer described by the manufacturer (Stratagene). The resulting DNA fragments were sequentially cloned by standard methods, first into pBluescript (SK−) (Stratagene), then into pGEX (Pharmacia) vectors designated as pGAG4 and pGAG5. For firmer subcloning of cDNAs into the pSBETa vector for high-level expression (Schenk, P. M., et al., (1995) *Biotechniques* 19, 196–200), inserts of pGAG4 and pGAG5 were amplified by PCR (Stratagene Pfu polymerase as above) using primer combinations 4-NdeI (5'-CTGGTTCCGCGTGGACATATGGCTGAGT-3') (SEQ ID No:21) and 4-BamHII (5'-CTACAACCAAG- AGGATCCCTATTCCTCCATTGG-3') (SEQ ID No:22) with pGAG4, and 5-NdeI (5'-CTGGTTCCGCGTGG-ACATATFGGCTCAG-3') (SEQ ID No:30) and 5-BamHI (5'-GTCAGTGACGATGGATCCTCAAATAGGCAC-GG-3') (SEQ ID No:31) with pGAG5. The PCR products were digested with the above indicated restriction enzymes, purified by ultrafiltration, and then ligated into NdeI/BamHI-digested pSBETa to yield plasmid pSBAG4 and pSBAG5, respectively.

The original isolates, ag4.30 (SEQ ID No:14) and ag5.9 (SEQ ID No:26), and their corresponding full-length cDNA inserts of ag4 (SEQ ID No:20)(δ-selinene synthase)in pGAG4 and pSBAG4, and of ag5 (SEQ ID No:23)(γ-humulene synthase) in pGAG5 and pSBAG5, were entirely sequenced on both strands via primer walking using the dye-terminator-cycle sequencing method (Applied Biosystems) on a ABI 373 DNA Sequencer Stretch instrument at the Washington State University Laboratory for Biotechnology and Bioanalysis. Sequence analysis was done using programs from the Wisconsin Package Version 9.0 of the Genetics Computer Group (Genetics Computer Group (1996) *Program Manual for the Wisconsin Package, Version 9.0*, Genetics Computer Group, Madison, Wis.).

EXAMPLE 8

Sequence Analysis of cDNA Clone Inserts AG4 (SEQ ID No:19) and AG5 (SEQ ID No:23)

The δ-selinene synthase cDNA (SEQ ID No:19) encodes a protein that is 581 amino acids in length (SEQ ID No:20) with a predicted molecular weight of 67,625, and the γ-humulene synthase cDNA (SEQ ID No:23) encodes a protein of 593 residues (SEQ ID No:24) with a predicted molecular weight of 67,937. The γ-humulene synthase sequence (SEQ ID No:23) contains a stop codon in-frame with the putative initiation methionine at −21 bp of the 89 bp 5'-untranslated region, whereas the δ-selinene synthase sequence (SEQ ID No:19) is truncated at −12 bp. The nucleotide sequence surrounding the putative starting ATG of both sesquiterpene synthase genes is conserved, and resembles that which surrounds the initiating methionine of other plant genes (Joshi, C. P. (1987) *Nucl. Acids Res.* 15, 6643–6653). These data support the proposed location of the initiation sites and, thus, the identification of both cDNAs as sesquiterpene synthases, since the predicted molecular weights are appropriate for this class of cytosolic enzymes (Facchini, P. J. & Chappell, J. (1992) *Proc. Natl. Acad. Sci. USA* 89, 11088–11092; Chen, X. -Y., et al., (1995) *Arch. Biochem. Biophys.* 324, 255–266). Additionally, the proteins encoded by both cDNAs (SEQ ID Nos:20 and 24) lack a plastidial targeting peptide found in both monoterpene synthase and diterpene synthase preproteins (Stofer Vogel, B., et al., (1996) *J. Biol. Chem.* 271, 23262–23268; Bohlmann, J., et al., (1997) *J. Biol. Chem.* 272, 21784–21792; Colby, S. M., et al., (1993) *J. Biol. Chem.* 268, 23016–23024; Mau, C. J. D. & West, C. A. (1994) *Proc. Natl. Acad. Sci. USA* 91, 8497–8501).

Comparison of the deduced amino acid sequences indicates that they are 83% similar and 65% identical to each other, and both sesquiterpene synthases show about 66% similarity and 45% identity when compared to other terpenoid synthases from conifers, including abietadiene synthase (diterpene) from grand fir (Stofer Vogel, B., et al., (1996) *J. Biol. Chem.* 271, 23262–23268), myrcene synthase, pinene synthase and limonene synthase (monoterpenes) from this species (Bohlmann, J., et al., (1997) *J. Biol. Chem.* 272, 21784–21792), and the taxadiene synthase (diterpene) from Pacific yew (Wildung, M. R. & Croteau, R. (1996) *J. Biol. Chem.* 271, 9201–9204). Comparison of these gymnosperm sesquiterpene synthases (SEQ ID Nos:20 and 24) to a range of terpenoid synthases from angiosperm species (Back, K. & Chappell, J. (1995) *J. Biol. Chem.* 270, 7375–7381 (epi-aristolochene synthase from tobacco); Chen, X. -Y., et al., (1995) *Arch. Biochem. Biophys.* 324, 255–266 (δ-cadinene synthase from cotton)) reveals similarities of about 56% and identities in the range of 30%.

Interestingly, the gymnosperm sesquiterpene synthases show a greater resemblance to gymnosperm monoterpene synthases and diterpene synthases than they do to angiosperm sesquiterpene synthases, suggesting an ancient divergence of the gymnosperm tpsd family, which consists of monoterpene, sesquiterpene, and diterpene synthases (Bohlmann, J., et al., (1997) *J. Biol. Chem.* 272, 21784–21792). Comparison with microbial sesquiterpene synthases did not reveal a significant similarity. For example, the δ-selinene and γ-humulene synthases (SEQ ID Nos:20 and 24) show 45–46% similarity and 18–22% identity when compared to trichodiene synthase from *Fusarium sporotrichioides* (Hohn, T. M. & Beremand, P. D. (1989) *Gene* 79, 131–138).

Studies employing amino acid-modifying reagents have implicated histidine, cysteine and arginine residues in catalysis by terpene synthases from angiosperms and gymnosperms (LaFever, R. E., et al., (1994) *Arch. Biochem. Biophys.* 313, 139–149; Dehal, S. S. & Croteau, R. (1988) *Arch. Biochem. Biophys.* 261, 346–356; Munck, S. L. & Croteau, R. (1990) *Arch. Biochem. Biophys.* 282, 58–64; Savage, T. J., et al., (1994) *J. Biol. Chem.* 269, 4012–4020; Lewinsohn, E., et al., (1992) *Arch. Biochem. Biophys.* 293, 167–173; Rajaonarivony, J. I. M., et al., (1992) *Arch. Biochem. Biophys.* 296, 49–57; Rajaonarivony, J. I. M., et al., (1992) *Arch. Biochem. Biophys.* 299, 77–82; Savage, T. J., et al., (1995) *Arch. Biochem. Biophys.* 320, 257–265). Comparisons of all published terpene synthase sequences reveal $cys^{507}$ (with reference to the numbering of the amino acid sequence of γ-humulene synthase (SEQ ID No:24)) as the only universally conserved cysteine residue, and $his^{95}$ and $his^{141}$ (with reference to the numbering of the amino acid sequence of γ-humulene synthase (SEQ ID No:24)) as the only conserved histidines. However, comparisons restricted to the sesquiterpene synthases reveal an additional conserved histidine residue at position 283 of the γ-humulene synthase sequence (SEQ ID No:24). Comparison among the sesquiterpene synthases also shows that eight arginine residues are conserved at positions 136, 139, 243, 247, 306, 329, 364 and 485 of γ-humulene synthase (SEQ ID No:24), a surprising number considering the broad taxonomic distribution of plant species compared (Facchini, P. J. & Chappell, J. (1992) *Proc. Natl. Acad. Sci. USA* 89, 11088–11092; Back, K. & Chappell, J. (1995) *J. Biol. Chem.* 270, 7375–7381; Chen, X. -Y., et al., (1995) *Arch. Biochem. Biophys.* 324, 255–266).

A highly conserved aspartate-rich motif (DDXXD) (SEQ ID No:36) is found in all terpenoid synthases, including those of microbial origin, as well as in prenyltransferases (Chen, A., et al., (1994) *Protein Sci.* 3, 600–607) which operate by a related mechanism on the common prenyl diphosphate substrates (Cane, D. E. (1980) *Tetrahedron* 36, 1109–1159; Poulter, C. D: & Rilling, H. C. (1978) *Acc. Chem. Res.* 11, 307–313; Poulter, C. D. & Rilling, H. C. (1981) in *Biosynthesis of Isoprenoid Compounds* (Porter, J. W. & Spurgeon, S. L., eds) Vol. 1, pp. 161–224, John Wiley and Sons, New York). Considerable evidence based on X-ray structural investigation and directed mutagenesis indicates that this motif is responsible for binding the divalent metal ion of the substrate disphosphate-metal ion complex (Tarshis, L. C., et al., (1994) *Biochemistry* 33, 10871–10877; Cane, D. E. & Xue, Q. (1996) *J. Am. Chem. Soc.* 118, 1563–1564). A second DDXXD (SEQ ID No:39) motif is also present, of which the second aspartate residue is conserved among terpenoid synthases; the last aspartate residue is found only in the grand fir sesquiterpene synthases.

Sequence comparison between the δ-selinene synthase (SEQ ID No:20) and the γ-humulene synthase (SEQ ID No:24) indicates that the two enzymes are very similar, but with the similarity decreasing toward the carboxy terminus of the proteins. This observation is consistent with the conclusions drawn from the aforementioned domain swapping experiments with related sesquiterpene synthases (Back, K. & Chappell, J. (1996) *Proc. Natl. Acad. Sci. USA* 93, 6841–6845) which suggest that the amino terminal regions of the proteins are involved in the initial, common steps of the cyclization reactions and that the more carboxy terminal regions are responsible for determining the specific product outcome.

The two gymnosperm sesquiterpene synthases (SEQ ID Nos:20 and 24) clearly resemble in sequence the angiosperm terpenoid synthases (roughly 55% similarity and 30% identity), with levels of conservation similar to those observed between the angiosperm sesquiterpene and diterpene synthases and the monoterpene synthases of this plant class (Bohlmann, J., et al., (1997) *J. Biol. Chem.* 272, 21784–21792; Chen, X. -Y., et al., (1995) *Arch. Biochem. Biophys.* 324, 255–266). The regions of highest similarity between the various terpenoid synthases are clustered and likely represent those elements responsible for common cyclization chemistry (e.g., ionization, charge stabilization, deprotonation). The more variable regions likely impart the specific shape of the active site that enforces substrate and intermediate conformation and thus dictates the specific product outcome. The crystal structures of two sesquiterpene cyclases have recently been described for pentalenene synthase from Sireptomyces UC5319 (Lesburg, C. A., et al., (1997) *Science* 277, 1820–1824) and epi-aristolochene synthase from tobacco (Starks, C. M., et al., (1997) *Science* 277, 1815–1820). Both enzymes have been shown to possess very similar fold structures related to farnesyl diphosphate synthase (Tarshis, L. C., et al., (1994) *Biochemistry* 33, 10871–10877), and to consist of mostly antiparallel α-helices that form a large central cavity.

EXAMPLE 9

Characterization of Substrate Specificity and Kinetic Parameters for δ-Selinene Synthase (SEO ID No:20) and γ-Humulene Synthase (SEQ ID No:24)

The substrate specificity and other kinetic. parameters of γ-humulene synthase (SEQ ID No:24) and δ-selinene synthase (SEQ ID No:20) were investigated in order to confirm the identification and classification of these enzymes. The $K_m$ values for [1-$^3$H]farnesyl diphosphate with γ-humulene synthase (SEQ ID No:24) and δ-selinene synthase (SEQ ID No:20) were estimated to be about 4.5 µM and 1.5 µM, respectively. The metal ion requirements of γ-humulene synthase (SEQ ID No:24) and δ-selinene synthase (SEQ ID No:20) were also evaluated, as cofactor specificity is often characteristic of the different terpenoid synthase types (Savage, T. J., et al., (1994) *J. Biol. Chem.* 269, 4012–4020).

δ-Selinene synthase (SEQ ID No:20) shows a distinct preference for $Mg^{2+}$; the maximum rate with $Mn^{2+}$ is less than 10% of that with $Mg^{2+}$ at saturation. By contrast, γ-humulene synthase (SEQ ID No:24) can utilize $Mg^{2+}$ or $Mn^{2+}$ with comparable velocities in the cyclization reaction. For both enzymes, the $K_m$ value for $Mg^{2+}$ is about 125 µM, and for $Mn^{2+}$ about 25 µM. Neither of these sesquiterpene synthases requires $K^+$ or other monovalent cation for activity. In contrast, the monoterpene synthases from conifers require $Mn^{2+}$ or $Fe^{2+}$ for activity, but $Mg^{2+}$ fails to support catalysis (Bohlmann, J., et al., (1 997) *J. Biol. Chem.* 272, 21784–21792; Lewinsohn, E., et al., (1992) *Arch. Biochem. Biophys.* 293, 167–173), and these enzymes also exhibit an absolute requirement for a monovalent cation, with $K^+$ preferred (Bohlmann, J., et al., (1997) *J. Biol. Chem.* 272, 21784–21792; Savage, T. J., et al., (1994) *J. Biol. Chem.* 269, 4012–4020).

Figure 4:
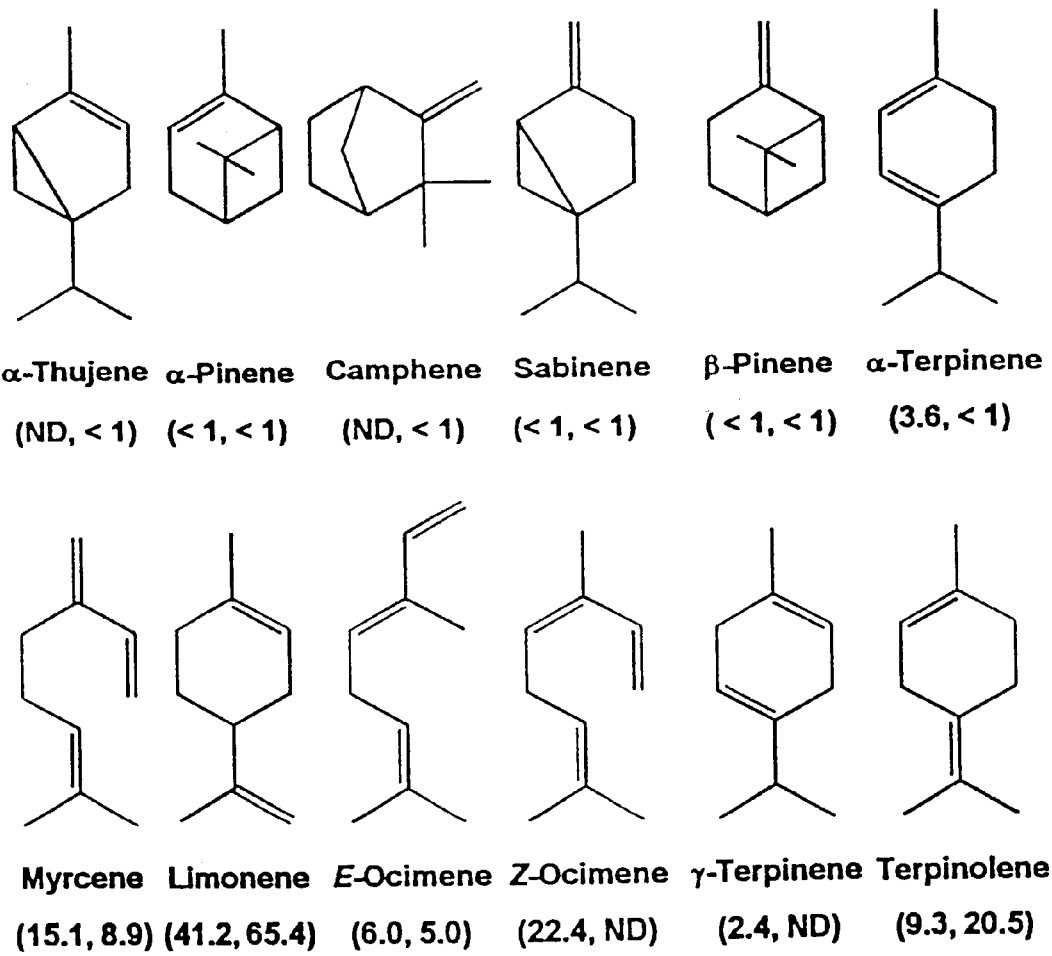
FIG. 4 shows the identities and relative amounts of the monoterpene products produced by the sesquiterpene synthases δ-selinene synthase (SEQ ID No:20) and γ-humulene synthase (SEQ ID No:24), in vitro, when provided with geranyl diphosphate as substrate. The percentage contribution to the total monoterpene fraction is indicated in parentheses for the δ-selinene synthase (first value shown in parentheses) and γ-humulene synthase (second value shown in parentheses). ND means not detected.

Substrate specificity of δ-selinene synthase (SEQ ID No:20) and γ-humulene synthase (SEQ ID No:24) was evaluated by comparing farnesyl diphosphate ($C_{15}$) to geranyl diphosphate ($C_{10}$) and geranylgeranyl diphosphate ($C_{20}$) at saturation as precursors of the respective terpene olefins. Both enzymes failed to generate detectable olefinic products from geranylgeranyl diphosphate, whereas both synthesized monoterpenes from geranyl diphosphate at roughly half the rate of sesquiterpene biosynthesis from farnesyl diphosphate. The identities of the monoterpene products produced by the sesquiterpene synthases were determined by GLC-MS and are set forth in FIG. 4. Limonene is the principal monoterpene product of both synthases, with most of the other products being made in roughly comparable proportions by each, with the notable exception of E-ocimene which is a major product of δ-selinene synthase (SEQ ID No:20) (22.4%) but is not detectable as a product of γ-humulene synthase (SEQ ID No:24). γ-Humulene synthase (SEQ ID No:24) produces detectable amounts of camphene, the biosynthesis of which requires a Wagner-Meerwein rearrangement as with longifolene and sativene; δ-selinene synthase (SEQ ID No:20) does not produce this monoterpene.

Although δ-selinene synthase (SEQ ID No:20) and γ-humulene synthase (SEQ ID No:24) are both capable of producing monoterpenes when presented with geranyl diphosphate, several lines of evidence indicate that these enzymes are, in fact, sesquiterpene synthases. Firstly, as discussed in more detail in EXAMPLE 8, cDNAs encoding these enzymes (SEQ ID Nos:19 and 23) do not appear to encode preproteins bearing a plastidial transit peptide characteristic of monoterpene (and diterpene) synthases, but rather mature proteins of a size typical of cytosolic sesquiterpene synthases. Secondly, the divalent and monovalent ion requirements do not resemble those of the monoterpene synthases, but rather those of other sesquiterpene synthases. Finally, the acyclic monoterpenes (ocimenes) produced by δ-selinene synthase (SEQ ID No:20) and γ-humulene synthase (SEQ ID No:24) from geranyl diphosphate are not found in the turpentine fraction of grand fir oleoresin (Lewinsohn, E., et al., (1993) *Phytochem. Anal.* 4, 220–225; Lewinsohn, E., et al., (1991) *Plant Physiol.* 96, 38–43; Smedman, L. A., et al., (1969) *Phytochemistry* 8, 1471–1479).

The accumulated evidence therefore clearly supports the identification of these novel enzymes (SEQ ID Nos:20 and 24) as sesquiterpene synthases. Since sesquiterpene biosynthesis occurs in the cytosol where the precursor farnesyl diphosphate is also synthesized, whereas the monoterpene synthases are compartmentalized within plastids where the precursor geranyl diphosphate also arises (Gershenzon, J. & Croteau, R. (1993) in *Lipid Metabolism in Plants* (Moore, Jr., T. S., ed) pp 340–388, CRC Press, Boca Raton, Fla.; Colby, S. M., et al., (1993) *J. Biol. Chem.* 268, 23016–23024; Belingheri, L., et al., (1988) *J. Plant Physiol.* 132, 80–85; Gleizes, M., et al., (1983) *Planta* 159, 373–381), the ability of these sesquiterpene synthases to produce monoterpenes in vitro may simply represent the adventitious utilization of a substrate that is never encountered in vivo and against which there is no evolutionary pressure to discriminate. It now seems likely that the adventitious utilization of geranyl diphosphate by the sesquiterpene synthases accounts, in part, for the relatively high level of limonene synthase activity observed in crude stem extracts of grand fir (Gijzen, M., et al., (1991) *Arch. Biochem. Biophys.* 289, 267–273).

EXAMPLE 10

Product Profiles of δ-Selinene Synthase (SEQ 1D No:20) and γ-Humulene Synthase (SEQ ID No:24) Expressed In Vitro Expression of Sesquiterpene Synthase cDNAs AG4 (SEQ ID No:19) and AG5. (SEQ ID No:23) in *E. coli*. Both putative sesquiterpene cyclase cDNAs (SEQ ID Nos:19 and 23) were expressed in bacterial strains *E. coli* XL1-Blue/pGAG4, *E. coli* XL1-Blue/pGAG5, *E. coli* BL21(DE3)/pSBAG4, and *E. coli* BL21(DE3)/pSBAG5 as set forth in EXAMPLE 7. Bacteria were grown to $A_{600}$=0.5 at 37° C. in 5 ml or 100 ml of LB medium supplemented with 100 μg ampicillin/ml or 30 μg kanamycin/ml as determined by the vector. Cultures were then induced by addition of 1 mM isopropyl-1-thio-β-D-galactopyranoside and grown for another 12 h at 20° C. Cells were harvested by centrifugation (2000×g, 10 min) and resuspended in either 1 ml or 5 ml sesquiterpene synthase assay buffer (EXAMPLE 2). Cells were disrupted by sonication (Braun-Sonic 2000 with microprobe at maximum power for 15 seconds at 0–4° C.) and the homogenates were cleared by centrifugation (18,000×g, 10 min). Preparative assays were employed to generate product for GLC-MS analysis, as set forth in EXAMPLE 2, with quantification of composition via the total ion current chromatogram.

Product Profile of Recombinant δ-Selinene Synthase (SEQ ID No:20) In Vitro. Large scale incubation with [1-$^3$H]farnesyl diphosphate, followed by isolation of the derived olefins and GLC-MS analysis, revealed the enzyme encoded by AG4 (SEQ ID No:19) to produce mainly δ-selinene, for which this synthase is named, along with germacrene B and guai-6,9-diene as major products. In addition, 17 other sesquiterpene olefins were identified by GLC-MS, and another 14 products which displayed the characteristic sesquiterpene olefin mass spectral pattern [m/z 204 ($P^+$), 189 ($P^+$—$CH_3$), and 161 ($P^+$—$C_3H_7$)], were detected for a total of at least 34 different sesquiterpene products (TABLE 1).

TABLE 1

Sesquiterpene products of δ-selinene synthase and γ-humulene synthase Products are listed in order of their abundance and were identified by matching GLC retention time and mass spectrum to authentic standards. Compounds labeled as (tent.) were tentatively identified based on the mass spectrum alone.

| δ-Selinene Synthase (ag4) (SEQ ID No. 20) | | γ-Humulene Synthase (ag5) (SEQ ID No: 24) | |
| --- | --- | --- | --- |
| sesquiterpene | % | sesquiterpene | % |
| δ-Selinene | 25.3 | γ-Humulene | 28.6 |
| E,E-Germacrene B | 17.4 | Sibirene | 15.1 |
| Guaia-6,9-diene | 9.7 | Longifolene | 11.8 |
| Germacrene A | 6.7 | β-Himachalene | 7.2 |
| δ-Amorphene | 6.4 | γ-Himachalene | 5.8 |
| Unknown | 4.7 | α-Himachalene | 4.8 |
| Unknown | 4.4 | β-Bisabolene | 3.9 |
| Germacrene C | 3.4 | α-Longipinene | 3.4 |
| α-Amorphene | 2.7 | Sativene | 3.1 |
| Unknown | 2.6 | α-Ylangene | 2.7 |
| α-Selinene | 1.7 | β-Gurjunene | 2.0 |
| β-Caryophyllene | 1.5 | γ-Bisabolene | 1.9 |
| δ-Cadinene | 1.4 | β-Longipinene | 1.5 |
| Unknown | 1.4 | E-β-Farnesene | 1.3 |
| Unknown | 1.3 | E-α-Bisabolene | 0.9 |
| Z-E-Germacrene B (tent.) | 1.3 | δ-Amorphene | 0.5 |
| Seli-3,7(11)-diene | 1.2 | α-Amorphene | 0.5 |
| Germacrene D | 0.8 | β-Ylangene | 0.3 |
| α-Humulene | 0.7 | 1,5,9-trimethylcyclododeca- | 0.2 |
| β-Bisabolene | 0.7 | 1,5,9-triene (tent. 2 isomers) | |
| Sibirene | 0.7 | Longicyclene | 0.2 |
| α-Guiaene | 0.2 | β-Cubebene | 0.1 |
| α-Cadinene | 0.2 | α-Copaene | 0.1 |
| α-Ylangene | 0.1 | α-Cubebene | 0.1 |
| α-Copaene | 0.1 | Z,E-Germacrene B (tent.) | 0.1 |
| 9 unknowns, each <1% | 3.4 | Cyclosativene | <0.1 |
| | | 26 unknowns, each <1% | 4.1 |

A cyclization scheme to account for the generation of this remarkable number of products has been formulated in which the route to the principal product, δ-selinene, is based upon the formation of other eudesmane sesquiterpenes (Cane, D. E. (1981) in *Biosynthesis of Isoprenoid Compounds* (Porter, J. W. & Spurgeon, S. L., eds) Vol. 1, pp 283–374, John Wiley and Sons, New York; Cane, D. E. (1990) *Chem. Rev.* 90, 1089–1103; Cane, D. E. (1992) in *Secondary Metabolites: Their Function and Evolution* (Chadwick, D. J. & Whelan, J., eds) pp 163–183, Ciba Foundation Symposium 171, John Wiley and Sons, West Sussex, UK). The cyclization scheme is set forth in Steele et al. *J. Biol. Chem.* 273: 2078–2089 (1998), incorporated herein by reference.

Product Profile of Recombinant γ-Humulene Synthase (SEQ ID No:24) In Vitro. Although the array of products generated by δ-selinene synthase (SEQ ID No:20) is remarkable, an even more bewildering spectrum of sesquiterpene olefins is produced by the synthase encoded by AG5 (SEQ ID No:23). γ-Humulene, the principal olefin for which this synthase has been named, sibirene and longifolene were identified by GLC-MS analysis as major products. In addition, 23 other sesquiterpenes were identified, along with 26 unknown sesquiterpene olefins, for a total of 52 different products (TABLE I). These products range in complexity from the simple acyclic olefin E-β-farnesene, to the complex tetracyclic olefins longicyclene and cyclosativene.

A reaction scheme has been proposed to account for the remarkable array of sesquiterpenes produced, in vitro, by γ-humulene synthase (SEQ ID No:24) which appears to utilize exclusively cisoid-nerolidyl diphosphate as an intermediate, for example, in the formation of the principal product. Due to its complexity, the cyclization scheme is set forth in Steele et al. *J. Biol. Chem.* 273: 2078–2089(1998).

Although γ-humulene synthase (SEQ ID No:24) appears to be restricted to utilization of the cisoid-nerolidyl diphosphate intermediate, as opposed to δ-selinene synthase (SEQ ID No:20). which utilizes both cisoid- and transoid-forms, the former is able to catalyze formation of the greater number and the more diverse products, including acyclic, monocyclic, bicyclic, tricyclic and tetracyclic types, as well as olefins produced by Wagner-Meerwein rearrangements. It is worth noting that, in spite of the remarkable number of different sesquiterpene skeletal types generated by the recombinant δ-selinene synthase (SEQ ID No.20) and γ-humulene synthase (SEQ ID No:24), deprotonation in each set of structures occurs from the same few carbons of the common substrate, providing at least a measure of uniformity between the two. The γ-humulene synthase (SEQ ID No:24), in particular, catalyzes several very complex reaction cascades and generates far more products than any terpenoid synthase thus far described, and, along with δ-selinene synthase (SEQ ID No:20), it accounts for many of the constitutively produced cortical sesquiterpenes. However, the cDNA species encoding synthases responsible for the formation of several of the more abundant constitutive sesquiterpenes of grand fir oleoresin (e.g., α-muurolene, α-copaene, α-cubebene and β-caryophyllene) have not yet been acquired. Although E-α-bisabolene is a product of γ-humulene synthase (SEQ ID No:24), and δ-cadinene is a product of δ-selinene synthase (SEQ ID No:20), these two sesquiterpenes account for only a small fraction of the many olefins generated by these two synthases. Thus, γ-humulene synthase (SEQ ID No:24) and δ-selinene synthase (SEQ ID No:20) cannot be responsible for the wound-induced production of E-α-bisabolene and δ-cadinene.

The ability of terpene synthases to produce multiple products has been well documented (Munck, S. L. & Croteau, R. (1990) *Arch. Biochem. Biophys.* 282, 58–64; Savage, T. J., et al., (1994) *J. Biol. Chem.* 269, 4012–4020; Lewinsohn, E., et al., (1992) *Arch. Biochem. Biophys.* 293, 167–173; Savage, T. J., et al., (1995) *Arch. Biochem. Biophys.* 320, 257–265; Wagschal, K., et al., (1991) Tetrahedron 47, 5933–5944) and may be a consequence of the unusual electrophilic reaction mechanisms employed by this enzyme type (Gershenzon, J. & Croteau, R. (1993) in *Lipid Metabolism in Plants* (Moore, Jr., T. S., ed) pp 340–388, CRC Press, Boca Raton, Fla.; Cane, D. E. (1992) in *Secondary Metabolites: Their Function and Evolution* (Chadwick, D. J. & Whelan, J., eds) pp 163–183, Ciba Foundation Symposium 171, John Wiley and Sons, West Sussex, UK; Croteau. R. (1987) *Chem. Rev.* 87, 929–954) that may also represent an evolutionary adaptation for the production of the maximum number of terpene products using the minimum genetic and enzymatic machinery (Langenheim. J. H. (1994) *J. Chem. Ecol.* 20, 1223–1280). Nevertheless, the production of 34 different sesquiterpenes by δ-selinene synthase (SEQ ID No:20) and 52 discrete sesquiterpenes by γ-humulene synthase (SEQ ID No:24), by variations upon several different cyclization routes, is quite remarkable. The reaction cascade catalyzed by γ-humulene synthase (SEQ ID No:24) is particularly complex in generating (by deprotonation) stable olefinic end-products corresponding to many of the proposed carbocationic intermediates of each cyclization route (see, Steele et al. *J. Biol. Chem.* 273: 2078–2089(1998)).

EXAMPLE 11

Additional Representative Nucleic Acid Sequences Encoding E-α-bisabolene synthase, δ-selinene synthase and γ-humulene synthase In addition to the nucleic acid sequence set forth in SEQ ID No:12, examples of representative nucleic acid sequences of the present invention that encode an E-α-bisabolene synthase protein are set forth in SEQ ID No:37, SEQ ID No:39 and SEQ ID No:41. The nucleic acid sequences set forth in SEQ ID No:39 and SEQ ID No:41 were generated using a computer and encode E-α-bisabolene synthase protein sequences, set forth in SEQ ID No:40 and SEQ ID No:42, having conservative amino acid substitutions relative to the E-α-bisabolene synthase protein sequence set forth in SEQ ID No:13.

The cDNA set forth in SEQ ID No:37 was isolated in the same way as cDNA AG1 (SEQ ID No:12) encoding E-α-bisabolene synthase from Grand fir. The cDNA set forth in SEQ ID No:37 differs from cDNA AG1 (SEQ ID No:12) by one nucleotide at position 194 (a "C" in AG1 (SEQ ID No:12) compared to a "T" in the sequence set forth in SEQ ID No:37). Consequently, the protein E-α-bisabolene synthase sequence set forth in SEQ ID No:13, encoded by AG1 (SEQ ID No:12) includes an alanine residue at position 65, whereas the protein sequence set forth in SEQ ID No:38, encoded by the nucleic acid sequence set forth in SEQ ID No:37, includes a valine residue at position number 65. The sequence set forth in SEQ ID No:37 is presently believed to be the correct sequence of a Grand fir E-α-bisabolene synthase cDNA, while the sequence set forth in SEQ ID No:12 is believed to be the result of a cloning artifact resulting in a "T" to "C" substitution at position 194. Nonetheless, both of the proteins set forth in SEQ ID No:13 and SEQ ID No:38 are functional E-α-bisabolene synthase proteins.

In addition to the nucleic acid sequence set forth in SEQ ID No:19, examples of representative nucleic acid sequences of the present invention that encode a δ-selinene synthase protein are set forth in SEQ ID No:43, SEQ ID No:45 and SEQ ID No:47. The nucleic acid sequences set forth in SEQ ID No:43; SEQ ID No:45 and SEQ ID No:47 were generated using a computer and encode δ-selinene synthase protein sequences, set forth in SEQ ID No:44, SEQ ID No:46 and SEQ ID No:48, having conservative amino acid substitutions relative to the δ-selinene synthase protein sequence set forth in SEQ ID No:20.

In addition to the nucleic acid sequence set forth in SEQ ID No:23, examples of representative nucleic acid sequences of the present invention that encode a γ-humulene synthase protein are set forth in SEQ ID No:49, SEQ ID No:51 and SEQ ID No:53. The nucleic acid sequences set forth in SEQ ID No:49; SEQ ID No:51 and SEQ ID No:53 were generated using a computer and encode γ-humulene synthase protein'sequences, set forth in SEQ ID No:50, SEQ ID No:52 and SEQ ID No:54, having conservative amino acid substitutions relative to the γ-humulene synthase protein sequence set forth in SEQ ID No:24.

EXAMPLE 12

Hybridization of Grand Fir (*Abies grandis*) E-α-bisabolene Synthase cDNA (SEQ ID NO:12), d-Selinene Synthase cDNA (SEQ ID No:19) and g-Humulene Synthase cDNA (SEQ ID No:23) to Other Nucleic Acid Sequences of the Present Invention The nucleic acid molecules of the present invention that encode an E-α-bisabolene synthase protein, a δ-selinene synthase protein or a γ-humulene synthase protein are preferably capable of hybridizing to the nucleic acid sequence set forth in SEQ ID NO:12, SEQ ID No:19 or SEQ ID No:23, respectively, or to the complementary sequence of the nucleic acid sequence set forth in SEQ ID NO:12, SEQ ID No:19 or SEQ ID No:23, respectively, under the following stringent hybridization conditions: incubation in 3×SSC at 65° C. for 16 hours, followed by washing under the following conditions: two washes in 2×SSC at 18° C. to 25° C. for twenty minutes per wash, followed by one wash in 0.5×SSC at 55° C. for thirty minutes.

Utilizing the foregoing hybridization and wash conditions, the E-α-bisabolene synthase cDNA molecule, having the nucleic acid sequence set forth in SEQ ID No:12, was used to probe a Northern blot bearing RNA samples from the following plant species: Grand fir (*Abies grandis*), White fir (*Abies concolor*), Western larch (*Larix occicientalis*), Colorado blue spruce (*Picea pungens*), Lodgepole pine (*Pinus contorta*), Loblolly pine (*Pinus taeda*) and Douglas fir (*Pseudotsuga menziesii*). RNA was isolated from two to five year-old saplings according to the method disclosed in Lewinsohn et al., Plant Mol. Biol. Rep. 21:20–25 (1994), incorporated herein by reference. The radiolabelled cDNA probe (SEQ ID No:12) hybridized to an RNA band of approximately 2.5 kilobases in all of the foregoing RNA samples.

The foregoing RNA samples were probed with the cDNA molecules having the nucleic acid sequences set forth in SEQ ID No:19 and SEQ ID No:23, encoding Grand fir δ-selinene synthase and γ-humulene synthase, respectively. The hybridization and wash conditions were as set forth in the foregoing description of the hybridization experiment utilizing the E-α-bisabolene synthase cDNA molecule, having the nucleic acid sequence set forth in SEQ ID No:12, as probe. The δ-selinene synthase nucleic acid probe (SEQ ID No:19) hybridized to an RNA band of approximately 1.8 kilobases in all of the foregoing RNA samples. The γ-humulene synthase nucleic acid probe (SEQ ID No:23) hybridized to an RNA band of approximately 1.8 kilobases in all of the foregoing RNA samples.

The ability of the nucleic acid molecules of the present invention to hybridize to one or more of the nucleic acid sequences set forth in SEQ ID NO:12, SEQ ID NO:19 or SEQ ID NO:23, or to their complementary sequences, can be determined utilizing any standard nucleic acid hybridization technique including, for example, the technique set forth at pages 9.52 to 9.55 of Molecular Cloning, A Laboratory Manual (2nd edition), J. Sambrook, E. F. Fritsch and T. Maniatis eds, the cited pages of which are incorporated herein by reference.

EXAMPLE 13

Properties of the E-α-Bisabolene Synthase Proteins, δ-Selinene Synthase Proteins and γ-Humulene Synthase Proteins of the Present Invention Representative E-α-bisabolene synthase proteins, δ-selinene synthase proteins and γ-humulene synthase proteins of the present invention preferably possess the following properties. Each of the three types of sesquiterpene synthases (E-α-bisabolene synthases, δ-selinene synthases and γ-humulene synthases) preferably has a requirement for divalent cations, such as $Mg^{++}$ or $Mn^{++}$ for catalysis and each preferably has an optimal catalytic activity within the range of from about pH 6.5 to about pH 7.5. The preferred substrate for each of the three types of sesquiterpene synthases is farnesyl diphosphate, but each can also utilize geranyl diphosphate as an adventitious substrate. Preferably each of the three types of sesquiterpene synthases lacks an amino-terminal plastidial targeting sequence, each preferably has a pI in the range of from about 4.5 to about 6.0 and each preferably includes at least one XXDDXXD (SEQ ID No:55) motif where each X residue represents a hydrophobic amino acid and D is an aspartate residue that functions in the coordination of the divalent cation. Further, each of the three types of sesquiterpene synthases preferably includes an arginine residue within the first 25 amino acids of the amino terminus that functions in ionization and/or isomerization of the substrate.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated, recombinant, gymnosperm E-α-bisabolene synthase protein consisting of the amino acid sequence set forth in SEQ ID No:13.

* * * * *

SEQUENCE LISTING

<160> NUMBER OF SEQ ID NOS: 55

<210> SEQ ID NO 1
<211> LENGTH: 2424
<212> TYPE: DNA
<213> ORGANISM: Abies grandis

<400> SEQUENCE: 1

```
gggttatgat cttgtgcatt ctcttaaatc accttatatt gattctagtt acagagaacg      60
cgcggaggtc cttgttagcg agattaaagt gatgcttaat ccagctatta caggagatgg     120
agaatcaatg attactccat ctgcttatga cacagcatgg gtagcgaggg tgcccgccat     180
tgatggctct gctcgcccgc aatttcccca aacagttgac tggattttga aaaccagtt     240 aaaagatggt tcatggggaa ttcagtccca ctttctgctg tccgaccgtc ttcttgccac     300
tctttcttgt gttcttgtgc tccttaaatg gaacgttggg gatctgcaag tagagcaggg     360
aattgaattc ataaagagca atctggaact agtaaaggat gaaaccgatc aagatagctt     420
```

```
ggtaacagac tttgagatca tatttccttc tctgttaaga aagctcaat ctctgcgcct    480 cggacttccc tacgacctgc cttatataca tctgttgcag actaaacggc aggaaagatt    540
agcaaaactt tcaagggagg aaatttatgc ggttccgtcg ccattgttgt attctttaga    600
gggaatacaa gatatagttg aatgggaacg aataatggaa gttcaaagtc aggatgggtc    660
tttcttaagc tcacctgctt ctactgcctg cgttttcatg cacacaggag acgcgaaatg    720
ccttgaattc ttgaacagtg tgatgatcaa gtttggaaat tttgttccct gcctgtatcc    780
tgtggatctg ctgaacgcc tgttgatcgt agataatatt gtacgccttg aatctatag    840 acactttgaa aaggaaatca aggaagctct tgattatgtt tacaggcatt ggaacgaaag    900
aggaattggg tggggcagac taaatcccat agcagatctt gagaccactg ctttgggatt    960
tcgattgctt cggctgcata ggtacaatgt atctccagcc attttgaca acttcaaaga    1020 tgccaatggg aaattcattt gctcgaccgg tcaattcaac aaagatgtag caagcatgct    1080
gaatctttat agagcttccc agctcgcatt tcccggagaa acattcttg atgaagctaa    1140 aagcttcgct actaaatatt tgagagaagc tcttgagaaa agtgagactt ccagtgcatg    1200
gaacaacaaa caaaacctga gccaagagat caaatacgcg ctgaagactt cttggcatgc    1260
cagtgttccg agagtggaag caagagagata ctgtcaagtg tatcgcccag attatgcacg    1320
catagcaaaa tgcgtttaca agctacccta cgtgaacaat gaaaagtttt tagagctggg    1380
aaaattagat ttcaacatta tccagtccat ccaccaagaa gaaatgaaga atgttaccag    1440
ctggtttaga gattcggggt tgccactatt caccttcgct cgggagaggc cgctggaatt    1500
ctacttctta gtagcggcgg ggacctatga accccagtat gccaaatgca ggttcctctt    1560
tacaaaagtg gcatgcttgc agactgttct ggacgatatg tatgacactt atggaaccct    1620
agatgaattg aagctattca ctgaggctgt gagaagatgg gacctctcct ttacagaaaa    1680
ccttccagac tatatgaaac tatgttacca aatctattat gacatagttc acgaggtggc    1740
ttgggaggca gagaaggaac aggggcgtga attggtcagc ttttcagaa agggatggga    1800 ggattatctt ctgggttatt atgaagaagc tgaatggtta gctgctgagt atgtgcctac    1860
cttggacgag tacataaaga atggaatcac atcatcggc caacgtatac ttctgttgag    1920
tggagtgttg ataatggatg ggcaactcct ttcgcaagag gcattagaga agtagatta    1980 tccaggaaga cgtgttctca cagagctgaa tagcctcatt tcccgcctgg cggatgacac    2040
gaagacatat aaagctgaga aggctcgtgg agaattggcg tccagcattg aatgttacat    2100
gaaagaccat cctgaatgta cagaggaaga ggctctcgat cacatctata gcattctgga    2160
gccggcggtg aaggaactga caagagagtt tctgaagccc gacgacgtcc cattcgcctg    2220
caagaagatg cttttcgagg agacaagagt gacgatggtg atattcaagg atggagatgg    2280
attcggtgtt tccaaattag aagtcaaaga tcatatcaaa gagtgtctca ttgaaccgct    2340
gccactgtaa tcaaaatagt tgcaataata attgaaataa tgtcaactat gtttcacaaa    2400
aaaaaaaaaa aaaaaaaaaa aaaa                                          2424
```

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: PCR
    primer C
<221> NAME/KEY: misc_feature
<222> LOCATION: (1)..(32)

```
<223> OTHER INFORMATION: PCR primer C wherein n at positions 21, 24,
      27 and 30 represents a, c, g or t

<400> SEQUENCE: 2
cgtctagayt kcatrtartc nggnarnykn tc                               32

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR
      primer D
<221> NAME/KEY: misc_feature
<222> LOCATION: (1)..(21)
<223> OTHER INFORMATION: PCR primer D wherein n at positions 7, 8, 9
      and 18 each represent a, c, g or t

<400> SEQUENCE: 3
gaygaynnnt wygaygcnya y                                           21

<210> SEQ ID NO 4
<211> LENGTH: 108
<212> TYPE: DNA
<213> ORGANISM: Abies grandis

<400> SEQUENCE: 4
tttcatgtaa tcggggaagt tgtctgtaaa ggagaggtcc catcttctca cagcctcagt    60
gaatagcttc aattcatcta gggttccgtg cgcatcaaac ccatcatc               108

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(44)
<223> OTHER INFORMATION: Marathon oligonucleotide adaptor

<400> SEQUENCE: 5
ctaatacgac tcactatagg gctcgagcgg ccgcccgggc aggt                   44

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
       oligonucleotide
<221> NAME/KEY: misc_feature
<222> LOCATION: (1)..(27)
<223> OTHER INFORMATION: PCR primer AP1

<400> SEQUENCE: 6
ccatcctaat acgactcact atagggc                                     27

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
        oligonucleotide
<221> NAME/KEY: misc_feature
<222> LOCATION: (1)..(25)
<223> OTHER INFORMATION: oligonucleotide primer RJ1
```

<400> SEQUENCE: 7
agacggtcgg acagcagaaa gtggg                                  25

<210> SEQ ID NO 8
<211> LENGTH: 404
<212> TYPE: DNA
<213> ORGANISM: Abies grandis

<400> SEQUENCE: 8
cttggatcca tggctggcgt ttctgctgta tcaaaggttt ccagcttggt ttgtgatttg     60
tcgagtacca gcggcttgat tcgaagaact gccaatcctc atcccaatgt ctggggttat    120
gatcttgtgc attctcttaa atcaccttat attgattcta gttacagaga acgcgcggag    180
gtccttgtta gcgagattaa agcgatgctt aatccagcta ttacaggaga tggagaatca    240
atgattactc catctgctta tgacacagca tgggtagcga gggtgcccgc cattgatggc    300
tctgctcgcc cgcaatttcc ccaaacagtt gactggattt tgaaaaacca gttaaaagat    360
ggttcatggg gaattcagtc ccactttctg ctgtccgacc gtct                    404

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: oligonucleotide primer RJ2

<400> SEQUENCE: 9
cttggatcca tggctggcgt ttctgctg                               28

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(39)
<223> OTHER INFORMATION: Oligonucleotide primer F

<400> SEQUENCE: 10
gttgcaataa taattgaaat aatctcaact atgtttcac                   39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(39)
<223> OTHER INFORMATION: oligonucleotide primer R

<400> SEQUENCE: 11
gtgaaacata gttgagatta tttcaattat tattgcaac                   39

<210> SEQ ID NO 12
<211> LENGTH: 2571
<212> TYPE: DNA

-continued

<213> ORGANISM: Abies grandis
<220> FEATURE:
<221> NAME/KEY: CDS
<222> LOCATION: (45)..(2495)

<400> SEQUENCE: 12

```
gtggcgacca tcctccaaaa tcggatctgg ttccgcgtgg atcc atg gct ggc gtt        56
                                                Met Ala Gly Val
                                                 1 tct gct gta tca aag gtt tcc agc ttg gtt tgt gat ttg tcg agt acc        104
Ser Ala Val Ser Lys Val Ser Ser Leu Val Cys Asp Leu Ser Ser Thr
  5              10                  15                  20 agc ggc ttg att cga aga act gcc aat cct cat ccc aat gtc tgg ggt        152
Ser Gly Leu Ile Arg Arg Thr Ala Asn Pro His Pro Asn Val Trp Gly
             25                  30                  35 tat gat ctt gtg cat tct ctt aaa tca cct tat att gat tct agt tac        200
Tyr Asp Leu Val His Ser Leu Lys Ser Pro Tyr Ile Asp Ser Ser Tyr
 40                  45                  50 aga gaa cgc gcg gag gtc ctt gtt agc gag att aaa gcg atg ctt aat        248
Arg Glu Arg Ala Glu Val Leu Val Ser Glu Ile Lys Ala Met Leu Asn
         55                  60                  65 cca gct att aca gga gat gga gaa tca atg att act cca tct gct tat        296
Pro Ala Ile Thr Gly Asp Gly Glu Ser Met Ile Thr Pro Ser Ala Tyr
 70                  75                  80 gac aca gca tgg gta gcg agg gtg ccc gcc att gat ggc tct gct cgc        344
Asp Thr Ala Trp Val Ala Arg Val Pro Ala Ile Asp Gly Ser Ala Arg
 85                  90                  95                 100 ccg caa ttt ccc caa aca gtt gac tgg att ttg aaa aac cag tta aaa        392
Pro Gln Phe Pro Gln Thr Val Asp Trp Ile Leu Lys Asn Gln Leu Lys
                105                 110                 115 gat ggt tca tgg gga att cag tcc cac ttt ctg ctg tcc gac cgt ctt        440
Asp Gly Ser Trp Gly Ile Gln Ser His Phe Leu Leu Ser Asp Arg Leu
            120                 125                 130 ctt gcc act ctt tct tgt gtt ctt gtg ctc ctt aaa tgg aac gtt ggg        488
Leu Ala Thr Leu Ser Cys Val Leu Val Leu Leu Lys Trp Asn Val Gly
        135                 140                 145 gat ctg caa gta gag cag gga att gaa ttc ata aag agc aat ctg gaa        536
Asp Leu Gln Val Glu Gln Gly Ile Glu Phe Ile Lys Ser Asn Leu Glu
    150                 155                 160 cta gta aag gat gaa acc gat caa gat agc ttg gta aca gac ttt gag        584
Leu Val Lys Asp Glu Thr Asp Gln Asp Ser Leu Val Thr Asp Phe Glu
165                 170                 175                 180 atc ata ttt cct tct ctg tta aga gaa gct caa tct ctg cgc ctc gga        632
Ile Ile Phe Pro Ser Leu Leu Arg Glu Ala Gln Ser Leu Arg Leu Gly
                185                 190                 195 ctt ccc tac gac ctg cct tat ata cat ctg ttg cag act aaa cgg cag        680
Leu Pro Tyr Asp Leu Pro Tyr Ile His Leu Leu Gln Thr Lys Arg Gln
            200                 205                 210 gaa aga tta gca aaa ctt tca agg gag gaa att tat gcg gtt ccg tcg        728
Glu Arg Leu Ala Lys Leu Ser Arg Glu Glu Ile Tyr Ala Val Pro Ser
        215                 220                 225 cca ttg ttg tat tct tta gag gga ata caa gat ata gtt gaa tgg gaa        776
Pro Leu Leu Tyr Ser Leu Glu Gly Ile Gln Asp Ile Val Glu Trp Glu
    230                 235                 240 cga ata atg gaa gtt caa agt cag gat ggg tct ttc tta agc tca cct        824
Arg Ile Met Glu Val Gln Ser Gln Asp Gly Ser Phe Leu Ser Ser Pro
245                 250                 255                 260 gct tct act gcc tgc gtt ttc atg cac aca gga gac gcg aaa tgc ctt        872
Ala Ser Thr Ala Cys Val Phe Met His Thr Gly Asp Ala Lys Cys Leu
                265                 270                 275
```

-continued

| | |
|---|---|
| gaa ttc ttg aac agt gtg atg atc aag ttt gga aat ttt gtt ccc tgc<br>Glu Phe Leu Asn Ser Val Met Ile Lys Phe Gly Asn Phe Val Pro Cys<br>280 285 290 | 920 |
| ctg tat cct gtg gat ctg ctg gaa cgc ctg ttg atc gta gat aat att<br>Leu Tyr Pro Val Asp Leu Leu Glu Arg Leu Leu Ile Val Asp Asn Ile<br>295 300 305 | 968 |
| gta cgc ctt gga atc tat aga cac ttt gaa aag gaa atc aag gaa gct<br>Val Arg Leu Gly Ile Tyr Arg His Phe Glu Lys Glu Ile Lys Glu Ala<br>310 315 320 | 1016 |
| ctt gat tat gtt tac agg cat tgg aac gaa aga gga att ggg tgg ggc<br>Leu Asp Tyr Val Tyr Arg His Trp Asn Glu Arg Gly Ile Gly Trp Gly<br>325 330 335 340 | 1064 |
| aga cta aat ccc ata gca gat ctt gag acc act gct ttg gga ttt cga<br>Arg Leu Asn Pro Ile Ala Asp Leu Glu Thr Thr Ala Leu Gly Phe Arg<br>345 350 355 | 1112 |
| ttg ctt cgg ctg cat agg tac aat gta tct cca gcc att ttt gac aac<br>Leu Leu Arg Leu His Arg Tyr Asn Val Ser Pro Ala Ile Phe Asp Asn<br>360 365 370 | 1160 |
| ttc aaa gat gcc aat ggg aaa ttc att tgc tcg acc ggt caa ttc aac<br>Phe Lys Asp Ala Asn Gly Lys Phe Ile Cys Ser Thr Gly Gln Phe Asn<br>375 380 385 | 1208 |
| aaa gat gta gca agc atg ctg aat ctt tat aga gct tcc cag ctc gca<br>Lys Asp Val Ala Ser Met Leu Asn Leu Tyr Arg Ala Ser Gln Leu Ala<br>390 395 400 | 1256 |
| ttt ccc gga gaa aac att ctt gat gaa gct aaa agc ttc gct act aaa<br>Phe Pro Gly Glu Asn Ile Leu Asp Glu Ala Lys Ser Phe Ala Thr Lys<br>405 410 415 420 | 1304 |
| tat ttg aga gaa gct ctt gag aaa agt gag act tcc agt gca tgg aac<br>Tyr Leu Arg Glu Ala Leu Glu Lys Ser Glu Thr Ser Ser Ala Trp Asn<br>425 430 435 | 1352 |
| aac aaa caa aac ctg agc caa gag atc aaa tac gcg ctg aag act tct<br>Asn Lys Gln Asn Leu Ser Gln Glu Ile Lys Tyr Ala Leu Lys Thr Ser<br>440 445 450 | 1400 |
| tgg cat gcc agt gtt ccg aga gtg gaa gca aag aga tac tgt caa gtg<br>Trp His Ala Ser Val Pro Arg Val Glu Ala Lys Arg Tyr Cys Gln Val<br>455 460 465 | 1448 |
| tat cgc cca gat tat gca cgc ata gca aaa tgc gtt tac aag cta ccc<br>Tyr Arg Pro Asp Tyr Ala Arg Ile Ala Lys Cys Val Tyr Lys Leu Pro<br>470 475 480 | 1496 |
| tac gtg aac aat gaa aag ttt tta gag ctg gga aaa tta gat ttc aac<br>Tyr Val Asn Asn Glu Lys Phe Leu Glu Leu Gly Lys Leu Asp Phe Asn<br>485 490 495 500 | 1544 |
| att atc cag tcc atc cac caa gaa gaa atg aag aat gtt acc agc tgg<br>Ile Ile Gln Ser Ile His Gln Glu Glu Met Lys Asn Val Thr Ser Trp<br>505 510 515 | 1592 |
| ttt aga gat tcg ggg ttg cca cta ttc acc ttc gct cgg gag agg ccg<br>Phe Arg Asp Ser Gly Leu Pro Leu Phe Thr Phe Ala Arg Glu Arg Pro<br>520 525 530 | 1640 |
| ctg gaa ttc tac ttc tta gta gcg gcg ggg acc tat gaa ccc cag tat<br>Leu Glu Phe Tyr Phe Leu Val Ala Ala Gly Thr Tyr Glu Pro Gln Tyr<br>535 540 545 | 1688 |
| gcc aaa tgc agg ttc ctc ttt aca aaa gtg gca tgc ttg cag act gtt<br>Ala Lys Cys Arg Phe Leu Phe Thr Lys Val Ala Cys Leu Gln Thr Val<br>550 555 560 | 1736 |
| ctg gac gat atg tat gac act tat gga acc cta gat gaa ttg aag cta<br>Leu Asp Asp Met Tyr Asp Thr Tyr Gly Thr Leu Asp Glu Leu Lys Leu<br>565 570 575 580 | 1784 |
| ttc act gag gct gtg aga aga tgg gac ctc tcc ttt aca gaa aac ctt<br>Phe Thr Glu Ala Val Arg Arg Trp Asp Leu Ser Phe Thr Glu Asn Leu<br>585 590 595 | 1832 |

```
cca gac tat atg aaa cta tgt tac caa atc tat tat gac ata gtt cac    1880
Pro Asp Tyr Met Lys Leu Cys Tyr Gln Ile Tyr Tyr Asp Ile Val His
            600                 605                 610 gag gtg gct tgg gag gca gag aag gaa cag ggg cgt gaa ttg gtc agc    1928
Glu Val Ala Trp Glu Ala Glu Lys Glu Gln Gly Arg Glu Leu Val Ser
    615                 620                 625 ttt ttc aga aag gga tgg gag gat tat ctt ctg ggt tat tat gaa gaa    1976
Phe Phe Arg Lys Gly Trp Glu Asp Tyr Leu Leu Gly Tyr Tyr Glu Glu
630                 635                 640 gct gaa tgg tta gct gct gag tat gtg cct acc ttg gac gag tac ata    2024
Ala Glu Trp Leu Ala Ala Glu Tyr Val Pro Thr Leu Asp Glu Tyr Ile
645                 650                 655                 660 aag aat gga atc aca tct atc ggc caa cgt ata ctt ctg ttg agt gga    2072
Lys Asn Gly Ile Thr Ser Ile Gly Gln Arg Ile Leu Leu Leu Ser Gly
            665                 670                 675 gtg ttg ata atg gat ggg caa ctc ctt tcg caa gag gca tta gag aaa    2120
Val Leu Ile Met Asp Gly Gln Leu Leu Ser Gln Glu Ala Leu Glu Lys
        680                 685                 690 gta gat tat cca gga aga cgt gtt ctc aca gag ctg aat agc ctc att    2168
Val Asp Tyr Pro Gly Arg Arg Val Leu Thr Glu Leu Asn Ser Leu Ile
    695                 700                 705 tcc cgc ctg gcg gat gac acg aag aca tat aaa gct gag aag gct cgt    2216
Ser Arg Leu Ala Asp Asp Thr Lys Thr Tyr Lys Ala Glu Lys Ala Arg
710                 715                 720 gga gaa ttg gcg tcc agc att gaa tgt tac atg aaa gac cat cct gaa    2264
Gly Glu Leu Ala Ser Ser Ile Glu Cys Tyr Met Lys Asp His Pro Glu
725                 730                 735                 740 tgt aca gag gaa gag gct ctc gat cac atc tat agc att ctg gag ccg    2312
Cys Thr Glu Glu Glu Ala Leu Asp His Ile Tyr Ser Ile Leu Glu Pro
            745                 750                 755 gcg gtg aag gaa ctg aca aga gag ttt ctg aag ccc gac gac gtc cca    2360
Ala Val Lys Glu Leu Thr Arg Glu Phe Leu Lys Pro Asp Asp Val Pro
        760                 765                 770 ttc gcc tgc aag aag atg ctt ttc gag gag aca aga gtg acg atg gtg    2408
Phe Ala Cys Lys Lys Met Leu Phe Glu Glu Thr Arg Val Thr Met Val
    775                 780                 785 ata ttc aag gat gga gat gga ttc ggt gtt tcc aaa tta gaa gtc aaa    2456
Ile Phe Lys Asp Gly Asp Gly Phe Gly Val Ser Lys Leu Glu Val Lys
790                 795                 800 gat cat atc aaa gag tgt ctc att gaa ccg ctg cca ctg taatcaaat     2505
Asp His Ile Lys Glu Cys Leu Ile Glu Pro Leu Pro Leu
805                 810                 815 agttgcaata ataattgaaa taatctcaac tatgtttcac aaaaaaaaaa aaaaaaaaa   2565 aaaaaa                                                             2571

<210> SEQ ID NO 13
<211> LENGTH: 817
<212> TYPE: PRT
<213> ORGANISM: Abies grandis

<400> SEQUENCE: 13

Met Ala Gly Val Ser Ala Val Ser Lys Val Ser Ser Leu Val Cys Asp
 1               5                  10                  15

Leu Ser Ser Thr Ser Gly Leu Ile Arg Arg Thr Ala Asn Pro His Pro
            20                  25                  30

Asn Val Trp Gly Tyr Asp Leu Val His Ser Leu Lys Ser Pro Tyr Ile
        35                  40                  45

Asp Ser Ser Tyr Arg Glu Arg Ala Glu Val Leu Val Ser Glu Ile Lys
```

```
           50                  55                  60
Ala Met Leu Asn Pro Ala Ile Thr Gly Asp Gly Glu Ser Met Ile Thr
 65                  70                  75                  80

Pro Ser Ala Tyr Asp Thr Ala Trp Val Ala Arg Val Pro Ala Ile Asp
                 85                  90                  95

Gly Ser Ala Arg Pro Gln Phe Pro Gln Thr Val Asp Trp Ile Leu Lys
                100                 105                 110

Asn Gln Leu Lys Asp Gly Ser Trp Gly Ile Gln Ser His Phe Leu Leu
                115                 120                 125

Ser Asp Arg Leu Leu Ala Thr Leu Ser Cys Val Leu Val Leu Leu Lys
                130                 135                 140

Trp Asn Val Gly Asp Leu Gln Val Glu Gln Gly Ile Glu Phe Ile Lys
145                 150                 155                 160

Ser Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
                180                 185                 190

Leu Arg Leu Gly Leu Pro Tyr Asp Leu Pro Tyr Ile His Leu Leu Gln
                195                 200                 205

Thr Lys Arg Gln Glu Arg Leu Ala Lys Leu Ser Arg Glu Glu Ile Tyr
                210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
                245                 250                 255

Leu Ser Ser Pro Ala Ser Thr Ala Cys Val Phe Met His Thr Gly Asp
                260                 265                 270

Ala Lys Cys Leu Glu Phe Leu Asn Ser Val Met Ile Lys Phe Gly Asn
                275                 280                 285

Phe Val Pro Cys Leu Tyr Pro Val Asp Leu Leu Glu Arg Leu Leu Ile
                290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
                325                 330                 335

Ile Gly Trp Gly Arg Leu Asn Pro Ile Ala Asp Leu Glu Thr Thr Ala
                340                 345                 350

Leu Gly Phe Arg Leu Leu Arg Leu His Arg Tyr Asn Val Ser Pro Ala
                355                 360                 365

Ile Phe Asp Asn Phe Lys Asp Ala Asn Gly Lys Phe Ile Cys Ser Thr
                370                 375                 380

Gly Gln Phe Asn Lys Asp Val Ala Ser Met Leu Asn Leu Tyr Arg Ala
385                 390                 395                 400

Ser Gln Leu Ala Phe Pro Gly Glu Asn Ile Leu Asp Glu Ala Lys Ser
                405                 410                 415

Phe Ala Thr Lys Tyr Leu Arg Glu Ala Leu Glu Lys Ser Glu Thr Ser
                420                 425                 430

Ser Ala Trp Asn Asn Lys Gln Asn Leu Ser Gln Glu Ile Lys Tyr Ala
                435                 440                 445

Leu Lys Thr Ser Trp His Ala Ser Val Pro Arg Val Glu Ala Lys Arg
                450                 455                 460

Tyr Cys Gln Val Tyr Arg Pro Asp Tyr Ala Arg Ile Ala Lys Cys Val
465                 470                 475                 480
```

-continued

Tyr Lys Leu Pro Tyr Val Asn Asn Glu Lys Phe Leu Glu Leu Gly Lys
            485                 490                 495
Leu Asp Phe Asn Ile Ile Gln Ser Ile His Gln Glu Glu Met Lys Asn
            500                 505                 510
Val Thr Ser Trp Phe Arg Asp Ser Gly Leu Pro Leu Phe Thr Phe Ala
            515                 520                 525
Arg Glu Arg Pro Leu Glu Phe Tyr Phe Leu Val Ala Ala Gly Thr Tyr
            530                 535                 540
Glu Pro Gln Tyr Ala Lys Cys Arg Phe Leu Phe Thr Lys Val Ala Cys
545                 550                 555                 560
Leu Gln Thr Val Leu Asp Asp Met Tyr Asp Thr Tyr Gly Thr Leu Asp
            565                 570                 575
Glu Leu Lys Leu Phe Thr Glu Ala Val Arg Arg Trp Asp Leu Ser Phe
            580                 585                 590
Thr Glu Asn Leu Pro Asp Tyr Met Lys Leu Cys Tyr Gln Ile Tyr Tyr
            595                 600                 605
Asp Ile Val His Glu Val Ala Trp Glu Ala Lys Glu Gln Gly Arg
            610                 615                 620
Glu Leu Val Ser Phe Phe Arg Lys Gly Trp Glu Asp Tyr Leu Leu Gly
625                 630                 635                 640
Tyr Tyr Glu Glu Ala Glu Trp Leu Ala Ala Glu Tyr Val Pro Thr Leu
            645                 650                 655
Asp Glu Tyr Ile Lys Asn Gly Ile Thr Ser Ile Gly Gln Arg Ile Leu
            660                 665                 670
Leu Leu Ser Gly Val Leu Ile Met Asp Gly Gln Leu Leu Ser Gln Glu
            675                 680                 685
Ala Leu Glu Lys Val Asp Tyr Pro Gly Arg Arg Val Leu Thr Glu Leu
            690                 695                 700
Asn Ser Leu Ile Ser Arg Leu Ala Asp Asp Thr Lys Thr Tyr Lys Ala
705                 710                 715                 720
Glu Lys Ala Arg Gly Glu Leu Ala Ser Ser Ile Glu Cys Tyr Met Lys
            725                 730                 735
Asp His Pro Glu Cys Thr Glu Glu Ala Leu Asp His Ile Tyr Ser
            740                 745                 750
Ile Leu Glu Pro Ala Val Lys Glu Leu Thr Arg Glu Phe Leu Lys Pro
            755                 760                 765
Asp Asp Val Pro Phe Ala Cys Lys Lys Met Leu Phe Glu Glu Thr Arg
            770                 775                 780
Val Thr Met Val Ile Phe Lys Asp Gly Asp Gly Phe Gly Val Ser Lys
785                 790                 795                 800
Leu Glu Val Lys Asp His Ile Lys Glu Cys Leu Ile Glu Pro Leu Pro
            805                 810                 815
Leu

<210> SEQ ID NO 14
<211> LENGTH: 1967
<212> TYPE: DNA
<213> ORGANISM: Abies grandis

<400> SEQUENCE: 14
tttctgaatc ttccatccct cgacgcacag ggaatcatca cggaaatgtg tgggacgatg      60
acctcataca ctctctcaac tcgccctatg gggcacctgc atattatgag ctccttcaaa     120
agcttattga ggagatcaag catttacttt tgactgaaat ggaaatggat gatggcgatc     180

```
atgatttaat caaacgtctt cagatcgttg acactttgga atgcctggga atcgatagac      240
attttgaaca cgaaatacaa acagctgctt tagattacgt ttacagatgg tggaacgaaa      300
aaggtatcgg ggagggatca agagattcct tcagcaaaga tctcaacgct acagctttag      360
gatttcgcgc tctccgactg catcgatata acgtatcgtc aggtgtgttg aagaatttca      420
aggatgaaaa cgggaagttc ttctgcaact ttactggtga agaaggaaga ggagataaac      480
aagtgagaag catgttgtcg ttacttcgag cttcagagat ttcgtttccc ggagaaaaag      540
tgatggaaga ggccaaggca ttcacaagag aatatctaaa ccaagtttta gctggacacg      600
gggatgtgac tgacgtggat caaagccttt tggagagagg tgaagtacgc attggagttt      660
ccatggcttg cagtgtgccg agatgggagg caaggagctt tctcgaaata tatggacaca      720
accattcgtg gctcaagtcg aatatcaacc aaaaaatgtt gaagttagcc aaattggact      780
tcaatattct gcaatgcaaa catcacaagg agatacagtt tattacaagg tggtggagag      840
actcgggtat atcgcagctg aatttctatc gaaagcgaca cgtggaatat tattcttggg      900
ttgttatgtg cattttgag ccagagttct ctgaaagtag aattgccttc gccaaaactg       960
ctatcctatg tactgttcta gatgacctct atgatacgca cgcaacgttg catgaaatca      1020
aaatcatgac agagggagtg agacgatggg atctttcgtt gacagatgac ctcccagact      1080
acattaaaat tgcattccag ttcttcttca atacagtgaa tgaattgata gttgaaatcg      1140
tgaaacggca agggcgggat atgacaacca tagttaaaga ttgctggaag cgatacattg      1200
agtcttatct gcaagaagcg gaatggatag caactggaca tattcccact tttaacgaat      1260
acataaagaa cggcatggct agctcaggga tgtgtattgt aaatttgaat ccacttctct      1320
tgttgggtaa acttctcccc gacaacattc tggagcaaat acattctcca tccaagatcc      1380
tggacctctt agaattgacg ggcagaatcg ccgatgactt aaaagatttc gaggacgaga      1440
aggaacgcgg ggagatggct tcatctttac agtgttatat gaaagaaaat cctgaatcta      1500
cagtggaaaa tgctttaaat cacataaaag gcatccttaa tcgttccctt gaggaattta      1560
attgggagtt tatgaagcag gatagtgtcc caatgtgttg caagaaattc actttcaata      1620
taggtcgagg acttcaattc atctacaaat acagagacgg cttatacatt tctgacaagg      1680
aagtaaagga ccagatattc aaaattctag tccaccaagt tccaatggag gaatagtgat      1740
ggtcttggtt gtagttgtct attatggtat attgcattga catttatgct taaaggtgtt      1800
tcttaaacgt ttagggcgga ccgttaaata agttggcaat aattaatatt tagagacttt      1860
gtggaagtgt ttagggcata aaattgccta tggcctatgg caagctacaa attgaaattg      1920
ttgtgtttat aatattttta ttttatttaa aaaaaaaaa aaaaaa                      1967
```

<210> SEQ ID NO 15
<211> LENGTH: 104
<212> TYPE: DNA
<213> ORGANISM: Abies grandis

<400> SEQUENCE: 15

```
tttcatatag tcggggaagc ggtcaacgaa agatcccatc gtctcactcc ctctgtcatg       60
attttgattt cttccaacgt tccgtacgca tcatacccat catc                       104
```

<210> SEQ ID NO 16
<211> LENGTH: 26
<212> TYPE: DNA
<213> ORGANISM: Artificial Sequence
<220> FEATURE:

```
<223> OTHER INFORMATION: Description of Artificial Sequence:
      oligonucleotide
<221> NAME/KEY: misc_feature
<222> LOCATION: (1)..(26)
<223> OTHER INFORMATION: Reverse RACE primer

<400> SEQUENCE: 16
ctgcgaacct tgagagtggt ctgcag                                        26

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(25)
<223> OTHER INFORMATION: 5' oligonucleotide RACE primer specific for
      ag4.30

<400> SEQUENCE: 17
ggaggatcca tggctgagat ttctg                                         25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(26)
<223> OTHER INFORMATION: 3' oligonucleotide RACE primer specific for ag
      4.30

<400> SEQUENCE: 18
aaagtctcga gatattaatt attgcc                                        26

<210> SEQ ID NO 19
<211> LENGTH: 1888
<212> TYPE: DNA
<213> ORGANISM: Abies grandis
<220> FEATURE:
<221> NAME/KEY: CDS
<222> LOCATION: (24)..(1766)

<400> SEQUENCE: 19
cggatctggt tccgcgtgga tcc atg gct gag att tct gaa tct tcc atc cct      53
                         Met Ala Glu Ile Ser Glu Ser Ser Ile Pro
                          1               5                  10 cga cgc aca ggg aat cat cac gga aat gtg tgg gac gat gac ctc ata      101
Arg Arg Thr Gly Asn His His Gly Asn Val Trp Asp Asp Asp Leu Ile
             15                  20                  25 cac tct ctc aac tcg ccc tat ggg gca cct gca tat tat gag ctc ctt      149
His Ser Leu Asn Ser Pro Tyr Gly Ala Pro Ala Tyr Tyr Glu Leu Leu
         30                  35                  40 caa aag ctt att cag gag atc aag cat tta ctt ttg act gaa atg gaa      197
Gln Lys Leu Ile Gln Glu Ile Lys His Leu Leu Leu Thr Glu Met Glu
     45                  50                  55 atg gat gat ggc gat cat gat tta atc aaa cgt ctt cag atc gtt gac      245
Met Asp Asp Gly Asp His Asp Leu Ile Lys Arg Leu Gln Ile Val Asp
 60                  65                  70 act ttg gaa tgc ctg gga atc gat aga cat ttt gaa cac gaa ata caa      293
Thr Leu Glu Cys Leu Gly Ile Asp Arg His Phe Glu His Glu Ile Gln
 75                  80                  85                  90
```

```
aca gct gct tta gat tac gtt tac aga tgg tgg aac gaa aaa ggt atc        341
Thr Ala Ala Leu Asp Tyr Val Tyr Arg Trp Trp Asn Glu Lys Gly Ile
            95                  100                 105 ggg gag gga tca aga gat tcc ttc agc aaa gat ctg aac gct acg gct        389
Gly Glu Gly Ser Arg Asp Ser Phe Ser Lys Asp Leu Asn Ala Thr Ala
        110                 115                 120 tta gga ttt cgc gct ctc cga ctg cat cga tat aac gta tcg tca ggt        437
Leu Gly Phe Arg Ala Leu Arg Leu His Arg Tyr Asn Val Ser Ser Gly
        125                 130                 135 gtg ttg aag aat ttc aag gat gaa aac ggg aag ttc ttc tgc aac ttt        485
Val Leu Lys Asn Phe Lys Asp Glu Asn Gly Lys Phe Phe Cys Asn Phe
    140                 145                 150 act ggt gaa gaa gga aga gga gat aaa caa gtg aga agc atg ttg tcg        533
Thr Gly Glu Glu Gly Arg Gly Asp Lys Gln Val Arg Ser Met Leu Ser
155                 160                 165                 170 tta ctt cga gct tca gag att tcg ttt ccc gga gaa aaa gtg atg gaa        581
Leu Leu Arg Ala Ser Glu Ile Ser Phe Pro Gly Glu Lys Val Met Glu
                175                 180                 185 gag gcc aag gca ttc aca aga gaa tat cta aac caa gtt tta gct gga        629
Glu Ala Lys Ala Phe Thr Arg Glu Tyr Leu Asn Gln Val Leu Ala Gly
        190                 195                 200 cac ggg gat gtg act gac gtg gat caa agc ctt ttg aga gag gtg aag        677
His Gly Asp Val Thr Asp Val Asp Gln Ser Leu Leu Arg Glu Val Lys
        205                 210                 215 tac gca ttg gag ttt cca tgg cat tgc agt gtg ccg aga tgg gag gca        725
Tyr Ala Leu Glu Phe Pro Trp His Cys Ser Val Pro Arg Trp Glu Ala
    220                 225                 230 agg agc ttt ctc gaa ata tat gga cac aac cat tcg tgg ctc aag tcg        773
Arg Ser Phe Leu Glu Ile Tyr Gly His Asn His Ser Trp Leu Lys Ser
235                 240                 245                 250 aat atc aac caa aaa atg ttg aag tta gcc aaa ttg gac ttc aat att        821
Asn Ile Asn Gln Lys Met Leu Lys Leu Ala Lys Leu Asp Phe Asn Ile
                255                 260                 265 ctg caa tgc aaa cat cac aag gag ata cag ttt att aca agg tgg tgg        869
Leu Gln Cys Lys His His Lys Glu Ile Gln Phe Ile Thr Arg Trp Trp
        270                 275                 280 aga gac tcg ggt ata tcg cag ctg aat ttc tat cga aag cga cac gtg        917
Arg Asp Ser Gly Ile Ser Gln Leu Asn Phe Tyr Arg Lys Arg His Val
        285                 290                 295 gaa tat tat tct tgg gtt gtt atg tgc att ttt gag cca gag ttc tct        965
Glu Tyr Tyr Ser Trp Val Val Met Cys Ile Phe Glu Pro Glu Phe Ser
    300                 305                 310 gaa agt aga att gcc ttc gcc aaa act gct atc ctg tgt act gtt cta       1013
Glu Ser Arg Ile Ala Phe Ala Lys Thr Ala Ile Leu Cys Thr Val Leu
315                 320                 325                 330 gat gac ctc tat gat acg cac gca aca ttg cat gaa atc aaa atc atg       1061
Asp Asp Leu Tyr Asp Thr His Ala Thr Leu His Glu Ile Lys Ile Met
                335                 340                 345 aca gag gga gtg aga cga tgg gat ctt tcg ttg aca gat gac ctc cca       1109
Thr Glu Gly Val Arg Arg Trp Asp Leu Ser Leu Thr Asp Asp Leu Pro
        350                 355                 360 gac tac att aaa att gca ttc cag ttc ttc ttc aat aca gtg aat gaa       1157
Asp Tyr Ile Lys Ile Ala Phe Gln Phe Phe Phe Asn Thr Val Asn Glu
        365                 370                 375 ttg ata gtt gaa atc gtg aaa cgg caa ggg cgg gat atg aca acc ata       1205
Leu Ile Val Glu Ile Val Lys Arg Gln Gly Arg Asp Met Thr Thr Ile
    380                 385                 390 gtt aaa gat tgc tgg aag cga tac att gag tct tat ctg caa gaa gcg       1253
Val Lys Asp Cys Trp Lys Arg Tyr Ile Glu Ser Tyr Leu Gln Glu Ala
395                 400                 405                 410
```

```
gaa tgg ata gca act gga cat att ccc act ttt aac gaa tac ata aag     1301
Glu Trp Ile Ala Thr Gly His Ile Pro Thr Phe Asn Glu Tyr Ile Lys
                415                 420                 425 aac ggc atg gct agc tca ggg atg tgt att cta aat ttg aat cca ctt     1349
Asn Gly Met Ala Ser Ser Gly Met Cys Ile Leu Asn Leu Asn Pro Leu
            430                 435                 440 ctc ttg ttg gat aaa ctt ctc ccc gac aac att ctg gag caa ata cat     1397
Leu Leu Leu Asp Lys Leu Leu Pro Asp Asn Ile Leu Glu Gln Ile His
        445                 450                 455 tct cca tcc aag atc ctg gac ctc tta gaa ttg acg ggc aga atc gcc     1445
Ser Pro Ser Lys Ile Leu Asp Leu Leu Glu Leu Thr Gly Arg Ile Ala
    460                 465                 470 gat gac tta aaa gat ttc gag gac gag aag gaa cgc ggg gag atg gct     1493
Asp Asp Leu Lys Asp Phe Glu Asp Glu Lys Glu Arg Gly Glu Met Ala
475                 480                 485                 490 tca tct tta cag tgt tat atg aaa gaa aat cct gaa tct aca gtg gaa     1541
Ser Ser Leu Gln Cys Tyr Met Lys Glu Asn Pro Glu Ser Thr Val Glu
                495                 500                 505 aat gct tta aat cac ata aaa ggc atc ctt aat cgt tcc ctt gag gaa     1589
Asn Ala Leu Asn His Ile Lys Gly Ile Leu Asn Arg Ser Leu Glu Glu
            510                 515                 520 ttt aat tgg gag ttt atg aag cag gat agt gtc cca atg tgt tgc aag     1637
Phe Asn Trp Glu Phe Met Lys Gln Asp Ser Val Pro Met Cys Cys Lys
        525                 530                 535 aaa ttc act ttc aat ata ggt cga gga ctt caa ttc atc tac aaa tac     1685
Lys Phe Thr Phe Asn Ile Gly Arg Gly Leu Gln Phe Ile Tyr Lys Tyr
    540                 545                 550 aga gac ggc tta tac att tct gac aag gaa gta aag gac cag ata ttc     1733
Arg Asp Gly Leu Tyr Ile Ser Asp Lys Glu Val Lys Asp Gln Ile Phe
555                 560                 565                 570 aaa att cta gtc cac caa gtt cca atg gag gaa tagtgatggt cttggttgta   1786
Lys Ile Leu Val His Gln Val Pro Met Glu Glu
                575                 580 gttgtctatt atggtatatt gcattgacat ttatgcttaa aggtgtttct taaacgttta   1846
gggcggaccg ttaaataagt tggcaataat taatatctcg ag                     1888

<210> SEQ ID NO 20
<211> LENGTH: 581
<212> TYPE: PRT
<213> ORGANISM: Abies grandis

<400> SEQUENCE: 20

Met Ala Glu Ile Ser Glu Ser Ser Ile Pro Arg Arg Thr Gly Asn His
 1               5                  10                  15

His Gly Asn Val Trp Asp Asp Leu Ile His Ser Leu Asn Ser Pro
             20                  25                  30

Tyr Gly Ala Pro Ala Tyr Tyr Glu Leu Leu Gln Lys Leu Ile Gln Glu
         35                  40                  45

Ile Lys His Leu Leu Thr Glu Met Glu Met Asp Asp Gly Asp His
     50                  55                  60

Asp Leu Ile Lys Arg Leu Gln Ile Val Asp Thr Leu Glu Cys Leu Gly
 65                  70                  75                  80

Ile Asp Arg His Phe Glu His Glu Ile Gln Thr Ala Ala Leu Asp Tyr
                 85                  90                  95

Val Tyr Arg Trp Trp Asn Glu Lys Gly Ile Gly Glu Gly Ser Arg Asp
            100                 105                 110

Ser Phe Ser Lys Asp Leu Asn Ala Thr Ala Leu Gly Phe Arg Ala Leu
```

-continued

```
            115                 120                 125
Arg Leu His Arg Tyr Asn Val Ser Ser Gly Val Leu Lys Asn Phe Lys
    130                 135                 140

Asp Glu Asn Gly Lys Phe Cys Asn Phe Thr Gly Glu Glu Gly Arg
145                 150                 155                 160

Gly Asp Lys Gln Val Arg Ser Met Leu Ser Leu Arg Ala Ser Glu
                165                 170                 175

Ile Ser Phe Pro Gly Lys Val Met Glu Glu Ala Lys Ala Phe Thr
                180                 185                 190

Arg Glu Tyr Leu Asn Gln Val Leu Ala Gly His Gly Asp Val Thr Asp
                195                 200                 205

Val Asp Gln Ser Leu Leu Arg Glu Val Lys Tyr Ala Leu Glu Phe Pro
    210                 215                 220

Trp His Cys Ser Val Pro Arg Trp Glu Ala Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
                260                 265                 270

Lys Glu Ile Gln Phe Ile Thr Arg Trp Trp Arg Asp Ser Gly Ile Ser
                275                 280                 285

Gln Leu Asn Phe Tyr Arg Lys Arg His Val Glu Tyr Tyr Ser Trp Val
    290                 295                 300

Val Met Cys Ile Phe Glu Pro Glu Phe Ser Glu Ser Arg Ile Ala Phe
305                 310                 315                 320

Ala Lys Thr Ala Ile Leu Cys Thr Val Leu Asp Asp Leu Tyr Asp Thr
                325                 330                 335

His Ala Thr Leu His Glu Ile Lys Ile Met Thr Glu Gly Val Arg Arg
                340                 345                 350

Trp Asp Leu Ser Leu Thr Asp Leu Pro Asp Tyr Ile Lys Ile Ala
                355                 360                 365

Phe Gln Phe Phe Asn Thr Val Asn Glu Leu Ile Val Glu Ile Val
    370                 375                 380

Lys Arg Gln Gly Arg Asp Met Thr Thr Ile Val Lys Asp Cys Trp Lys
385                 390                 395                 400

Arg Tyr Ile Glu Ser Tyr Leu Gln Glu Ala Glu Trp Ile Ala Thr Gly
                405                 410                 415

His Ile Pro Thr Phe Asn Glu Tyr Ile Lys Asn Gly Met Ala Ser Ser
                420                 425                 430

Gly Met Cys Ile Leu Asn Leu Asn Pro Leu Leu Leu Asp Lys Leu
                435                 440                 445

Leu Pro Asp Asn Ile Leu Glu Gln Ile His Ser Pro Ser Lys Ile Leu
    450                 455                 460

Asp Leu Leu Glu Leu Thr Gly Arg Ile Ala Asp Asp Leu Lys Asp Phe
465                 470                 475                 480

Glu Asp Glu Lys Glu Arg Gly Glu Met Ala Ser Ser Leu Gln Cys Tyr
                485                 490                 495

Met Lys Glu Asn Pro Glu Ser Thr Val Glu Asn Ala Leu Asn His Ile
                500                 505                 510

Lys Gly Ile Leu Asn Arg Ser Leu Glu Glu Phe Asn Trp Glu Phe Met
                515                 520                 525

Lys Gln Asp Ser Val Pro Met Cys Cys Lys Lys Phe Thr Phe Asn Ile
    530                 535                 540
```

-continued

```
Gly Arg Gly Leu Gln Phe Ile Tyr Lys Tyr Arg Asp Gly Leu Tyr Ile
545                 550                 555                 560

Ser Asp Lys Glu Val Lys Asp Gln Ile Phe Lys Ile Leu Val His Gln
                565                 570                 575

Val Pro Met Glu Glu
            580

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(28)
<223> OTHER INFORMATION: PCR oligonucleotide primer NdeI

<400> SEQUENCE: 21
ctggttccgc gtggacatat ggctgagt                                          28

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(33)
<223> OTHER INFORMATION: PCR oligonucleotide primer 4- BamHI

<400> SEQUENCE: 22
ctacaaccaa gaggatccct attcctccat tgg                                    33

<210> SEQ ID NO 23
<211> LENGTH: 1977
<212> TYPE: DNA
<213> ORGANISM: Abies grandis
<220> FEATURE:
<221> NAME/KEY: CDS
<222> LOCATION: (4)..(1782)

<400> SEQUENCE: 23 tcc atg gct cag att tct gaa tct gta tca ccc tct acc gat ttg aag         48
    Met Ala Gln Ile Ser Glu Ser Val Ser Pro Ser Thr Asp Leu Lys
    1               5                  10                  15 agc acc gaa tct tcc att acc tct aat cga cat gga aat atg tgg gag         96
Ser Thr Glu Ser Ser Ile Thr Ser Asn Arg His Gly Asn Met Trp Glu
                20                  25                  30 gac gat cgc ata cag tct ctc aac tca cct tat ggg gca cct gca tat        144
Asp Asp Arg Ile Gln Ser Leu Asn Ser Pro Tyr Gly Ala Pro Ala Tyr
            35                  40                  45 caa gaa cgc agc gaa aag ctt att gaa gag atc aaa ctt tta ttt ttg        192
Gln Glu Arg Ser Glu Lys Leu Ile Glu Glu Ile Lys Leu Leu Phe Leu
        50                  55                  60 agt gac atg gac gat agc tgc aat gat agc gat cgt gat tta atc aaa        240
Ser Asp Met Asp Asp Ser Cys Asn Asp Ser Asp Arg Asp Leu Ile Lys
    65                  70                  75 cgt ctt gag atc gtt gat act gtc gag tgt ctg gga att gat cga cat        288
Arg Leu Glu Ile Val Asp Thr Val Glu Cys Leu Gly Ile Asp Arg His
80                  85                  90                  95 ttt caa cct gag ata aaa tta gct ctg gat tac gtt tac aga tgt tgg        336
Phe Gln Pro Glu Ile Lys Leu Ala Leu Asp Tyr Val Tyr Arg Cys Trp
```

```
                100                 105                 110
aac gaa aga ggc atc gga gag gga tca aga gat tcc ctc aag aaa gat      384
Asn Glu Arg Gly Ile Gly Glu Gly Ser Arg Asp Ser Leu Lys Lys Asp
            115                 120                 125 ctg aac gct aca gct ttg gga ttc cgg gct ctc cga ctc cat cga tat      432
Leu Asn Ala Thr Ala Leu Gly Phe Arg Ala Leu Arg Leu His Arg Tyr
        130                 135                 140 aac gta tcc tca ggt gtc ttg gag aat ttc aga gat gat aac ggg cag      480
Asn Val Ser Ser Gly Val Leu Glu Asn Phe Arg Asp Asp Asn Gly Gln
    145                 150                 155 ttc ttc tgc ggt tct aca gtt gaa gaa gaa gga gca gaa gca tat aat      528
Phe Phe Cys Gly Ser Thr Val Glu Glu Glu Gly Ala Glu Ala Tyr Asn
160                 165                 170                 175 aaa cac gta aga tgc atg ctg tca tta tcg cga gct tca aac att tta      576
Lys His Val Arg Cys Met Leu Ser Leu Ser Arg Ala Ser Asn Ile Leu
                180                 185                 190 ttt ccg ggc gaa aaa gtg atg gaa gag gcg aag gca ttc aca aca aat      624
Phe Pro Gly Glu Lys Val Met Glu Glu Ala Lys Ala Phe Thr Thr Asn
            195                 200                 205 tat cta aag aaa gtt tta gca gga cgg gag gct acc cac gtc gat gaa      672
Tyr Leu Lys Lys Val Leu Ala Gly Arg Glu Ala Thr His Val Asp Glu
        210                 215                 220 agc ctt ttg gga gag gtg aag tac gca ttg gag ttt cca tgg cat tgc      720
Ser Leu Leu Gly Glu Val Lys Tyr Ala Leu Glu Phe Pro Trp His Cys
    225                 230                 235 agt gtg cag aga tgg gag gca agg agc ttt atc gaa ata ttt gga caa      768
Ser Val Gln Arg Trp Glu Ala Arg Ser Phe Ile Glu Ile Phe Gly Gln
240                 245                 250                 255 att gat tca gag ctt aag tcg aat ttg agc aaa aaa atg tta gag ttg      816
Ile Asp Ser Glu Leu Lys Ser Asn Leu Ser Lys Lys Met Leu Glu Leu
                260                 265                 270 gcg aaa ttg gac ttc aat att ctg caa tgc aca cat cag aaa gaa ctg      864
Ala Lys Leu Asp Phe Asn Ile Leu Gln Cys Thr His Gln Lys Glu Leu
            275                 280                 285 cag att atc tca agg tgg ttc gca gac tca agt ata gca tcc ctg aat      912
Gln Ile Ile Ser Arg Trp Phe Ala Asp Ser Ser Ile Ala Ser Leu Asn
        290                 295                 300 ttc tat cgg aaa tgt tac gtc gaa ttt tac ttt tgg atg gct gca gcc      960
Phe Tyr Arg Lys Cys Tyr Val Glu Phe Tyr Phe Trp Met Ala Ala Ala
    305                 310                 315 atc tcc gag ccg gag ttt tct gga agc aga gtt gcc ttc aca aaa att     1008
Ile Ser Glu Pro Glu Phe Ser Gly Ser Arg Val Ala Phe Thr Lys Ile
320                 325                 330                 335 gct ata ctg atg aca atg cta gat gac ctg tac gat act cac gga acc     1056
Ala Ile Leu Met Thr Met Leu Asp Asp Leu Tyr Asp Thr His Gly Thr
                340                 345                 350 ttg gac caa ctc aaa atc ttt aca gag gga gtg aga cga tgg gat gtt     1104
Leu Asp Gln Leu Lys Ile Phe Thr Glu Gly Val Arg Arg Trp Asp Val
            355                 360                 365 tcg ttg gta gag ggc ctc cca gac ttc atg aaa att gca ttc gag ttc     1152
Ser Leu Val Glu Gly Leu Pro Asp Phe Met Lys Ile Ala Phe Glu Phe
        370                 375                 380 tgg tta aag aca tct aat gaa ttg att gct gaa gct gtt aaa gcg caa     1200
Trp Leu Lys Thr Ser Asn Glu Leu Ile Ala Glu Ala Val Lys Ala Gln
    385                 390                 395 ggg caa gat atg gcg gcc tac ata aga aaa aat gca tgg gag cga tac     1248
Gly Gln Asp Met Ala Ala Tyr Ile Arg Lys Asn Ala Trp Glu Arg Tyr
400                 405                 410                 415 ctt gaa gct tat ctg caa gat gcg gaa tgg ata gcc act gga cat gtc     1296
```

```
Leu Glu Ala Tyr Leu Gln Asp Ala Glu Trp Ile Ala Thr Gly His Val
            420                 425                 430 ccc acc ttt gat gag tac ttg aat aat ggc aca cca aac act ggg atg    1344
Pro Thr Phe Asp Glu Tyr Leu Asn Asn Gly Thr Pro Asn Thr Gly Met
            435                 440                 445 tgt gta ttg aat ttg att ccg ctt ctg tta atg ggt gaa cat tta cca    1392
Cys Val Leu Asn Leu Ile Pro Leu Leu Leu Met Gly Glu His Leu Pro
        450                 455                 460 atc gac att ctg gag caa ata ttc ttg ccc tcc agg ttc cac cat ctc    1440
Ile Asp Ile Leu Glu Gln Ile Phe Leu Pro Ser Arg Phe His His Leu
        465                 470                 475 att gaa ttg gct tcc agg ctc gtc gat gac gcg aga gat ttc cag gcg    1488
Ile Glu Leu Ala Ser Arg Leu Val Asp Asp Ala Arg Asp Phe Gln Ala
480                 485                 490                 495 gag aag gat cat ggg gat tta tcg tgt att gag tgt tat tta aaa gat    1536
Glu Lys Asp His Gly Asp Leu Ser Cys Ile Glu Cys Tyr Leu Lys Asp
                500                 505                 510 cat cct gag tct aca gta gaa gat gct tta aat cat gtt aat ggc ctc    1584
His Pro Glu Ser Thr Val Glu Asp Ala Leu Asn His Val Asn Gly Leu
            515                 520                 525 ctt ggc aat tgc ctt ctg gaa atg aat tgg aag ttc tta aag aag cag    1632
Leu Gly Asn Cys Leu Leu Glu Met Asn Trp Lys Phe Leu Lys Lys Gln
        530                 535                 540 gac agt gtg cca ctc tcg tgt aag aag tac agc ttc cat gta ttg gca    1680
Asp Ser Val Pro Leu Ser Cys Lys Lys Tyr Ser Phe His Val Leu Ala
545                 550                 555 cga agc atc caa ttc atg tac aat caa ggc gat ggc ttc tcc att tcg    1728
Arg Ser Ile Gln Phe Met Tyr Asn Gln Gly Asp Gly Phe Ser Ile Ser
560                 565                 570                 575 aac aaa gtg atc aag gat caa gtg cag aaa gtt ctt att gtc ccc gtg    1776
Asn Lys Val Ile Lys Asp Gln Val Gln Lys Val Leu Ile Val Pro Val
                580                 585                 590 cct att tgagaattcc cgggtcgact cgagcggccg catcgtgact gactgacgat    1832
Pro Ile ctgcctcgcg cgtttcggtg atgacggtga aaacctctga cacatgcagc tcccggagac    1892
ggtcacagct tgtctgtaag cggatgccgg gagcagacaa gcccgtcagg gcgcgtcagc    1952
gggtgttggc gggtgtccgg gcgca                                           1977

<210> SEQ ID NO 24
<211> LENGTH: 593
<212> TYPE: PRT
<213> ORGANISM: Abies grandis

<400> SEQUENCE: 24

Met Ala Gln Ile Ser Glu Ser Val Ser Pro Ser Thr Asp Leu Lys Ser
  1               5                  10                  15

Thr Glu Ser Ser Ile Thr Ser Asn Arg His Gly Asn Met Trp Glu Asp
             20                  25                  30

Asp Arg Ile Gln Ser Leu Asn Ser Pro Tyr Gly Ala Pro Ala Tyr Gln
         35                  40                  45

Glu Arg Ser Glu Lys Leu Ile Glu Ile Lys Leu Leu Phe Leu Ser
     50                  55                  60

Asp Met Asp Asp Ser Cys Asn Ser Asp Arg Asp Leu Ile Lys Arg
 65                  70                  75                  80

Leu Glu Ile Val Asp Thr Val Glu Cys Leu Gly Ile Asp Arg His Phe
                 85                  90                  95

Gln Pro Glu Ile Lys Leu Ala Leu Asp Tyr Val Tyr Arg Cys Trp Asn
```

-continued

```
                      100                 105                 110
Glu Arg Gly Ile Gly Glu Gly Ser Arg Asp Ser Leu Lys Lys Asp Leu
            115                 120                 125
Asn Ala Thr Ala Leu Gly Phe Arg Ala Leu Arg Leu His Arg Tyr Asn
130                 135                 140
Val Ser Ser Gly Val Leu Glu Asn Phe Arg Asp Asp Asn Gly Gln Phe
145                 150                 155                 160
Phe Cys Gly Ser Thr Val Glu Glu Gly Ala Glu Ala Tyr Asn Lys
                165                 170                 175
His Val Arg Cys Met Leu Ser Leu Ser Arg Ala Ser Asn Ile Leu Phe
                180                 185                 190
Pro Gly Glu Lys Val Met Glu Glu Ala Lys Ala Phe Thr Thr Asn Tyr
            195                 200                 205
Leu Lys Lys Val Leu Ala Gly Arg Glu Ala Thr His Val Asp Glu Ser
            210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
            275                 280                 285
Ile Ile Ser Arg Trp Phe Ala Asp Ser Ser Ile Ala Ser Leu Asn Phe
            290                 295                 300
Tyr Arg Lys Cys Tyr Val Glu Phe Tyr Phe Trp Met Ala Ala Ile
305                 310                 315                 320
Ser Glu Pro Glu Phe Ser Gly Ser Arg Val Ala Phe Thr Lys Ile Ala
                325                 330                 335
Ile Leu Met Thr Met Leu Asp Asp Leu Tyr Asp Thr His Gly Thr Leu
                340                 345                 350
Asp Gln Leu Lys Ile Phe Thr Glu Gly Val Arg Arg Trp Asp Val Ser
            355                 360                 365
Leu Val Glu Gly Leu Pro Asp Phe Met Lys Ile Ala Phe Glu Phe Trp
370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
                405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
            435                 440                 445
Val Leu Asn Leu Ile Pro Leu Leu Met Gly Glu His Leu Pro Ile
450                 455                 460
Asp Ile Leu Glu Gln Ile Phe Leu Pro Ser Arg Phe His His Leu Ile
465                 470                 475                 480
Glu Leu Ala Ser Arg Leu Val Asp Asp Ala Arg Asp Phe Gln Ala Glu
                485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
            515                 520                 525
```

```
Gly Asn Cys Leu Leu Glu Met Asn Trp Lys Phe Leu Lys Lys Gln Asp
    530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590

Ile

<210> SEQ ID NO 25
<211> LENGTH: 116
<212> TYPE: DNA
<213> ORGANISM: Abies grandis

<400> SEQUENCE: 25
ggtctagatt gcatgtagtc ggggaagtgg tctaccaacg aaacatccca tcgtctcact    60
ccctctgtaa agattttgag ttggtccaag gttccatgcg catcataccc atcgtc      116

<210> SEQ ID NO 26
<211> LENGTH: 1416
<212> TYPE: DNA
<213> ORGANISM: Abies grandis

<400> SEQUENCE: 26
aaaaagtgat ggaagaggcg aaggcattca caacaaatta tctaaagaaa gttttagcag    60
gacgggaggc tacccacgtc gatgaaagcc ttttgggaga ggtgaagtac gcattggagt   120
ttccatggca ttgcagtgtg cagagatggg aggcaaggag ctttatcgaa atatttggac   180
aaattgattc agagcttaag tcgaatttga gcaaaaaaat gttagagttg gcgaaattgg   240
acttcaatat tctgcaatgc acacatcaga agaactgcag gattatctca aggtggttcg   300
cagactcaag tatagcatcc tgaatttct atcggaaatg ttacgtcgaa ttttactttt   360
ggatggctgc agccatctcc gagccggagt tttctggaag cagagttgcc ttcacaaaaa   420
ttgctatact gatgacaatg ctagatgacc tgtacgatac tcacggaacc ttggaccaac   480
tcaaaatctt tacagaggga gtgagacgat gggatgtttc gttggtagag ggcctcccag   540
acttcatgaa aattgcattc gagttctggt aaagacatc taatgaattg attgctgaag   600
ctgttaaagc gcaagggcaa gatatggcgg cctacataag aaaaaatgca tgggagcgat   660
accttgaagc ttatctgcaa gatgcggaat ggatagccac tggacatgtc cccacctttg   720
atgagtactt gaataatggc acaccaaaca ctgggatgtg tgtattgaat ttgattccgc   780
ttctgttaat gggtgaacat ttaccaatcg acattctgga gcaaatattc ttgccctcca   840
ggttccacca tctcattgaa ttggcttcca ggctcgtcga tgacgcagag gatttccagg   900
cggagaagga tcatggggat ttatcgtgta ttgagtgtta tttaaaagat catcctgagt   960
ctacagtaga agatgcttta aatcatgtta atggcctcct tggcaattgc cttctggaaa  1020
tgaattggaa gttcttaaag aagcaggaca gtgtgccact ctcgtgtaag aagtacagct  1080
tccatgtatt ggcacgaagc atccaattca tgtacaatca aggcgatggc ttctccattt  1140
cgaacaaagt gatcaaggat caagtgcaga agttcttat tgtccccgtg cctatttgat  1200
agtagatact agatagtaga ttagtagcta ttagtattta tttcatatca atatttacta  1260
atgctgatga tggttaaagt ccattcagac caatctttgg tttattggac ttaaataaat  1320
```
gaattaatta gtttgtttta aaattgtact atttactgtt ggaaataatg ttttcattat    1380
tgaaataact agcacaacta ttttagtgtg gttgat    1416

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(23)
<223> OTHER INFORMATION: reverse RACE primer specific for ag 5.9

<400> SEQUENCE: 27
gtctatcgat tcccagccat tcc    23

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(30)
<223> OTHER INFORMATION: 5' PCR primer specific for ag5.9

<400> SEQUENCE: 28
tggtaccatg gctggcgttt ctgctgtatc    30

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(27)
<223> OTHER INFORMATION: 3' RACE primer specific for ag5.9

<400> SEQUENCE: 29
tatgaattct caaataggca cggggac    27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(27)
<223> OTHER INFORMATION: PCR primer 5NdeI

<400> SEQUENCE: 30
ctggttccgc gtggacatat ggctcag    27

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(32)
<223> OTHER INFORMATION: PCR primer 5BamHI

<400> SEQUENCE: 31
gtcagtgacg atggatcctc aaataggcac gg          32

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: amino acid
      motif
<221> NAME/KEY: DOMAIN
<222> LOCATION: (1)..(8)
<223> OTHER INFORMATION: conserved sequence motif wherein Xaa at
      position 3 is Thr or Ile; Xaa at position 4 is Ile or Tyr or
      Phe; Xaa at position 6 is Ala or Val; Xaa at
      position 8 is Ala or Gly

<400> SEQUENCE: 32

Asp Asp Xaa Xaa Asp Xaa Tyr Xaa
 1               5

<210> SEQ ID NO 33
<211> LENGTH: 622
<212> TYPE: DNA
<213> ORGANISM: Abies grandis

<400> SEQUENCE: 33
tgacatagtt cacgaggtgg cttgggaggc agagaaggaa cagggggcgtg aattggtcag     60 cttttcaga  aagggatggg aggattatct tctgggttat tatgaagaag ctgaatggtt    120
agctgctgag tatgtgccta ccttggacga gtacataaag aatggaatca catctatcgg    180
ccaacgtata cttctgttga gtggagtgtt gataatggat gggcaactcc tttcgcaaga    240
ggcattagag aaagtagatt atccaggaag acgtgttctc acagagctga atagcctcat    300
ttcccgcctg gcggatgaca cgaagacata taaagctgag aaggctcgtg gagaattggc    360
gtccagcatt gaatgttaca tgaaagacca tcctgaatgt acagaggaag aggctctcga    420
tcacatctat agcattctgg agccggcggt gaaggaactg acaagagagt ttctgaagcc    480
cgacgacgtc ccattcgcct gcaagaagat gcttttcgag gagacaagag tgacgatggt    540
gatattcaag gatggagatg gattcggtgt ttccaaatta gaagtcaaag atcatatcaa    600
agagtgtctc attgaaccgc tg                                             622

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(21)
<223> OTHER INFORMATION: Oligonucleotide primer 1.28F

<400> SEQUENCE: 34
tgacatagtt cacgaggtgg c          21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      oligonucleotide -continued

```
<221> NAME/KEY: misc_feature
<222> LOCATION: (1)..(21)
<223> OTHER INFORMATION: Oligonucleotide primer 1.28R

<400> SEQUENCE: 35
cagcggttca atgagacact c                                              21

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: amino acid
      sequence motif
<221> NAME/KEY: DOMAIN
<222> LOCATION: (1)..(5)
<223> OTHER INFORMATION: conserved amino acid sequence motif wherein
      Xaa at positions 3 and 4 represent any amino acid

<400> SEQUENCE: 36

Asp Asp Xaa Xaa Asp
  1               5

<210> SEQ ID NO 37
<211> LENGTH: 2528
<212> TYPE: DNA
<213> ORGANISM: Abies grandis
<220> FEATURE:
<221> NAME/KEY: CDS
<222> LOCATION: (1)..(2451)

<400> SEQUENCE: 37 atg gct ggc gtt tct gct gta tca aag gtt tcc agc ttg gtt tgt gat     48
Met Ala Gly Val Ser Ala Val Ser Lys Val Ser Ser Leu Val Cys Asp
  1               5                  10                  15 ttg tcg agt acc agc ggc ttg att cga aga act gcc aat cct cat ccc     96
Leu Ser Ser Thr Ser Gly Leu Ile Arg Arg Thr Ala Asn Pro His Pro
             20                  25                  30 aat gtc tgg ggt tat gat ctt gtg cat tct ctt aaa tca cct tat att    144
Asn Val Trp Gly Tyr Asp Leu Val His Ser Leu Lys Ser Pro Tyr Ile
         35                  40                  45 gat tct agt tac aga gaa cgc gcg gag gtc ctt gtt agc gag att aaa    192
Asp Ser Ser Tyr Arg Glu Arg Ala Glu Val Leu Val Ser Glu Ile Lys
     50                  55                  60 gtg atg ctt aat cca gct att aca gga gat gga gaa tca atg att act    240
Val Met Leu Asn Pro Ala Ile Thr Gly Asp Gly Glu Ser Met Ile Thr
 65                  70                  75                  80 cca tct gct tat gac aca gca tgg gta gcg agg gtg ccc gcc att gat    288
Pro Ser Ala Tyr Asp Thr Ala Trp Val Ala Arg Val Pro Ala Ile Asp
                 85                  90                  95 ggc tct gct cgc ccg caa ttt ccc caa aca gtt gac tgg att ttg aaa    336
Gly Ser Ala Arg Pro Gln Phe Pro Gln Thr Val Asp Trp Ile Leu Lys
            100                 105                 110 aac cag tta aaa gat ggt tca tgg gga att cag tcc cac ttt ctg ctg    384
Asn Gln Leu Lys Asp Gly Ser Trp Gly Ile Gln Ser His Phe Leu Leu
        115                 120                 125 tcc gac cgt ctt ctt gcc act ctt tct tgt gtt ctt gtg ctc ctt aaa    432
Ser Asp Arg Leu Leu Ala Thr Leu Ser Cys Val Leu Val Leu Leu Lys
    130                 135                 140 tgg aac gtt ggg gat ctg caa gta gag cag gga att gaa ttc ata aag    480
Trp Asn Val Gly Asp Leu Gln Val Glu Gln Gly Ile Glu Phe Ile Lys
145                 150                 155                 160 agc aat ctg gaa cta gta aag gat gaa acc gat caa gat agc ttg gta    528
Ser Asn Leu Glu Leu Val Lys Asp Glu Thr Asp Gln Asp Ser Leu Val
```

-continued

```
              165                 170                 175
aca gac ttt gag atc ata ttt cct tct ctg tta aga gaa gct caa tct       576
Thr Asp Phe Glu Ile Ile Phe Pro Ser Leu Leu Arg Glu Ala Gln Ser
            180                 185                 190 ctg cgc ctc gga ctt ccc tac gac ctg cct tat ata cat ctg ttg cag       624
Leu Arg Leu Gly Leu Pro Tyr Asp Leu Pro Tyr Ile His Leu Leu Gln
            195                 200                 205 act aaa cgg cag gaa aga tta gca aaa ctt tca agg gag gaa att tat       672
Thr Lys Arg Gln Glu Arg Leu Ala Lys Leu Ser Arg Glu Glu Ile Tyr
            210                 215                 220 gcg gtt ccg tcg cca ttg ttg tat tct tta gag gga ata caa gat ata       720
Ala Val Pro Ser Pro Leu Leu Tyr Ser Leu Glu Gly Ile Gln Asp Ile
225                 230                 235                 240 gtt gaa tgg gaa cga ata atg gaa gtt caa agt cag gat ggg tct ttc       768
Val Glu Trp Glu Arg Ile Met Glu Val Gln Ser Gln Asp Gly Ser Phe
            245                 250                 255 tta agc tca cct gct tct act gcc tgc gtt ttc atg cac aca gga gac       816
Leu Ser Ser Pro Ala Ser Thr Ala Cys Val Phe Met His Thr Gly Asp
            260                 265                 270 gcg aaa tgc ctt gaa ttc ttg aac agt gtg atg atc aag ttt gga aat       864
Ala Lys Cys Leu Glu Phe Leu Asn Ser Val Met Ile Lys Phe Gly Asn
            275                 280                 285 ttt gtt ccc tgc ctg tat cct gtg gat ctg ctg gaa cgc ctg ttg atc       912
Phe Val Pro Cys Leu Tyr Pro Val Asp Leu Leu Glu Arg Leu Leu Ile
            290                 295                 300 gta gat aat att gta cgc ctt gga atc tat aga cac ttt gaa aag gaa       960
Val Asp Asn Ile Val Arg Leu Gly Ile Tyr Arg His Phe Glu Lys Glu
305                 310                 315                 320 atc aag gaa gct ctt gat tat gtt tac agg cat tgg aac gaa aga gga      1008
Ile Lys Glu Ala Leu Asp Tyr Val Tyr Arg His Trp Asn Glu Arg Gly
            325                 330                 335 att ggg tgg ggc aga cta aat ccc ata gca gat ctt gag acc act gct      1056
Ile Gly Trp Gly Arg Leu Asn Pro Ile Ala Asp Leu Glu Thr Thr Ala
            340                 345                 350 ttg gga ttt cga ttg ctt cgg ctg cat agg tac aat gta tct cca gcc      1104
Leu Gly Phe Arg Leu Leu Arg Leu His Arg Tyr Asn Val Ser Pro Ala
            355                 360                 365 att ttt gac aac ttc aaa gat gcc aat ggg aaa ttc att tgc tcg acc      1152
Ile Phe Asp Asn Phe Lys Asp Ala Asn Gly Lys Phe Ile Cys Ser Thr
            370                 375                 380 ggt caa ttc aac aaa gat gta gca agc atg ctg aat ctt tat aga gct      1200
Gly Gln Phe Asn Lys Asp Val Ala Ser Met Leu Asn Leu Tyr Arg Ala
385                 390                 395                 400 tcc cag ctc gca ttt ccc gga gaa aac att ctt gat gaa gct aaa agc      1248
Ser Gln Leu Ala Phe Pro Gly Glu Asn Ile Leu Asp Glu Ala Lys Ser
            405                 410                 415 ttc gct act aaa tat ttg aga gaa gct ctt gag aaa agt gag act tcc      1296
Phe Ala Thr Lys Tyr Leu Arg Glu Ala Leu Glu Lys Ser Glu Thr Ser
            420                 425                 430 agt gca tgg aac aac aaa caa aac ctg agc caa gag atc aaa tac gcg      1344
Ser Ala Trp Asn Asn Lys Gln Asn Leu Ser Gln Glu Ile Lys Tyr Ala
            435                 440                 445 ctg aag act tct tgg cat gcc agt gtt ccg aga gtg gaa gca aag aga      1392
Leu Lys Thr Ser Trp His Ala Ser Val Pro Arg Val Glu Ala Lys Arg
            450                 455                 460 tac tgt caa gtg tat cgc cca gat tat gca cgc ata gca aaa tgc gtt      1440
Tyr Cys Gln Val Tyr Arg Pro Asp Tyr Ala Arg Ile Ala Lys Cys Val
465                 470                 475                 480 tac aag cta ccc tac gtg aac aat gaa aag ttt tta gag ctg gga aaa      1488
```

```
                Tyr Lys Leu Pro Tyr Val Asn Asn Glu Lys Phe Leu Glu Leu Gly Lys
                                485                 490                 495 tta gat ttc aac att atc cag tcc atc cac caa gaa gaa atg aag aat       1536
Leu Asp Phe Asn Ile Ile Gln Ser Ile His Gln Glu Glu Met Lys Asn
            500                 505                 510 gtt acc agc tgg ttt aga gat tcg ggg ttg cca cta ttc acc ttc gct       1584
Val Thr Ser Trp Phe Arg Asp Ser Gly Leu Pro Leu Phe Thr Phe Ala
        515                 520                 525 cgg gag agg ccg ctg gaa ttc tac ttc tta gta gcg gcg ggg acc tat       1632
Arg Glu Arg Pro Leu Glu Phe Tyr Phe Leu Val Ala Ala Gly Thr Tyr
    530                 535                 540 gaa ccc cag tat gcc aaa tgc agg ttc ctc ttt aca aaa gtg gca tgc       1680
Glu Pro Gln Tyr Ala Lys Cys Arg Phe Leu Phe Thr Lys Val Ala Cys
545                 550                 555                 560 ttg cag act gtt ctg gac gat atg tat gac act tat gga acc cta gat       1728
Leu Gln Thr Val Leu Asp Asp Met Tyr Asp Thr Tyr Gly Thr Leu Asp
                565                 570                 575 gaa ttg aag cta ttc act gag gct gtg aga aga tgg gac ctc tcc ttt       1776
Glu Leu Lys Leu Phe Thr Glu Ala Val Arg Arg Trp Asp Leu Ser Phe
            580                 585                 590 aca gaa aac ctt cca gac tat atg aaa cta tgt tac caa atc tat tat       1824
Thr Glu Asn Leu Pro Asp Tyr Met Lys Leu Cys Tyr Gln Ile Tyr Tyr
        595                 600                 605 gac ata gtt cac gag gtg gct tgg gag gca gag aag gaa cag ggg cgt       1872
Asp Ile Val His Glu Val Ala Trp Glu Ala Glu Lys Glu Gln Gly Arg
    610                 615                 620 gaa ttg gtc agc ttt ttc aga aag gga tgg gag gat tat ctt ctg ggt       1920
Glu Leu Val Ser Phe Phe Arg Lys Gly Trp Glu Asp Tyr Leu Leu Gly
625                 630                 635                 640 tat tat gaa gaa gct gaa tgg tta gct gct gag tat gtg cct acc ttg       1968
Tyr Tyr Glu Glu Ala Glu Trp Leu Ala Ala Glu Tyr Val Pro Thr Leu
                645                 650                 655 gac gag tac ata aag aat gga atc aca tct atc ggc caa cgt ata ctt       2016
Asp Glu Tyr Ile Lys Asn Gly Ile Thr Ser Ile Gly Gln Arg Ile Leu
            660                 665                 670 ctg ttg agt gga gtg ttg ata atg gat ggg caa ctc ctt tcg caa gag       2064
Leu Leu Ser Gly Val Leu Ile Met Asp Gly Gln Leu Leu Ser Gln Glu
        675                 680                 685 gca tta gag aaa gta gat tat cca gga aga cgt gtt ctc aca gag ctg       2112
Ala Leu Glu Lys Val Asp Tyr Pro Gly Arg Arg Val Leu Thr Glu Leu
    690                 695                 700 aat agc ctc att tcc cgc ctg gcg gat gac acg aag aca tat aaa gct       2160
Asn Ser Leu Ile Ser Arg Leu Ala Asp Asp Thr Lys Thr Tyr Lys Ala
705                 710                 715                 720 gag aag gct cgt gga gaa ttg gcg tcc agc att gaa tgt tac atg aaa       2208
Glu Lys Ala Arg Gly Glu Leu Ala Ser Ser Ile Glu Cys Tyr Met Lys
                725                 730                 735 gac cat cct gaa tgt aca gag gaa gag gct ctc gat cac atc tat agc       2256
Asp His Pro Glu Cys Thr Glu Glu Glu Ala Leu Asp His Ile Tyr Ser
            740                 745                 750 att ctg gag ccg gcg gtg aag gaa ctg aca aga gag ttt ctg aag ccc       2304
Ile Leu Glu Pro Ala Val Lys Glu Leu Thr Arg Glu Phe Leu Lys Pro
        755                 760                 765 gac gac gtc cca ttc gcc tgc aag aag atg ctt ttc gag gag aca aga       2352
Asp Asp Val Pro Phe Ala Cys Lys Lys Met Leu Phe Glu Glu Thr Arg
    770                 775                 780 gtg acg atg gtg ata ttc aag gat gga gat gga ttc ggt gtt tcc aaa       2400
Val Thr Met Val Ile Phe Lys Asp Gly Asp Gly Phe Gly Val Ser Lys
785                 790                 795                 800
```

```
tta gaa gtc aaa gat cat atc aaa gag tgt ctc att gaa ccg ctg cca    2448
Leu Glu Val Lys Asp His Ile Lys Glu Cys Leu Ile Glu Pro Leu Pro
            805                 810                 815 ctg taatcaaaat agttgcaata ataattgaaa taatctcaac tatgtttcac         2501
Leu aaaaaaaaaa aaaaaaaaaa aaaaaaa                                      2528
```

<210> SEQ ID NO 38
<211> LENGTH: 817
<212> TYPE: PRT
<213> ORGANISM: Abies grandis

<400> SEQUENCE: 38

```
Met Ala Gly Val Ser Ala Val Ser Lys Val Ser Ser Leu Val Cys Asp
 1               5                  10                  15

Leu Ser Ser Thr Ser Gly Leu Ile Arg Arg Thr Ala Asn Pro His Pro
            20                  25                  30

Asn Val Trp Gly Tyr Asp Leu Val His Ser Leu Lys Ser Pro Tyr Ile
        35                  40                  45

Asp Ser Ser Tyr Arg Glu Arg Ala Glu Val Leu Val Ser Glu Ile Lys
    50                  55                  60

Val Met Leu Asn Pro Ala Ile Thr Gly Asp Gly Glu Ser Met Ile Thr
65                  70                  75                  80

Pro Ser Ala Tyr Asp Thr Ala Trp Val Ala Arg Val Pro Ala Ile Asp
                85                  90                  95

Gly Ser Ala Arg Pro Gln Phe Pro Gln Thr Val Asp Trp Ile Leu Lys
            100                 105                 110

Asn Gln Leu Lys Asp Gly Ser Trp Gly Ile Gln Ser His Phe Leu Leu
        115                 120                 125

Ser Asp Arg Leu Leu Ala Thr Leu Ser Cys Val Leu Val Leu Leu Lys
    130                 135                 140

Trp Asn Val Gly Asp Leu Gln Val Glu Gln Gly Ile Glu Phe Ile Lys
145                 150                 155                 160

Ser Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
            180                 185                 190

Leu Arg Leu Gly Leu Pro Tyr Asp Leu Pro Tyr Ile His Leu Leu Gln
        195                 200                 205

Thr Lys Arg Gln Glu Arg Leu Ala Lys Leu Ser Arg Glu Glu Ile Tyr
    210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
                245                 250                 255

Leu Ser Ser Pro Ala Ser Thr Ala Cys Val Phe Met His Thr Gly Asp
            260                 265                 270

Ala Lys Cys Leu Glu Phe Leu Asn Ser Val Met Ile Lys Phe Gly Asn
        275                 280                 285

Phe Val Pro Cys Leu Tyr Pro Val Asp Leu Leu Glu Arg Leu Leu Ile
    290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
                325                 330                 335
```

-continued

```
Ile Gly Trp Gly Arg Leu Asn Pro Ile Ala Asp Leu Glu Thr Thr Ala
        340                 345                 350
Leu Gly Phe Arg Leu Leu Arg Leu His Arg Tyr Asn Val Ser Pro Ala
        355                 360                 365
Ile Phe Asp Asn Phe Lys Asp Ala Asn Gly Lys Phe Ile Cys Ser Thr
    370                 375                 380
Gly Gln Phe Asn Lys Asp Val Ala Ser Met Leu Asn Leu Tyr Arg Ala
385                 390                 395                 400
Ser Gln Leu Ala Phe Pro Gly Glu Asn Ile Leu Asp Glu Ala Lys Ser
                405                 410                 415
Phe Ala Thr Lys Tyr Leu Arg Glu Ala Leu Glu Lys Ser Glu Thr Ser
            420                 425                 430
Ser Ala Trp Asn Asn Lys Gln Asn Leu Ser Gln Glu Ile Lys Tyr Ala
        435                 440                 445
Leu Lys Thr Ser Trp His Ala Ser Val Pro Arg Val Glu Ala Lys Arg
    450                 455                 460
Tyr Cys Gln Val Tyr Arg Pro Asp Tyr Ala Arg Ile Ala Lys Cys Val
465                 470                 475                 480
Tyr Lys Leu Pro Tyr Val Asn Asn Glu Lys Phe Leu Glu Leu Gly Lys
                485                 490                 495
Leu Asp Phe Asn Ile Ile Gln Ser Ile His Gln Glu Met Lys Asn
            500                 505                 510
Val Thr Ser Trp Phe Arg Asp Ser Gly Leu Pro Leu Phe Thr Phe Ala
        515                 520                 525
Arg Glu Arg Pro Leu Glu Phe Tyr Phe Leu Val Ala Ala Gly Thr Tyr
    530                 535                 540
Glu Pro Gln Tyr Ala Lys Cys Arg Phe Leu Phe Thr Lys Val Ala Cys
545                 550                 555                 560
Leu Gln Thr Val Leu Asp Asp Met Tyr Asp Thr Tyr Gly Thr Leu Asp
                565                 570                 575
Glu Leu Lys Leu Phe Thr Glu Ala Val Arg Arg Trp Asp Leu Ser Phe
            580                 585                 590
Thr Glu Asn Leu Pro Asp Tyr Met Lys Leu Cys Tyr Gln Ile Tyr Tyr
        595                 600                 605
Asp Ile Val His Glu Val Ala Trp Glu Ala Glu Lys Glu Gln Gly Arg
    610                 615                 620
Glu Leu Val Ser Phe Phe Arg Lys Gly Trp Glu Asp Tyr Leu Leu Gly
625                 630                 635                 640
Tyr Tyr Glu Glu Ala Glu Trp Leu Ala Ala Glu Tyr Val Pro Thr Leu
                645                 650                 655
Asp Glu Tyr Ile Lys Asn Gly Ile Thr Ser Ile Gly Gln Arg Ile Leu
            660                 665                 670
Leu Leu Ser Gly Val Leu Ile Met Asp Gly Gln Leu Leu Ser Gln Glu
        675                 680                 685
Ala Leu Glu Lys Val Asp Tyr Pro Gly Arg Arg Val Leu Thr Glu Leu
    690                 695                 700
Asn Ser Leu Ile Ser Arg Leu Ala Asp Asp Thr Lys Thr Tyr Lys Ala
705                 710                 715                 720
Glu Lys Ala Arg Gly Glu Leu Ala Ser Ser Ile Glu Cys Tyr Met Lys
                725                 730                 735
Asp His Pro Glu Cys Thr Glu Glu Ala Leu Asp His Ile Tyr Ser
            740                 745                 750
```

-continued

| | | | | | | | | | | | | |
|---|---|---|---|---|---|---|---|---|---|---|---|---|
|Ile|Leu|Glu|Pro|Ala|Val|Lys|Glu|Leu|Thr|Arg|Glu|Phe|Leu|Lys|Pro|
| |  |  |755|  |  |  |760|  |  |  |765|  |  |  |  |

Asp Asp Val Pro Phe Ala Cys Lys Lys Met Leu Phe Glu Glu Thr Arg
        770             775             780

Val Thr Met Val Ile Phe Lys Asp Gly Asp Gly Phe Gly Val Ser Lys
785             790             795             800

Leu Glu Val Lys Asp His Ile Lys Glu Cys Leu Ile Glu Pro Leu Pro
            805             810             815

Leu

<210> SEQ ID NO 39
<211> LENGTH: 2525
<212> TYPE: DNA
<213> ORGANISM: Artificial Sequence
<220> FEATURE:
<223> OTHER INFORMATION: Description of Artificial Sequence:
      computer-generated nucleic acid sequence encoding
      E-alpha-bisabolene synthase
<221> NAME/KEY: CDS
<222> LOCATION: (1)..(2451)

<400> SEQUENCE: 39

```
atg gcc ggc gtt tct gct gta tca aag gtt tcc agc ttg gtt tgt gat      48
Met Ala Gly Val Ser Ala Val Ser Lys Val Ser Ser Leu Val Cys Asp
  1               5                  10                  15 ttg tcg agt acc agc ggc ttg att cga aga act gcc aat cct cat ccc      96
Leu Ser Ser Thr Ser Gly Leu Ile Arg Arg Thr Ala Asn Pro His Pro
             20                  25                  30 aat gtc tgg ggt tat gat ctt gtg cat tct ctt aaa tca cct tat att     144
Asn Val Trp Gly Tyr Asp Leu Val His Ser Leu Lys Ser Pro Tyr Ile
         35                  40                  45 gat tct agt tac aga gaa cgc gcg gag gtc ctt gtt agc gag att aaa     192
Asp Ser Ser Tyr Arg Glu Arg Ala Glu Val Leu Val Ser Glu Ile Lys
     50                  55                  60 gcg atg ctt aat cca gct att aca gga gat gga gaa tca atg att act     240
Ala Met Leu Asn Pro Ala Ile Thr Gly Asp Gly Glu Ser Met Ile Thr
 65                  70                  75                  80 cca tct gct tat gac aca gca tgg gta gcg agg gtg ccc gcc att gat     288
Pro Ser Ala Tyr Asp Thr Ala Trp Val Ala Arg Val Pro Ala Ile Asp
                 85                  90                  95 ggc tct gct cgc ccg caa ttt ccc caa aca gtt gac tgg att ttg aaa     336
Gly Ser Ala Arg Pro Gln Phe Pro Gln Thr Val Asp Trp Ile Leu Lys
            100                 105                 110 aac cag tta aaa gat ggt tca tgg gga att cag tcc cac ttt ctg ctg     384
Asn Gln Leu Lys Asp Gly Ser Trp Gly Ile Gln Ser His Phe Leu Leu
        115                 120                 125 tcc gac cgt ctt ctt gcc act ctt tct tgt gtt ctt gtg ctc ctt aaa     432
Ser Asp Arg Leu Leu Ala Thr Leu Ser Cys Val Leu Val Leu Leu Lys
    130                 135                 140 tgg aac gtt ggg gat ctg caa gta gag cag gga att gaa ttc ata aag     480
Trp Asn Val Gly Asp Leu Gln Val Glu Gln Gly Ile Glu Phe Ile Lys
145                 150                 155                 160 agc aat ctg gaa cta gta aag gat gaa acc gat caa gat agc ttg gta     528
Ser Asn Leu Glu Leu Val Lys Asp Glu Thr Asp Gln Asp Ser Leu Val
                165                 170                 175 aca gac ttt gag atc ata ttt cct tct ctg tta aga gaa gct caa tct     576
Thr Asp Phe Glu Ile Ile Phe Pro Ser Leu Leu Arg Glu Ala Gln Ser
            180                 185                 190 ctg cgc ctc gga ctt ccc tac gac ctg cct tat ata cat ctg ttg cag     624
Leu Arg Leu Gly Leu Pro Tyr Asp Leu Pro Tyr Ile His Leu Leu Gln
        195                 200                 205
```

```
act aaa cgg cag gaa aga tta gca aaa ctt tca agg gag gaa att tat      672
Thr Lys Arg Gln Glu Arg Leu Ala Lys Leu Ser Arg Glu Glu Ile Tyr
    210             215                 220 gcg gtt ccg tcg cca ttg ttg tat tct tta gag gga ata caa gat ata      720
Ala Val Pro Ser Pro Leu Leu Tyr Ser Leu Glu Gly Ile Gln Asp Ile
225             230                 235                 240 gtt gaa tgg gaa cga ata atg gaa gtt caa agt cag gat ggg tct ttc      768
Val Glu Trp Glu Arg Ile Met Glu Val Gln Ser Gln Asp Gly Ser Phe
                245                 250                 255 tta agc tca cct gct tct act gcc tgc gtt ttc atg cac aca gga gac      816
Leu Ser Ser Pro Ala Ser Thr Ala Cys Val Phe Met His Thr Gly Asp
            260                 265                 270 gcg aaa tgc ctt gaa ttc ttg aac agt gtg atg atc aag ttt gga aat      864
Ala Lys Cys Leu Glu Phe Leu Asn Ser Val Met Ile Lys Phe Gly Asn
        275                 280                 285 ttt gtt ccc tgc ctg tat cct gtg gat ctg ctg gaa cgc ctg ttg atc      912
Phe Val Pro Cys Leu Tyr Pro Val Asp Leu Leu Glu Arg Leu Leu Ile
    290                 295                 300 gta gat aat att gta cgc ctt gga atc tat aga cac ttt gaa aag gaa      960
Val Asp Asn Ile Val Arg Leu Gly Ile Tyr Arg His Phe Glu Lys Glu
305             310                 315                 320 atc aag gaa gct ctt gat tat gtt tac agg cat tgg aac gaa aga gga     1008
Ile Lys Glu Ala Leu Asp Tyr Val Tyr Arg His Trp Asn Glu Arg Gly
                325                 330                 335 att ggg tgg ggc aga cta aat ccc ata gca gat ctt gag acc act gct     1056
Ile Gly Trp Gly Arg Leu Asn Pro Ile Ala Asp Leu Glu Thr Thr Ala
            340                 345                 350 ttg gga ttt cga ttg ctt cgg ctg cat agg tac aat gta tct cca gcc     1104
Leu Gly Phe Arg Leu Leu Arg Leu His Arg Tyr Asn Val Ser Pro Ala
        355                 360                 365 att ttt gac aac ttc aaa gat gcc aat ggg aaa ttc att tgc tcg acc     1152
Ile Phe Asp Asn Phe Lys Asp Ala Asn Gly Lys Phe Ile Cys Ser Thr
    370                 375                 380 ggt caa ttc aac aaa gat gta gca agc atg ctg aat ctt tat aga gct     1200
Gly Gln Phe Asn Lys Asp Val Ala Ser Met Leu Asn Leu Tyr Arg Ala
385             390                 395                 400 tcc cag ctc gca ttt ccc gga gaa aac att ctt gat gaa gct aaa agc     1248
Ser Gln Leu Ala Phe Pro Gly Glu Asn Ile Leu Asp Glu Ala Lys Ser
                405                 410                 415 ttc gct act aaa tat ttg aga gaa gct ctt gag aaa agt gag act tcc     1296
Phe Ala Thr Lys Tyr Leu Arg Glu Ala Leu Glu Lys Ser Glu Thr Ser
            420                 425                 430 agt gca tgg aac aac aaa caa aac ctg agc caa gag atc aaa tac gcg     1344
Ser Ala Trp Asn Asn Lys Gln Asn Leu Ser Gln Glu Ile Lys Tyr Ala
        435                 440                 445 ctg aag act tct tgg cat gcc agt gtt ccg aga gtg gaa gca aag aga     1392
Leu Lys Thr Ser Trp His Ala Ser Val Pro Arg Val Glu Ala Lys Arg
    450                 455                 460 tac tgt caa gtg tat cgc cca gat tat gca cgc ata gca aaa tgc gtt     1440
Tyr Cys Gln Val Tyr Arg Pro Asp Tyr Ala Arg Ile Ala Lys Cys Val
465             470                 475                 480 tac aag cta ccc tac gtg aac aat gaa aag ttt tta gag ctg gga aaa     1488
Tyr Lys Leu Pro Tyr Val Asn Asn Glu Lys Phe Leu Glu Leu Gly Lys
                485                 490                 495 tta gat ttc aac att atc cag tcc atc cac caa gaa gaa atg aag aat     1536
Leu Asp Phe Asn Ile Ile Gln Ser Ile His Gln Glu Glu Met Lys Asn
            500                 505                 510 gtt acc agc tgg ttt aga gat tcg ggg ttg cca cta ttc acc ttc gct     1584
Val Thr Ser Trp Phe Arg Asp Ser Gly Leu Pro Leu Phe Thr Phe Ala
```

-continued

| | | | | |
|---|---|---|---|---|
| | 515 | 520 | 525 | |
| cgg gag agg ccg ctg gaa ttc tac ttc tta gta gcg gcg ggg acc tat<br>Arg Glu Arg Pro Leu Glu Phe Tyr Phe Leu Val Ala Ala Gly Thr Tyr<br>530 535 540 | | | | 1632 |
| gaa ccc cag tat gcc aaa tgc agg ttc ctc ttt aca aaa gtg gca tgc<br>Glu Pro Gln Tyr Ala Lys Cys Arg Phe Leu Phe Thr Lys Val Ala Cys<br>545 550 555 560 | | | | 1680 |
| ttg cag act gtt ctg gac gat atg tat gac act tat gga acc cta gat<br>Leu Gln Thr Val Leu Asp Asp Met Tyr Asp Thr Tyr Gly Thr Leu Asp<br>565 570 575 | | | | 1728 |
| gaa ttg aag cta ttc act gag gct gtg aga aga tgg gac ctc tcc ttt<br>Glu Leu Lys Leu Phe Thr Glu Ala Val Arg Arg Trp Asp Leu Ser Phe<br>580 585 590 | | | | 1776 |
| aca gaa aac ctt cca gac tat atg aaa cta tgt tac caa atc tat tat<br>Thr Glu Asn Leu Pro Asp Tyr Met Lys Leu Cys Tyr Gln Ile Tyr Tyr<br>595 600 605 | | | | 1824 |
| gac ata gtt cac gag gtg gct tgg gag gca gag aag gaa cag ggg cgt<br>Asp Ile Val His Glu Val Ala Trp Glu Ala Glu Lys Glu Gln Gly Arg<br>610 615 620 | | | | 1872 |
| gaa ttg gtc agc ttt ttc aga aag gga tgg gag gat tat ctt ctg ggt<br>Glu Leu Val Ser Phe Phe Arg Lys Gly Trp Glu Asp Tyr Leu Leu Gly<br>625 630 635 640 | | | | 1920 |
| tat tat gaa gaa gct gaa tgg tta gct gct gag tat gtg cct acc ttg<br>Tyr Tyr Glu Glu Ala Glu Trp Leu Ala Ala Glu Tyr Val Pro Thr Leu<br>645 650 655 | | | | 1968 |
| gac gag tac ata aag aat gga atc aca tct atc ggc caa cgt ata ctt<br>Asp Glu Tyr Ile Lys Asn Gly Ile Thr Ser Ile Gly Gln Arg Ile Leu<br>660 665 670 | | | | 2016 |
| ctg ttg agt gga gtg ttg ata atg gat ggg caa ctc ctt tcg caa gag<br>Leu Leu Ser Gly Val Leu Ile Met Asp Gly Gln Leu Leu Ser Gln Glu<br>675 680 685 | | | | 2064 |
| gca tta gag aaa gta gat tat cca gga aga cgt gtt ctc aca gag ctg<br>Ala Leu Glu Lys Val Asp Tyr Pro Gly Arg Arg Val Leu Thr Glu Leu<br>690 695 700 | | | | 2112 |
| aat agc ctc att tcc cgc ctg gcg gat gac acg aag aca tat aaa gct<br>Asn Ser Leu Ile Ser Arg Leu Ala Asp Asp Thr Lys Thr Tyr Lys Ala<br>705 710 715 720 | | | | 2160 |
| gag aag gct cgt gga gaa ttg gcg tcc agc att gaa tgt tac atg aaa<br>Glu Lys Ala Arg Gly Glu Leu Ala Ser Ser Ile Glu Cys Tyr Met Lys<br>725 730 735 | | | | 2208 |
| gac cat cct gaa tgt aca gag gaa gag gct ctc gat cac atc tat agc<br>Asp His Pro Glu Cys Thr Glu Glu Glu Ala Leu Asp His Ile Tyr Ser<br>740 745 750 | | | | 2256 |
| att ctg gag ccg gcg gtg aag gaa ctg aca aga gag ttt ctg aag ccc<br>Ile Leu Glu Pro Ala Val Lys Glu Leu Thr Arg Glu Phe Leu Lys Pro<br>755 760 765 | | | | 2304 |
| gac gac gtc cca ttc gcc tgc aag aag atg ctt ttc gag gag aca aga<br>Asp Asp Val Pro Phe Ala Cys Lys Lys Met Leu Phe Glu Glu Thr Arg<br>770 775 780 | | | | 2352 |
| gtg acg atg gtg ata ttc aag gat gga gat gga ttc ggt gtt tcc aaa<br>Val Thr Met Val Ile Phe Lys Asp Gly Asp Gly Phe Gly Val Ser Lys<br>785 790 795 800 | | | | 2400 |
| tta gaa gtc aaa gat cat atc aaa gag tgt ctc att gaa ccg ctg cca<br>Leu Glu Val Lys Asp His Ile Lys Glu Cys Leu Ile Glu Pro Leu Pro<br>805 810 815 | | | | 2448 |
| ctg taatcaaaat agttgcaata ataattgaaa tatcaactat gtttcacaaa<br>Leu | | | | 2501 |
| aaaaaaaaaa aaaaaaaaaa aaaa | | | | 2525 |

-continued

```
<210> SEQ ID NO 40
<211> LENGTH: 817
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 40

Met Ala Gly Val Ser Ala Val Ser Lys Val Ser Ser Leu Val Cys Asp
 1               5                  10                  15

Leu Ser Ser Thr Ser Gly Leu Ile Arg Arg Thr Ala Asn Pro His Pro
                20                  25                  30

Asn Val Trp Gly Tyr Asp Leu Val His Ser Leu Lys Ser Pro Tyr Ile
            35                  40                  45

Asp Ser Ser Tyr Arg Glu Arg Ala Glu Val Leu Val Ser Glu Ile Lys
        50                  55                  60

Ala Met Leu Asn Pro Ala Ile Thr Gly Asp Gly Glu Ser Met Ile Thr
65                  70                  75                  80

Pro Ser Ala Tyr Asp Thr Ala Trp Val Ala Arg Val Pro Ala Ile Asp
                85                  90                  95

Gly Ser Ala Arg Pro Gln Phe Pro Gln Thr Val Asp Trp Ile Leu Lys
            100                 105                 110

Asn Gln Leu Lys Asp Gly Ser Trp Gly Ile Gln Ser His Phe Leu Leu
        115                 120                 125

Ser Asp Arg Leu Leu Ala Thr Leu Ser Cys Val Leu Val Leu Leu Lys
    130                 135                 140

Trp Asn Val Gly Asp Leu Gln Val Glu Gln Gly Ile Glu Phe Ile Lys
145                 150                 155                 160

Ser Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
            180                 185                 190

Leu Arg Leu Gly Leu Pro Tyr Asp Leu Pro Tyr Ile His Leu Leu Gln
        195                 200                 205

Thr Lys Arg Gln Glu Arg Leu Ala Lys Leu Ser Arg Glu Glu Ile Tyr
    210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
                245                 250                 255

Leu Ser Ser Pro Ala Ser Thr Ala Cys Val Phe Met His Thr Gly Asp
            260                 265                 270

Ala Lys Cys Leu Glu Phe Leu Asn Ser Val Met Ile Lys Phe Gly Asn
        275                 280                 285

Phe Val Pro Cys Leu Tyr Pro Val Asp Leu Leu Glu Arg Leu Leu Ile
    290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
                325                 330                 335

Ile Gly Trp Gly Arg Leu Asn Pro Ile Ala Asp Leu Glu Thr Thr Ala
            340                 345                 350
```

-continued

```
Leu Gly Phe Arg Leu Leu Arg Leu His Arg Tyr Asn Val Ser Pro Ala
        355                 360                 365
Ile Phe Asp Asn Phe Lys Asp Ala Asn Gly Lys Phe Ile Cys Ser Thr
    370                 375                 380
Gly Gln Phe Asn Lys Asp Val Ala Ser Met Leu Asn Leu Tyr Arg Ala
385                 390                 395                 400
Ser Gln Leu Ala Phe Pro Gly Glu Asn Ile Leu Asp Glu Ala Lys Ser
                405                 410                 415
Phe Ala Thr Lys Tyr Leu Arg Glu Ala Leu Glu Lys Ser Glu Thr Ser
            420                 425                 430
Ser Ala Trp Asn Asn Lys Gln Asn Leu Ser Gln Glu Ile Lys Tyr Ala
        435                 440                 445
Leu Lys Thr Ser Trp His Ala Ser Val Pro Arg Val Glu Ala Lys Arg
    450                 455                 460
Tyr Cys Gln Val Tyr Arg Pro Asp Tyr Ala Arg Ile Ala Lys Cys Val
465                 470                 475                 480
Tyr Lys Leu Pro Tyr Val Asn Asn Glu Lys Phe Leu Glu Leu Gly Lys
                485                 490                 495
Leu Asp Phe Asn Ile Ile Gln Ser Ile His Gln Glu Met Lys Asn
            500                 505                 510
Val Thr Ser Trp Phe Arg Asp Ser Gly Leu Pro Leu Phe Thr Phe Ala
        515                 520                 525
Arg Glu Arg Pro Leu Glu Phe Tyr Phe Leu Val Ala Ala Gly Thr Tyr
    530                 535                 540
Glu Pro Gln Tyr Ala Lys Cys Arg Phe Leu Phe Thr Lys Val Ala Cys
545                 550                 555                 560
Leu Gln Thr Val Leu Asp Asp Met Tyr Asp Thr Tyr Gly Thr Leu Asp
                565                 570                 575
Glu Leu Lys Leu Phe Thr Glu Ala Val Arg Arg Trp Asp Leu Ser Phe
            580                 585                 590
Thr Glu Asn Leu Pro Asp Tyr Met Lys Leu Cys Tyr Gln Ile Tyr Tyr
        595                 600                 605
Asp Ile Val His Glu Val Ala Trp Glu Ala Lys Glu Gln Gly Arg
    610                 615                 620
Glu Leu Val Ser Phe Phe Arg Lys Gly Trp Glu Asp Tyr Leu Leu Gly
625                 630                 635                 640
Tyr Tyr Glu Glu Ala Glu Trp Leu Ala Ala Glu Tyr Val Pro Thr Leu
                645                 650                 655
Asp Glu Tyr Ile Lys Asn Gly Ile Thr Ser Ile Gly Gln Arg Ile Leu
            660                 665                 670
Leu Leu Ser Gly Val Leu Ile Met Asp Gly Gln Leu Leu Ser Gln Glu
        675                 680                 685
Ala Leu Glu Lys Val Asp Tyr Pro Gly Arg Arg Val Leu Thr Glu Leu
    690                 695                 700
Asn Ser Leu Ile Ser Arg Leu Ala Asp Asp Thr Lys Thr Tyr Lys Ala
705                 710                 715                 720
Glu Lys Ala Arg Gly Glu Leu Ala Ser Ser Ile Glu Cys Tyr Met Lys
                725                 730                 735
Asp His Pro Glu Cys Thr Glu Glu Ala Leu Asp His Ile Tyr Ser
            740                 745                 750
Ile Leu Glu Pro Ala Val Lys Glu Leu Thr Arg Glu Phe Leu Lys Pro
        755                 760                 765
```

```
Asp Asp Val Pro Phe Ala Cys Lys Lys Met Leu Phe Glu Glu Thr Arg
        770                 775                 780
Val Thr Met Val Ile Phe Lys Asp Gly Asp Gly Phe Gly Val Ser Lys
785                 790                 795                 800
Leu Glu Val Lys Asp His Ile Lys Glu Cys Leu Ile Glu Pro Leu Pro
                805                 810                 815
Leu

<210> SEQ ID NO 41
<211> LENGTH: 2528
<212> TYPE: DNA
<213> ORGANISM: Artificial Sequence
<220> FEATURE:
<223> OTHER INFORMATION: Description of Artificial Sequence:
      computer-generated nucleic acid sequence encoding
      E-alpha-bisabolene synthase
<221> NAME/KEY: CDS
<222> LOCATION: (1)..(2451)

<400> SEQUENCE: 41 atg gct ggc gtt tct gct gta tca aag gtt tcc agc ttg gtt tgt gat        48
Met Ala Gly Val Ser Ala Val Ser Lys Val Ser Ser Leu Val Cys Asp
  1               5                  10                  15 ttg tcg agt acc agc ggc ttg att cga aga act gcc aat cct cat ccc        96
Leu Ser Ser Thr Ser Gly Leu Ile Arg Arg Thr Ala Asn Pro His Pro
             20                  25                  30 aat gtc tgg ggt tat gat ctt gtg cat tct ctt aaa tca cct tat att       144
Asn Val Trp Gly Tyr Asp Leu Val His Ser Leu Lys Ser Pro Tyr Ile
         35                  40                  45 gat tct agt tac aga gaa cgc gcg gag gtc ctt gtt agc gag att aaa       192
Asp Ser Ser Tyr Arg Glu Arg Ala Glu Val Leu Val Ser Glu Ile Lys
     50                  55                  60 gcg atg ctt aat cca gct att aca gga gat gga gaa tca atg att act       240
Ala Met Leu Asn Pro Ala Ile Thr Gly Asp Gly Glu Ser Met Ile Thr
 65                  70                  75                  80 cca tct gct tat gac aca gca tgg gta gcg agg gtg ccc gcc att gat       288
Pro Ser Ala Tyr Asp Thr Ala Trp Val Ala Arg Val Pro Ala Ile Asp
                 85                  90                  95 ggc tct gct cgc ccg caa ttt ccc caa aca gtt gac tgg att ttg aaa       336
Gly Ser Ala Arg Pro Gln Phe Pro Gln Thr Val Asp Trp Ile Leu Lys
            100                 105                 110 aac cag tta aaa gat ggt tca tgg gga att cag tcc cac ttt ctg ctg       384
Asn Gln Leu Lys Asp Gly Ser Trp Gly Ile Gln Ser His Phe Leu Leu
        115                 120                 125 tcc gac cgt ctt ctt gcc act ctt tct tgt gtt ctt gtg ctc ctt aaa       432
Ser Asp Arg Leu Leu Ala Thr Leu Ser Cys Val Leu Val Leu Leu Lys
    130                 135                 140 tgg aac gtt ggg gat ctg caa gta gag cag gga att gaa ttc ata aag       480
Trp Asn Val Gly Asp Leu Gln Val Glu Gln Gly Ile Glu Phe Ile Lys
145                 150                 155                 160 act aat ctg gaa cta gta aag gat gaa acc gat caa gat agc ttg gta       528
Thr Asn Leu Glu Leu Val Lys Asp Glu Thr Asp Gln Asp Ser Leu Val
                165                 170                 175 aca gac ttt gag atc ata ttt cct tct ctg tta aga gaa gct caa tct       576
Thr Asp Phe Glu Ile Ile Phe Pro Ser Leu Leu Arg Glu Ala Gln Ser
            180                 185                 190 ctg cgc ctc gga ctt ccc tac gac ctg cct tat ata cat ctg ttg cag       624
Leu Arg Leu Gly Leu Pro Tyr Asp Leu Pro Tyr Ile His Leu Leu Gln
        195                 200                 205 act aaa cgg cag gaa aga tta gca aaa ctt tca agg gag gaa att tat       672
Thr Lys Arg Gln Glu Arg Leu Ala Lys Leu Ser Arg Glu Glu Ile Tyr
```

```
                210                     215                     220
gcg gtt ccg tcg cca ttg ttg tat tct tta gag gga ata caa gat ata      720
Ala Val Pro Ser Pro Leu Leu Tyr Ser Leu Glu Gly Ile Gln Asp Ile
225                     230                     235                 240 gtt gaa tgg gaa cga ata atg gaa gtt caa agt cag gat ggg tct ttc      768
Val Glu Trp Glu Arg Ile Met Glu Val Gln Ser Gln Asp Gly Ser Phe
                245                     250                     255 tta agc tca cct gct tct act gcc tgc gtt ttc atg cac aca gga gac      816
Leu Ser Ser Pro Ala Ser Thr Ala Cys Val Phe Met His Thr Gly Asp
                260                     265                     270 gcg aaa tgc ctt gaa ttc ttg aac agt gtg atg atc aag ttt gga aat      864
Ala Lys Cys Leu Glu Phe Leu Asn Ser Val Met Ile Lys Phe Gly Asn
        275                     280                     285 ttt gtt ccc tgc ctg tat cct gtg gat ctg ctg gaa cgc ctg ttg atc      912
Phe Val Pro Cys Leu Tyr Pro Val Asp Leu Leu Glu Arg Leu Leu Ile
        290                     295                     300 gta gat aat att gta cgc ctt gga atc tat aga cac ttt gaa aag gaa      960
Val Asp Asn Ile Val Arg Leu Gly Ile Tyr Arg His Phe Glu Lys Glu
305                     310                     315                 320 atc aag gaa gct ctt gat tat gtt tac agg cat tgg aac gaa aga gga     1008
Ile Lys Glu Ala Leu Asp Tyr Val Tyr Arg His Trp Asn Glu Arg Gly
                325                     330                     335 att ggg tgg ggc aga cta aat ccc ata gca gat ctt gag acc act gct     1056
Ile Gly Trp Gly Arg Leu Asn Pro Ile Ala Asp Leu Glu Thr Thr Ala
                340                     345                     350 ttg gga ttt cga ttg ctt cgg ctg cat agg tac aat gta tct cca gcc     1104
Leu Gly Phe Arg Leu Leu Arg Leu His Arg Tyr Asn Val Ser Pro Ala
                355                     360                     365 att ttt gac aac ttc aaa gat gcc aat ggg aaa ttc att tgc tcg acc     1152
Ile Phe Asp Asn Phe Lys Asp Ala Asn Gly Lys Phe Ile Cys Ser Thr
370                     375                     380 ggt caa ttc aac aaa gat gta gca agc atg ctg aat ctt tat aga gct     1200
Gly Gln Phe Asn Lys Asp Val Ala Ser Met Leu Asn Leu Tyr Arg Ala
385                     390                     395                 400 tcc cag ctc gca ttt ccc gga gaa aac att ctt gat gaa gct aaa agc     1248
Ser Gln Leu Ala Phe Pro Gly Glu Asn Ile Leu Asp Glu Ala Lys Ser
                405                     410                     415 ttc gct act aaa tat ttg aga gaa gct ctt gag aaa agt gag act tcc     1296
Phe Ala Thr Lys Tyr Leu Arg Glu Ala Leu Glu Lys Ser Glu Thr Ser
                420                     425                     430 agt gca tgg aac aac aaa caa aac ctg agc caa gag atc aaa tac gcg     1344
Ser Ala Trp Asn Asn Lys Gln Asn Leu Ser Gln Glu Ile Lys Tyr Ala
        435                     440                     445 ctg aag act tct tgg cat gcc agt gtt ccg aga gtg gaa gca aag aga     1392
Leu Lys Thr Ser Trp His Ala Ser Val Pro Arg Val Glu Ala Lys Arg
        450                     455                     460 tac tgt caa gtg tat cgc cca gat tat gca cgc ata gca aaa tgc gtt     1440
Tyr Cys Gln Val Tyr Arg Pro Asp Tyr Ala Arg Ile Ala Lys Cys Val
465                     470                     475                 480 tac aag cta ccc tac gtg aac aat gaa aag ttt tta gag ctg gga aaa     1488
Tyr Lys Leu Pro Tyr Val Asn Asn Glu Lys Phe Leu Glu Leu Gly Lys
                485                     490                     495 tta gat ttc aac att atc cag tcc atc cac caa gaa gaa atg aag aat     1536
Leu Asp Phe Asn Ile Ile Gln Ser Ile His Gln Glu Glu Met Lys Asn
                500                     505                     510 gtt acc agc tgg ttt aga gat tcg ggg ttg cca cta ttc acc ttc gct     1584
Val Thr Ser Trp Phe Arg Asp Ser Gly Leu Pro Leu Phe Thr Phe Ala
                515                     520                     525 cgg gag agg ccg ctg gaa ttc tac ttc tta gta gcg gcg ggg acc tat     1632
```

-continued

| | | | | | | | | | | | | |
|---|---|---|---|---|---|---|---|---|---|---|---|---|
| Arg | Glu | Arg | Pro | Leu | Glu | Phe | Tyr | Phe | Leu | Val | Ala | Ala | Gly | Thr | Tyr |
| | 530 | | | | 535 | | | | 540 | | | | | | |

```
gaa ccc cag tat gcc aaa tgc agg ttc ctc ttt aca aaa gtg gca tgc    1680
Glu Pro Gln Tyr Ala Lys Cys Arg Phe Leu Phe Thr Lys Val Ala Cys
545                 550                 555                 560 ttg cag act gtt ctg gac gat atg tat gac act tat gga acc cta gat    1728
Leu Gln Thr Val Leu Asp Asp Met Tyr Asp Thr Tyr Gly Thr Leu Asp
                565                 570                 575 gaa ttg aag cta ttc act gag gct gtg aga aga tgg gac ctc tcc ttt    1776
Glu Leu Lys Leu Phe Thr Glu Ala Val Arg Arg Trp Asp Leu Ser Phe
            580                 585                 590 aca gaa aac ctt cca gac tat atg aaa cta tgt tac caa atc tat tat    1824
Thr Glu Asn Leu Pro Asp Tyr Met Lys Leu Cys Tyr Gln Ile Tyr Tyr
        595                 600                 605 gac ata gtt cac gag gtg gct tgg gag gca gag aag gaa cag ggg cgt    1872
Asp Ile Val His Glu Val Ala Trp Glu Ala Glu Lys Glu Gln Gly Arg
    610                 615                 620 gaa ttg gtc agc ttt ttc aga aag gga tgg gag gat tat ctt ctg ggt    1920
Glu Leu Val Ser Phe Phe Arg Lys Gly Trp Glu Asp Tyr Leu Leu Gly
625                 630                 635                 640 tat tat gaa gaa gct gaa tgg tta gct gct gag tat gtg cct acc ttg    1968
Tyr Tyr Glu Glu Ala Glu Trp Leu Ala Ala Glu Tyr Val Pro Thr Leu
                645                 650                 655 gac gag tac ata aag aat gga atc aca tct atc ggc caa cgt ata ctt    2016
Asp Glu Tyr Ile Lys Asn Gly Ile Thr Ser Ile Gly Gln Arg Ile Leu
            660                 665                 670 ctg ttg agt gga gtg ttg ata atg gat ggg caa ctc ctt tcg caa gag    2064
Leu Leu Ser Gly Val Leu Ile Met Asp Gly Gln Leu Leu Ser Gln Glu
        675                 680                 685 gca tta gag aaa gta gat tat cca gga aga cgt gtt ctc aca gag ctg    2112
Ala Leu Glu Lys Val Asp Tyr Pro Gly Arg Arg Val Leu Thr Glu Leu
    690                 695                 700 aat agc ctc att tcc cgc ctg gcg gat gac acg aag aca tat aaa gct    2160
Asn Ser Leu Ile Ser Arg Leu Ala Asp Asp Thr Lys Thr Tyr Lys Ala
705                 710                 715                 720 gag aag gct cgt gga gaa ttg gcg tcc agc att gaa tgt tac atg aaa    2208
Glu Lys Ala Arg Gly Glu Leu Ala Ser Ser Ile Glu Cys Tyr Met Lys
                725                 730                 735 gac cat cct gaa tgt aca gag gaa gag gct ctc gat cac atc tat agc    2256
Asp His Pro Glu Cys Thr Glu Glu Glu Ala Leu Asp His Ile Tyr Ser
            740                 745                 750 att ctg gag ccg gcg gtg aag gaa ctg aca aga gag ttt ctg aag ccc    2304
Ile Leu Glu Pro Ala Val Lys Glu Leu Thr Arg Glu Phe Leu Lys Pro
        755                 760                 765 gac gac gtc cca ttc gcc tgc aag aag atg ctt ttc gag gag aca aga    2352
Asp Asp Val Pro Phe Ala Cys Lys Lys Met Leu Phe Glu Glu Thr Arg
770                 775                 780 gtg acg atg gtg ata ttc aag gat gga gat gga ttc ggt gtt tcc aaa    2400
Val Thr Met Val Ile Phe Lys Asp Gly Asp Gly Phe Gly Val Ser Lys
                785                 790                 795                 800 tta gaa gtc aaa gat cat atc aaa gag tgt ctc att gaa ccg ctg cca    2448
Leu Glu Val Lys Asp His Ile Lys Glu Cys Leu Ile Glu Pro Leu Pro
                805                 810                 815 ctg taatcaaaat agttgcaata ataattgaaa taatctcaac tatgtttcac        2501
Leu aaaaaaaaaa aaaaaaaaaa aaaaaaa                                    2528

<210> SEQ ID NO 42
<211> LENGTH: 817
```

```
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 42
```

Met Ala Gly Val Ser Ala Val Ser Lys Val Ser Ser Leu Val Cys Asp
 1               5                  10                  15

Leu Ser Ser Thr Ser Gly Leu Ile Arg Arg Thr Ala Asn Pro His Pro
            20                  25                  30

Asn Val Trp Gly Tyr Asp Leu Val His Ser Leu Lys Ser Pro Tyr Ile
        35                  40                  45

Asp Ser Ser Tyr Arg Glu Arg Ala Glu Val Leu Val Ser Glu Ile Lys
    50                  55                  60

Ala Met Leu Asn Pro Ala Ile Thr Gly Asp Gly Glu Ser Met Ile Thr
65                  70                  75                  80

Pro Ser Ala Tyr Asp Thr Ala Trp Val Ala Arg Val Pro Ala Ile Asp
                85                  90                  95

Gly Ser Ala Arg Pro Gln Phe Pro Gln Thr Val Asp Trp Ile Leu Lys
            100                 105                 110

Asn Gln Leu Lys Asp Gly Ser Trp Gly Ile Gln Ser His Phe Leu Leu
        115                 120                 125

Ser Asp Arg Leu Leu Ala Thr Leu Ser Cys Val Leu Val Leu Leu Lys
    130                 135                 140

Trp Asn Val Gly Asp Leu Gln Val Glu Gln Gly Ile Glu Phe Ile Lys
145                 150                 155                 160

Thr Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
            180                 185                 190

Leu Arg Leu Gly Leu Pro Tyr Asp Leu Pro Tyr Ile His Leu Leu Gln
        195                 200                 205

Thr Lys Arg Gln Glu Arg Leu Ala Lys Leu Ser Arg Glu Glu Ile Tyr
    210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
                245                 250                 255

Leu Ser Ser Pro Ala Ser Thr Ala Cys Val Phe Met His Thr Gly Asp
            260                 265                 270

Ala Lys Cys Leu Glu Phe Leu Asn Ser Val Met Ile Lys Phe Gly Asn
        275                 280                 285

Phe Val Pro Cys Leu Tyr Pro Val Asp Leu Leu Glu Arg Leu Leu Ile
    290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
                325                 330                 335

Ile Gly Trp Gly Arg Leu Asn Pro Ile Ala Asp Leu Glu Thr Thr Ala
            340                 345                 350

Leu Gly Phe Arg Leu Leu Arg Leu His Arg Tyr Asn Val Ser Pro Ala
        355                 360                 365

-continued

```
Ile Phe Asp Asn Phe Lys Asp Ala Asn Gly Lys Phe Ile Cys Ser Thr
    370                 375                 380
Gly Gln Phe Asn Lys Asp Val Ala Ser Met Leu Asn Leu Tyr Arg Ala
385                 390                 395                 400
Ser Gln Leu Ala Phe Pro Gly Glu Asn Ile Leu Asp Glu Ala Lys Ser
                405                 410                 415
Phe Ala Thr Lys Tyr Leu Arg Glu Ala Leu Glu Lys Ser Glu Thr Ser
            420                 425                 430
Ser Ala Trp Asn Lys Gln Asn Leu Ser Gln Glu Ile Lys Tyr Ala
        435                 440                 445
Leu Lys Thr Ser Trp His Ala Ser Val Pro Arg Val Glu Ala Lys Arg
    450                 455                 460
Tyr Cys Gln Val Tyr Arg Pro Asp Tyr Ala Arg Ile Ala Lys Cys Val
465                 470                 475                 480
Tyr Lys Leu Pro Tyr Val Asn Asn Glu Lys Phe Leu Glu Leu Gly Lys
                485                 490                 495
Leu Asp Phe Asn Ile Ile Gln Ser Ile His Gln Glu Met Lys Asn
            500                 505                 510
Val Thr Ser Trp Phe Arg Asp Ser Gly Leu Pro Leu Phe Thr Phe Ala
        515                 520                 525
Arg Glu Arg Pro Leu Glu Phe Tyr Phe Leu Val Ala Ala Gly Thr Tyr
    530                 535                 540
Glu Pro Gln Tyr Ala Lys Cys Arg Phe Leu Phe Thr Lys Val Ala Cys
545                 550                 555                 560
Leu Gln Thr Val Leu Asp Asp Met Tyr Asp Thr Tyr Gly Thr Leu Asp
                565                 570                 575
Glu Leu Lys Leu Phe Thr Glu Ala Val Arg Arg Trp Asp Leu Ser Phe
            580                 585                 590
Thr Glu Asn Leu Pro Asp Tyr Met Lys Leu Cys Tyr Gln Ile Tyr Tyr
        595                 600                 605
Asp Ile Val His Glu Val Ala Trp Glu Ala Lys Glu Gln Gly Arg
    610                 615                 620
Glu Leu Val Ser Phe Phe Arg Lys Gly Trp Glu Asp Tyr Leu Leu Gly
625                 630                 635                 640
Tyr Tyr Glu Glu Ala Glu Trp Leu Ala Ala Glu Tyr Val Pro Thr Leu
                645                 650                 655
Asp Glu Tyr Ile Lys Asn Gly Ile Thr Ser Ile Gly Gln Arg Ile Leu
            660                 665                 670
Leu Leu Ser Gly Val Leu Ile Met Asp Gly Gln Leu Leu Ser Gln Glu
        675                 680                 685
Ala Leu Glu Lys Val Asp Tyr Pro Gly Arg Arg Val Leu Thr Glu Leu
    690                 695                 700
Asn Ser Leu Ile Ser Arg Leu Ala Asp Asp Thr Lys Thr Tyr Lys Ala
705                 710                 715                 720
Glu Lys Ala Arg Gly Glu Leu Ala Ser Ser Ile Glu Cys Tyr Met Lys
                725                 730                 735
Asp His Pro Glu Cys Thr Glu Glu Ala Leu Asp His Ile Tyr Ser
            740                 745                 750
Ile Leu Glu Pro Ala Val Lys Glu Leu Thr Arg Glu Phe Leu Lys Pro
        755                 760                 765
Asp Asp Val Pro Phe Ala Cys Lys Lys Met Leu Phe Glu Glu Thr Arg
    770                 775                 780
```

```
Val Thr Met Val Ile Phe Lys Asp Gly Asp Gly Phe Gly Val Ser Lys
785                 790                 795                 800

Leu Glu Val Lys Asp His Ile Lys Glu Cys Leu Ile Glu Pro Leu Pro
                805                 810                 815

Leu

<210> SEQ ID NO 43
<211> LENGTH: 1885
<212> TYPE: DNA
<213> ORGANISM: Artificial Sequence
<220> FEATURE:
<223> OTHER INFORMATION: Description of Artificial Sequence:
      computer-generated nucleic acid sequence encoding
      delta selinene synthase
<221> NAME/KEY: CDS
<222> LOCATION: (21)..(1763)

<400> SEQUENCE: 43
cggatctggt ttcgcgatcc atg gct gag att tca gaa tct tcc atc cct cga        53
                     Met Ala Glu Ile Ser Glu Ser Ser Ile Pro Arg
                      1               5                  10 cgc aca ggg aat cat cac gga aat gtg tgg gac gat gac ctc ata cac        101
Arg Thr Gly Asn His His Gly Asn Val Trp Asp Asp Asp Leu Ile His
             15                  20                  25 tct ctc aac tcg ccc ttt ggg gca cct gca tat tat gag ctc ctt caa        149
Ser Leu Asn Ser Pro Phe Gly Ala Pro Ala Tyr Tyr Glu Leu Leu Gln
         30                  35                  40 aag ctt att cag gag atc aag cat tta ctt ttg act gaa atg gaa atg        197
Lys Leu Ile Gln Glu Ile Lys His Leu Leu Leu Thr Glu Met Glu Met
     45                  50                  55 gat gat ggc gat cat gat tta atc aaa cgt ctt cag atc gtt gac act        245
Asp Asp Gly Asp His Asp Leu Ile Lys Arg Leu Gln Ile Val Asp Thr
 60                  65                  70                  75 ttg gaa tgc ctg gga atc gat aga cat ttt gaa cac gaa ata caa aca        293
Leu Glu Cys Leu Gly Ile Asp Arg His Phe Glu His Glu Ile Gln Thr
                 80                  85                  90 gct gct tta gat tac gtt tac aga tgg tgg aac gaa aaa ggt atc ggg        341
Ala Ala Leu Asp Tyr Val Tyr Arg Trp Trp Asn Glu Lys Gly Ile Gly
             95                 100                 105 gag gga tca aga gat tcc ttc agc aaa gat ctg aac gct acg gct tta        389
Glu Gly Ser Arg Asp Ser Phe Ser Lys Asp Leu Asn Ala Thr Ala Leu
        110                 115                 120 gga ttt cgc gct ctc cga ctg cat cga tat aac gta tcg tca ggt gtg        437
Gly Phe Arg Ala Leu Arg Leu His Arg Tyr Asn Val Ser Ser Gly Val
    125                 130                 135 ttg aag aat ttc aag gat gaa aac ggg aag ttc ttc tgc aac ttt act        485
Leu Lys Asn Phe Lys Asp Glu Asn Gly Lys Phe Phe Cys Asn Phe Thr
140                 145                 150                 155 ggt gaa gaa gga aga gga gat aaa caa gtg aga agc atg ttg tcg tta        533
Gly Glu Glu Gly Arg Gly Asp Lys Gln Val Arg Ser Met Leu Ser Leu
                160                 165                 170 ctt cga gct tca gag att tcg ttt ccc gga gaa aaa gtg atg gaa gag        581
Leu Arg Ala Ser Glu Ile Ser Phe Pro Gly Glu Lys Val Met Glu Glu
            175                 180                 185 gcc aag gca ttc aca aga gaa tat cta aac caa gtt tta gct gga cac        629
Ala Lys Ala Phe Thr Arg Glu Tyr Leu Asn Gln Val Leu Ala Gly His
        190                 195                 200 ggg gat gtg act gac gtg gat caa agc ctt ttg aga gag gtg aag tac        677
Gly Asp Val Thr Asp Val Asp Gln Ser Leu Leu Arg Glu Val Lys Tyr
    205                 210                 215 gca ttg gag ttt cca tgg cat tgc agt gtg ccg aga tgg gag gca agg        725
```

```
                Ala Leu Glu Phe Pro Trp His Cys Ser Val Pro Arg Trp Glu Ala Arg
                220                 225                 230                 235 agc ttt ctc gaa ata tat gga cac aac cat tcg tgg ctc aag tcg aat              773
Ser Phe Leu Glu Ile Tyr Gly His Asn His Ser Trp Leu Lys Ser Asn
                    240                 245                 250 atc aac caa aaa atg ttg aag tta gcc aaa ttg gac ttc aat att ctg              821
Ile Asn Gln Lys Met Leu Lys Leu Ala Lys Leu Asp Phe Asn Ile Leu
                255                 260                 265 caa tgc aaa cat cac aag gag ata cag ttt att aca agg tgg tgg aga              869
Gln Cys Lys His His Lys Glu Ile Gln Phe Ile Thr Arg Trp Trp Arg
            270                 275                 280 gac tcg ggt ata tcg cag ctg aat ttc tat cga aag cga cac gtg gaa              917
Asp Ser Gly Ile Ser Gln Leu Asn Phe Tyr Arg Lys Arg His Val Glu
        285                 290                 295 tat tat tct tgg gtt gtt atg tgc att ttt gag cca gag ttc tct gaa              965
Tyr Tyr Ser Trp Val Val Met Cys Ile Phe Glu Pro Glu Phe Ser Glu
300                 305                 310                 315 agt aga att gcc ttc gcc aaa act gct atc ctg tgt act gtt cta gat             1013
Ser Arg Ile Ala Phe Ala Lys Thr Ala Ile Leu Cys Thr Val Leu Asp
                    320                 325                 330 gac ctc tat gat acg cac gca aca ttg cat gaa atc aaa atc atg aca             1061
Asp Leu Tyr Asp Thr His Ala Thr Leu His Glu Ile Lys Ile Met Thr
                335                 340                 345 gag gga gtg aga cga tgg gat ctt tcg ttg aca gat gac ctc cca gac             1109
Glu Gly Val Arg Arg Trp Asp Leu Ser Leu Thr Asp Asp Leu Pro Asp
            350                 355                 360 tac att aaa att gca ttc cag ttc ttc ttc aat aca gtg aat gaa ttg             1157
Tyr Ile Lys Ile Ala Phe Gln Phe Phe Phe Asn Thr Val Asn Glu Leu
365                 370                 375 ata gtt gaa atc gtg aaa cgg caa ggg cgg gat atg aca acc ata gtt             1205
Ile Val Glu Ile Val Lys Arg Gln Gly Arg Asp Met Thr Thr Ile Val
380                 385                 390                 395 aaa gat tgc tgg aag cga tac att gag tct tat ctg caa gaa gcg gaa             1253
Lys Asp Cys Trp Lys Arg Tyr Ile Glu Ser Tyr Leu Gln Glu Ala Glu
                    400                 405                 410 tgg ata gca act gga cat att ccc act ttt aac gaa tac ata aag aac             1301
Trp Ile Ala Thr Gly His Ile Pro Thr Phe Asn Glu Tyr Ile Lys Asn
                415                 420                 425 ggc atg gct agc tca ggg atg tgt att cta aat ttg aat cca ctt ctc             1349
Gly Met Ala Ser Ser Gly Met Cys Ile Leu Asn Leu Asn Pro Leu Leu
            430                 435                 440 ttg ttg gat aaa ctt ctc ccc gac aac att ctg gag caa ata cat tct             1397
Leu Leu Asp Lys Leu Leu Pro Asp Asn Ile Leu Glu Gln Ile His Ser
        445                 450                 455 cca tcc aag atc ctg gac ctc tta gaa ttg acg ggc aga atc gcc gat             1445
Pro Ser Lys Ile Leu Asp Leu Leu Glu Leu Thr Gly Arg Ile Ala Asp
460                 465                 470                 475 gac tta aaa gat ttc gag gac gag aag gaa cgc ggg gag atg gct tca             1493
Asp Leu Lys Asp Phe Glu Asp Glu Lys Glu Arg Gly Glu Met Ala Ser
                    480                 485                 490 tct tta cag tgt tat atg aaa gaa aat cct gaa tct aca gtg gaa aat             1541
Ser Leu Gln Cys Tyr Met Lys Glu Asn Pro Glu Ser Thr Val Glu Asn
                495                 500                 505 gct tta aat cac ata aaa ggc atc ctt aat cgt tcc ctt gag gaa ttt             1589
Ala Leu Asn His Ile Lys Gly Ile Leu Asn Arg Ser Leu Glu Glu Phe
            510                 515                 520 aat tgg gag ttt atg aag cag gat agt gtc cca atg tgt tgc aag aaa             1637
Asn Trp Glu Phe Met Lys Gln Asp Ser Val Pro Met Cys Cys Lys Lys
        525                 530                 535
```

```
ttc act ttc aat ata ggt cga gga ctt caa ttc atc tac aaa tac aga         1685
Phe Thr Phe Asn Ile Gly Arg Gly Leu Gln Phe Ile Tyr Lys Tyr Arg
540                 545                 550                 555 gac ggc tta tac att tct gac aag gaa gta aag gac cag ata ttc aaa         1733
Asp Gly Leu Tyr Ile Ser Asp Lys Glu Val Lys Asp Gln Ile Phe Lys
                560                 565                 570 att cta gtc cac caa gtt cca atg gag gaa tagtgatggt cttggttgta          1783
Ile Leu Val His Gln Val Pro Met Glu Glu
                575                 580 gttgtctatt atggtatatt gcattgacat ttatgcttaa aggtgtttct taaacgttta       1843
gggcggaccg ttaaataagt tggcaataat taatatctcg ag                         1885

<210> SEQ ID NO 44
<211> LENGTH: 581
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 44

Met Ala Glu Ile Ser Glu Ser Ser Ile Pro Arg Arg Thr Gly Asn His
  1               5                  10                  15

His Gly Asn Val Trp Asp Asp Leu Ile His Ser Leu Asn Ser Pro
                 20                  25                  30

Phe Gly Ala Pro Ala Tyr Tyr Glu Leu Leu Gln Lys Leu Ile Gln Glu
             35                  40                  45

Ile Lys His Leu Leu Leu Thr Glu Met Glu Met Asp Asp Gly Asp His
 50                  55                  60

Asp Leu Ile Lys Arg Leu Gln Ile Val Asp Thr Leu Glu Cys Leu Gly
 65                  70                  75                  80

Ile Asp Arg His Phe Glu His Glu Ile Gln Thr Ala Ala Leu Asp Tyr
                 85                  90                  95

Val Tyr Arg Trp Trp Asn Glu Lys Gly Ile Gly Glu Gly Ser Arg Asp
            100                 105                 110

Ser Phe Ser Lys Asp Leu Asn Ala Thr Ala Leu Gly Phe Arg Ala Leu
        115                 120                 125

Arg Leu His Arg Tyr Asn Val Ser Ser Gly Val Leu Lys Asn Phe Lys
    130                 135                 140

Asp Glu Asn Gly Lys Phe Phe Cys Asn Phe Thr Gly Glu Glu Gly Arg
145                 150                 155                 160

Gly Asp Lys Gln Val Arg Ser Met Leu Ser Leu Leu Arg Ala Ser Glu
                165                 170                 175

Ile Ser Phe Pro Gly Glu Lys Val Met Glu Glu Ala Lys Ala Phe Thr
            180                 185                 190

Arg Glu Tyr Leu Asn Gln Val Leu Ala Gly His Gly Asp Val Thr Asp
        195                 200                 205

Val Asp Gln Ser Leu Leu Arg Glu Val Lys Tyr Ala Leu Glu Phe Pro
    210                 215                 220

Trp His Cys Ser Val Pro Arg Trp Glu Ala Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
```

-continued

```
                        260                 265                 270
Lys Glu Ile Gln Phe Ile Thr Arg Trp Trp Arg Asp Ser Gly Ile Ser
        275                 280                 285
Gln Leu Asn Phe Tyr Arg Lys Arg His Val Glu Tyr Tyr Ser Trp Val
    290                 295                 300
Val Met Cys Ile Phe Glu Pro Glu Phe Ser Glu Ser Arg Ile Ala Phe
305                 310                 315                 320
Ala Lys Thr Ala Ile Leu Cys Thr Val Leu Asp Asp Leu Tyr Asp Thr
                325                 330                 335
His Ala Thr Leu His Glu Ile Lys Ile Met Thr Glu Gly Val Arg Arg
                340                 345                 350
Trp Asp Leu Ser Leu Thr Asp Asp Leu Pro Asp Tyr Ile Lys Ile Ala
            355                 360                 365
Phe Gln Phe Phe Phe Asn Thr Val Asn Glu Leu Ile Val Glu Ile Val
370                 375                 380
Lys Arg Gln Gly Arg Asp Met Thr Thr Ile Val Lys Asp Cys Trp Lys
385                 390                 395                 400
Arg Tyr Ile Glu Ser Tyr Leu Gln Glu Ala Glu Trp Ile Ala Thr Gly
                405                 410                 415
His Ile Pro Thr Phe Asn Glu Tyr Ile Lys Asn Gly Met Ala Ser Ser
            420                 425                 430
Gly Met Cys Ile Leu Asn Leu Asn Pro Leu Leu Leu Asp Lys Leu
        435                 440                 445
Leu Pro Asp Asn Ile Leu Glu Gln Ile His Ser Pro Ser Lys Ile Leu
    450                 455                 460
Asp Leu Leu Glu Leu Thr Gly Arg Ile Ala Asp Asp Leu Lys Asp Phe
465                 470                 475                 480
Glu Asp Glu Lys Glu Arg Gly Glu Met Ala Ser Ser Leu Gln Cys Tyr
                485                 490                 495
Met Lys Glu Asn Pro Glu Ser Thr Val Glu Asn Ala Leu Asn His Ile
                500                 505                 510
Lys Gly Ile Leu Asn Arg Ser Leu Glu Glu Phe Asn Trp Glu Phe Met
        515                 520                 525
Lys Gln Asp Ser Val Pro Met Cys Cys Lys Lys Phe Thr Phe Asn Ile
    530                 535                 540
Gly Arg Gly Leu Gln Phe Ile Tyr Lys Tyr Arg Asp Gly Leu Tyr Ile
545                 550                 555                 560
Ser Asp Lys Glu Val Lys Asp Gln Ile Phe Lys Ile Leu Val His Gln
                565                 570                 575
Val Pro Met Glu Glu
            580
```

<210> SEQ ID NO 45
<211> LENGTH: 1885
<212> TYPE: DNA
<213> ORGANISM: Artificial Sequence
<220> FEATURE:
<223> OTHER INFORMATION: Description of Artificial Sequence:
      computer-generated sequence encoding delta
      selinene synthase
<221> NAME/KEY: CDS
<222> LOCATION: (24)..(1766)

<400> SEQUENCE: 45

```
cggatctggt tccgcgtgga tcc atg gct gag att tct gaa tct tcc atc cct      53
                       Met Ala Glu Ile Ser Glu Ser Ser Ile Pro
                         1               5                  10
```

```
cga cgc aca ggg aat cat cac gga aat gtg tgg gac gat gac ctc ata      101
Arg Arg Thr Gly Asn His His Gly Asn Val Trp Asp Asp Asp Leu Ile
            15                  20                  25 cac tct ctc aac tcg ccc tat ggg gca cct gca tat tat gag ctc ctt      149
His Ser Leu Asn Ser Pro Tyr Gly Ala Pro Ala Tyr Tyr Glu Leu Leu
        30                  35                  40 caa aag ctt att cag gag atc aag cat tta ctt ttg act gaa atg gaa      197
Gln Lys Leu Ile Gln Glu Ile Lys His Leu Leu Leu Thr Glu Met Glu
            45                  50                  55 atg gat gat ggc gat cat gat tta atc aaa cgt ctt cag atc gtt gac      245
Met Asp Asp Gly Asp His Asp Leu Ile Lys Arg Leu Gln Ile Val Asp
        60                  65                  70 act ttg gaa tgc ctg gga atc gat aga cat ttt gaa cac gaa ata caa      293
Thr Leu Glu Cys Leu Gly Ile Asp Arg His Phe Glu His Glu Ile Gln
75                  80                  85                  90 aca gct gtt tta gat tac gtt tac aga tgg tgg aac gaa aaa ggt atc      341
Thr Ala Val Leu Asp Tyr Val Tyr Arg Trp Trp Asn Glu Lys Gly Ile
                95                  100                 105 ggg gag gga tca aga gat tcc ttc agc aaa gat ctg aac gct acg gct      389
Gly Glu Gly Ser Arg Asp Ser Phe Ser Lys Asp Leu Asn Ala Thr Ala
            110                 115                 120 tta gga ttt cgc gct ctc cga ctg cat cga tat aac gta tcg tca ggt      437
Leu Gly Phe Arg Ala Leu Arg Leu His Arg Tyr Asn Val Ser Ser Gly
        125                 130                 135 gtg ttg aag aat ttc aag gat gaa aac ggg aag ttc ttc tgc aac ttt      485
Val Leu Lys Asn Phe Lys Asp Glu Asn Gly Lys Phe Phe Cys Asn Phe
    140                 145                 150 act ggt gaa gaa gga aga gga gat aaa caa gtg aga agc atg ttg tcg      533
Thr Gly Glu Glu Gly Arg Gly Asp Lys Gln Val Arg Ser Met Leu Ser
155                 160                 165                 170 tta ctt cga gct tca gag att tcg ttt ccc gga gaa aaa gtg atg gaa      581
Leu Leu Arg Ala Ser Glu Ile Ser Phe Pro Gly Glu Lys Val Met Glu
                175                 180                 185 gag gcc aag gca ttc aca aga gaa tat cta aac caa gtt tta gct gga      629
Glu Ala Lys Ala Phe Thr Arg Glu Tyr Leu Asn Gln Val Leu Ala Gly
            190                 195                 200 cac ggg gat gtg act gac gtg gat caa agc ctt ttg aga gag gtg aag      677
His Gly Asp Val Thr Asp Val Asp Gln Ser Leu Leu Arg Glu Val Lys
        205                 210                 215 tac gca ttg gag ttt cca tgg cat tgc agt gtg ccg aga tgg gag gca      725
Tyr Ala Leu Glu Phe Pro Trp His Cys Ser Val Pro Arg Trp Glu Ala
    220                 225                 230 agg agc ttt ctc gaa ata tat gga cac aac cat tcg tgg ctc aag tcg      773
Arg Ser Phe Leu Glu Ile Tyr Gly His Asn His Ser Trp Leu Lys Ser
235                 240                 245                 250 aat atc aac caa aaa atg ttg aag tta gcc aaa ttg gac ttc aat att      821
Asn Ile Asn Gln Lys Met Leu Lys Leu Ala Lys Leu Asp Phe Asn Ile
                255                 260                 265 ctg caa tgc aaa cat cac aag gag ata cag ttt att aca agg tgg tgg      869
Leu Gln Cys Lys His His Lys Glu Ile Gln Phe Ile Thr Arg Trp Trp
            270                 275                 280 aga gac tcg ggt ata tcg cag ctg aat ttc tat cga aag cga cac gtg      917
Arg Asp Ser Gly Ile Ser Gln Leu Asn Phe Tyr Arg Lys Arg His Val
        285                 290                 295 gaa tat tat tct tgg gtt gtt atg tgc att ttt gag cca gag ttc tct      965
Glu Tyr Tyr Ser Trp Val Val Met Cys Ile Phe Glu Pro Glu Phe Ser
    300                 305                 310 gaa agt aga att gcc ttc gcc aaa act gct atc ctg tgt act gtt cta     1013
Glu Ser Arg Ile Ala Phe Ala Lys Thr Ala Ile Leu Cys Thr Val Leu
```

```
                315                 320                 325                 330
gat gac ctc tat gat acg cac gca aca ttg cat gaa atc aaa atc atg    1061
Asp Asp Leu Tyr Asp Thr His Ala Thr Leu His Glu Ile Lys Ile Met
                    335                 340                 345 aca gag gga gtg aga cga tgg gat ctt tcg ttg aca gat gac ctc cca    1109
Thr Glu Gly Val Arg Arg Trp Asp Leu Ser Leu Thr Asp Asp Leu Pro
            350                 355                 360 gac tac att aaa att gca ttc cag ttc ttc ttc aat aca gtg aat gaa    1157
Asp Tyr Ile Lys Ile Ala Phe Gln Phe Phe Phe Asn Thr Val Asn Glu
        365                 370                 375 ttg ata gtt gaa atc gtg aaa cgg caa ggg cgg gat atg aca acc ata    1205
Leu Ile Val Glu Ile Val Lys Arg Gln Gly Arg Asp Met Thr Thr Ile
    380                 385                 390 gtt aaa gat tgc tgg aag cga tac att gag tct tat ctg caa gaa gcg    1253
Val Lys Asp Cys Trp Lys Arg Tyr Ile Glu Ser Tyr Leu Gln Glu Ala
395                 400                 405                 410 gaa tgg ata gca act gga cat att ccc act ttt aac gaa tac ata aag    1301
Glu Trp Ile Ala Thr Gly His Ile Pro Thr Phe Asn Glu Tyr Ile Lys
                415                 420                 425 aac ggc atg gct agc tca ggg atg tgt att cta aat ttg aat cca ctt    1349
Asn Gly Met Ala Ser Ser Gly Met Cys Ile Leu Asn Leu Asn Pro Leu
            430                 435                 440 ctc ttg ttg gat aaa ctt ctc ccc gac aac att ctg gag caa ata cat    1397
Leu Leu Leu Asp Lys Leu Leu Pro Asp Asn Ile Leu Glu Gln Ile His
        445                 450                 455 tct cca tcc aag atc ctg gac ctc tta gaa ttg acg ggc aga atc gcc    1445
Ser Pro Ser Lys Ile Leu Asp Leu Leu Glu Leu Thr Gly Arg Ile Ala
    460                 465                 470 gat gac tta aaa gat ttc gag gac gag aag gaa cgc ggg gag atg gct    1493
Asp Asp Leu Lys Asp Phe Glu Asp Glu Lys Glu Arg Gly Glu Met Ala
475                 480                 485                 490 tca tct tta cag tgt tat atg aaa gaa aat cct gaa tct aca gtg gaa    1541
Ser Ser Leu Gln Cys Tyr Met Lys Glu Asn Pro Glu Ser Thr Val Glu
                495                 500                 505 aat gct tta aat cac ata aaa ggc atc ctt aat cgt tcc ctt gag gaa    1589
Asn Ala Leu Asn His Ile Lys Gly Ile Leu Asn Arg Ser Leu Glu Glu
            510                 515                 520 ttt aat tgg gag ttt atg aag cag gat agt gtc cca atg tgt tgc aag    1637
Phe Asn Trp Glu Phe Met Lys Gln Asp Ser Val Pro Met Cys Cys Lys
        525                 530                 535 aaa ttc act ttc aat ata ggt cga gga ctt caa ttc atc tac aaa tac    1685
Lys Phe Thr Phe Asn Ile Gly Arg Gly Leu Gln Phe Ile Tyr Lys Tyr
    540                 545                 550 aga gac ggc tta tac att tct gac aag gaa gta aag gac cag ata ttc    1733
Arg Asp Gly Leu Tyr Ile Ser Asp Lys Glu Val Lys Asp Gln Ile Phe
555                 560                 565                 570 aaa att cta gtc cac caa gtt cca atg gag gaa tagtgatggt cttggttgta   1786
Lys Ile Leu Val His Gln Val Pro Met Glu Glu
                575                 580 gttgtctatt atggtatatt gcattgacat ttatgcttaa aggtgtttct taaacgttta   1846
gggcggaccg ttaaataagg caataattaa tatcacgag                          1885

<210> SEQ ID NO 46
<211> LENGTH: 581
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
```

<222> LOCATION: (1)..(817)
<223> OTHER INFORMATION: Computer-generated protein sequence

<400> SEQUENCE: 46

```
Met Ala Glu Ile Ser Glu Ser Ser Ile Pro Arg Arg Thr Gly Asn His
 1               5                  10                  15

His Gly Asn Val Trp Asp Asp Leu Ile His Ser Leu Asn Ser Pro
             20                  25                  30

Tyr Gly Ala Pro Ala Tyr Tyr Glu Leu Leu Gln Lys Leu Ile Gln Glu
             35                  40                  45

Ile Lys His Leu Leu Leu Thr Glu Met Glu Met Asp Asp Gly Asp His
 50                  55                  60

Asp Leu Ile Lys Arg Leu Gln Ile Val Asp Thr Leu Glu Cys Leu Gly
 65                  70                  75                  80

Ile Asp Arg His Phe Glu His Glu Ile Gln Thr Ala Val Leu Asp Tyr
                     85                  90                  95

Val Tyr Arg Trp Trp Asn Glu Lys Gly Ile Gly Glu Gly Ser Arg Asp
                100                 105                 110

Ser Phe Ser Lys Asp Leu Asn Ala Thr Ala Leu Gly Phe Arg Ala Leu
            115                 120                 125

Arg Leu His Arg Tyr Asn Val Ser Ser Gly Val Leu Lys Asn Phe Lys
130                 135                 140

Asp Glu Asn Gly Lys Phe Phe Cys Asn Phe Thr Gly Glu Glu Gly Arg
145                 150                 155                 160

Gly Asp Lys Gln Val Arg Ser Met Leu Ser Leu Arg Ala Ser Glu
                165                 170                 175

Ile Ser Phe Pro Gly Glu Lys Val Met Glu Glu Ala Lys Ala Phe Thr
            180                 185                 190

Arg Glu Tyr Leu Asn Gln Val Leu Ala Gly His Gly Asp Val Thr Asp
            195                 200                 205

Val Asp Gln Ser Leu Leu Arg Glu Val Lys Tyr Ala Leu Glu Phe Pro
210                 215                 220

Trp His Cys Ser Val Pro Arg Trp Glu Ala Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
            260                 265                 270

Lys Glu Ile Gln Phe Ile Thr Arg Trp Trp Arg Asp Ser Gly Ile Ser
        275                 280                 285

Gln Leu Asn Phe Tyr Arg Lys Arg His Val Glu Tyr Tyr Ser Trp Val
    290                 295                 300

Val Met Cys Ile Phe Glu Pro Glu Phe Ser Glu Ser Arg Ile Ala Phe
305                 310                 315                 320

Ala Lys Thr Ala Ile Leu Cys Thr Val Leu Asp Asp Leu Tyr Asp Thr
                325                 330                 335

His Ala Thr Leu His Glu Ile Lys Ile Met Thr Glu Gly Val Arg Arg
            340                 345                 350

Trp Asp Leu Ser Leu Thr Asp Leu Pro Asp Tyr Ile Lys Ile Ala
        355                 360                 365

Phe Gln Phe Phe Phe Asn Thr Val Asn Glu Leu Ile Val Glu Ile Val
    370                 375                 380

Lys Arg Gln Gly Arg Asp Met Thr Thr Ile Val Lys Asp Cys Trp Lys
385                 390                 395                 400
```

```
Arg Tyr Ile Glu Ser Tyr Leu Gln Glu Ala Glu Trp Ile Ala Thr Gly
                405                 410                 415
His Ile Pro Thr Phe Asn Glu Tyr Ile Lys Asn Gly Met Ala Ser Ser
            420                 425                 430
Gly Met Cys Ile Leu Asn Leu Asn Pro Leu Leu Leu Asp Lys Leu
        435                 440                 445
Leu Pro Asp Asn Ile Leu Glu Gln Ile His Ser Pro Ser Lys Ile Leu
    450                 455                 460
Asp Leu Leu Glu Leu Thr Gly Arg Ile Ala Asp Leu Lys Asp Phe
465                 470                 475                 480
Glu Asp Glu Lys Glu Arg Gly Glu Met Ala Ser Ser Leu Gln Cys Tyr
                485                 490                 495
Met Lys Glu Asn Pro Glu Ser Thr Val Glu Asn Ala Leu Asn His Ile
            500                 505                 510
Lys Gly Ile Leu Asn Arg Ser Leu Glu Glu Phe Asn Trp Glu Phe Met
        515                 520                 525
Lys Gln Asp Ser Val Pro Met Cys Cys Lys Lys Phe Thr Phe Asn Ile
    530                 535                 540
Gly Arg Gly Leu Gln Phe Ile Tyr Lys Tyr Arg Asp Gly Leu Tyr Ile
545                 550                 555                 560
Ser Asp Lys Glu Val Lys Asp Gln Ile Phe Lys Ile Leu Val His Gln
                565                 570                 575
Val Pro Met Glu Glu
            580

<210> SEQ ID NO 47
<211> LENGTH: 1885
<212> TYPE: DNA
<213> ORGANISM: Artificial Sequence
<220> FEATURE:
<223> OTHER INFORMATION: Description of Artificial Sequence:
      computer-generated nucleic acid sequence encoding
      delta selinene synthase
<221> NAME/KEY: CDS
<222> LOCATION: (24)..(1763)

<400> SEQUENCE: 47
cggatctggt tccgcgtgga tcc atg gct gag att tct gaa tcc atc cct cga      53
                        Met Ala Glu Ile Ser Glu Ser Ile Pro Arg
                          1               5                  10 cgc aca ggg aat cat cac gga aat gtg tgg gac gat gac ctc ata cac     101
Arg Thr Gly Asn His His Gly Asn Val Trp Asp Asp Asp Leu Ile His
             15                  20                  25 tct ctc aac tcg ccc tat ggg gca cct gca tat tat gag ctc ctt caa     149
Ser Leu Asn Ser Pro Tyr Gly Ala Pro Ala Tyr Tyr Glu Leu Leu Gln
         30                  35                  40 aag ctt att cag gag atc aag cat tta ctt ttg act gaa atg gaa atg     197
Lys Leu Ile Gln Glu Ile Lys His Leu Leu Leu Thr Glu Met Glu Met
     45                  50                  55 gat gat ggc gat cat gat tta atc aaa cgt ctt cag atc gtt gac act     245
Asp Asp Gly Asp His Asp Leu Ile Lys Arg Leu Gln Ile Val Asp Thr
 60                  65                  70 ttg gaa tgc ctg gga atc gat aga cat ttt gaa cac gaa ata caa aca     293
Leu Glu Cys Leu Gly Ile Asp Arg His Phe Glu His Glu Ile Gln Thr
 75                  80                  85                  90 gct gct tta gat tac gtt tac aga tgg tgg aac gaa aaa ggt atc ggg     341
Ala Ala Leu Asp Tyr Val Tyr Arg Trp Trp Asn Glu Lys Gly Ile Gly
                 95                 100                 105
```

```
                                                         -continued gag gga tca aga gat tcc ttc agc aaa gat ctg aac gct acg gct tta           389
Glu Gly Ser Arg Asp Ser Phe Ser Lys Asp Leu Asn Ala Thr Ala Leu
            110                 115                 120 gga ttt cgc gct ctc cga ctg cat cga tat aac gta tcg tca ggt gtg           437
Gly Phe Arg Ala Leu Arg Leu His Arg Tyr Asn Val Ser Ser Gly Val
        125                 130                 135 ttg aag aat ttc aag gat gaa aac ggg aag ttc ttc tgc aac ttt act           485
Leu Lys Asn Phe Lys Asp Glu Asn Gly Lys Phe Phe Cys Asn Phe Thr
140                 145                 150 ggt gaa gaa gga aga gga gat aaa caa gtg aga agc atg ttg tcg tta           533
Gly Glu Glu Gly Arg Gly Asp Lys Gln Val Arg Ser Met Leu Ser Leu
155                 160                 165                 170 ctt cga gct tca gag att tcg ttt ccc gga gaa aaa gtg atg gaa gag           581
Leu Arg Ala Ser Glu Ile Ser Phe Pro Gly Glu Lys Val Met Glu Glu
            175                 180                 185 gcc aag gca ttc aca aga gaa tat cta aac caa gtt tta gct gga cac           629
Ala Lys Ala Phe Thr Arg Glu Tyr Leu Asn Gln Val Leu Ala Gly His
        190                 195                 200 ggg gat gtg act gac gtg gat caa agc ctt ttg aga gag gtg aag tac           677
Gly Asp Val Thr Asp Val Asp Gln Ser Leu Leu Arg Glu Val Lys Tyr
    205                 210                 215 gca ttg gag ttt cca tgg cat tgc agt gtg ccg aga tgg gag gca agg           725
Ala Leu Glu Phe Pro Trp His Cys Ser Val Pro Arg Trp Glu Ala Arg
220                 225                 230 agc ttt ctc gaa ata tat gga cac aac cat tcg tgg ctc aag tcg aat           773
Ser Phe Leu Glu Ile Tyr Gly His Asn His Ser Trp Leu Lys Ser Asn
235                 240                 245                 250 atc aac caa aaa atg ttg aag tta gcc aaa ttg gac ttc aat att ctg           821
Ile Asn Gln Lys Met Leu Lys Leu Ala Lys Leu Asp Phe Asn Ile Leu
            255                 260                 265 caa tgc aaa cat cac aag gag ata cag ttt att aca agg tgg tgg aga           869
Gln Cys Lys His His Lys Glu Ile Gln Phe Ile Thr Arg Trp Trp Arg
        270                 275                 280 gac tcg ggt ata tcg cag ctg aat ttc tat cga aag cga cac gtg gaa           917
Asp Ser Gly Ile Ser Gln Leu Asn Phe Tyr Arg Lys Arg His Val Glu
    285                 290                 295 tat tat tct tgg gtt gtt atg tgc att ttt gag cca gag ttc tct gaa           965
Tyr Tyr Ser Trp Val Val Met Cys Ile Phe Glu Pro Glu Phe Ser Glu
300                 305                 310 agt aga att gcc ttc gcc aaa act gct atc ctg tgt act gtt cta gat          1013
Ser Arg Ile Ala Phe Ala Lys Thr Ala Ile Leu Cys Thr Val Leu Asp
315                 320                 325                 330 gac ctc tat gat acg cac gca aca ttg cat gaa atc aaa atc atg aca          1061
Asp Leu Tyr Asp Thr His Ala Thr Leu His Glu Ile Lys Ile Met Thr
            335                 340                 345 gag gga gtg aga cga tgg gat ctt tcg ttg aca gat gac ctc cca gac          1109
Glu Gly Val Arg Arg Trp Asp Leu Ser Leu Thr Asp Asp Leu Pro Asp
        350                 355                 360 tac att aaa att gca ttc cag ttc ttc ttc aat aca gtg aat gaa ttg          1157
Tyr Ile Lys Ile Ala Phe Gln Phe Phe Phe Asn Thr Val Asn Glu Leu
    365                 370                 375 ata gtt gaa atc gtg aaa cgg caa ggg cgg gat atg aca acc ata gtt          1205
Ile Val Glu Ile Val Lys Arg Gln Gly Arg Asp Met Thr Thr Ile Val
380                 385                 390 aaa gat tgc tgg aag cga tac att gag tct tat ctg caa gaa gcg gaa          1253
Lys Asp Cys Trp Lys Arg Tyr Ile Glu Ser Tyr Leu Gln Glu Ala Glu
395                 400                 405                 410 tgg ata gca act gga cat att ccc act ttt aac gaa tac ata aag aac          1301
Trp Ile Ala Thr Gly His Ile Pro Thr Phe Asn Glu Tyr Ile Lys Asn
            415                 420                 425
```

| | | | | | | | | | | | | | | | |
|---|---|---|---|---|---|---|---|---|---|---|---|---|---|---|---|
| ggc | atg | gct | agc | tca | ggg | atg | tgt | att | cta | aat | ttg | aat | cca | ctt | ctc | 1349 |
| Gly | Met | Ala | Ser | Ser | Gly | Met | Cys | Ile | Leu | Asn | Leu | Asn | Pro | Leu | Leu | |
| | | | 430 | | | | 435 | | | | 440 | | | | | | ttg ttg gat aaa ctt ctc ccc gac aac att ctg gag caa ata cat tct  1397
Leu Leu Asp Lys Leu Leu Pro Asp Asn Ile Leu Glu Gln Ile His Ser
        445                 450                 455 cca tcc aag atc ctg gac ctc tta gaa ttg acg ggc aga atc gcc gat  1445
Pro Ser Lys Ile Leu Asp Leu Leu Glu Leu Thr Gly Arg Ile Ala Asp
460                 465                 470 gac tta aaa gat ttc gag gac gag aag gaa cgc ggg gag atg gct tca  1493
Asp Leu Lys Asp Phe Glu Asp Glu Lys Glu Arg Gly Glu Met Ala Ser
475                 480                 485                 490 tct tta cag tgt tat atg aaa gaa aat cct gaa tct aca gtg gaa aat  1541
Ser Leu Gln Cys Tyr Met Lys Glu Asn Pro Glu Ser Thr Val Glu Asn
            495                 500                 505 gct tta aat cac ata aaa ggc atc ctt aat cgt tcc ctt gag gaa ttt  1589
Ala Leu Asn His Ile Lys Gly Ile Leu Asn Arg Ser Leu Glu Glu Phe
                510                 515                 520 aat tgg gag ttt atg aag cag gat agt gtc cca atg tgt tgc aag aaa  1637
Asn Trp Glu Phe Met Lys Gln Asp Ser Val Pro Met Cys Cys Lys Lys
            525                 530                 535 ttc act ttc aat ata ggt cga gga ctt caa ttc atc tac aaa tac aga  1685
Phe Thr Phe Asn Ile Gly Arg Gly Leu Gln Phe Ile Tyr Lys Tyr Arg
540                 545                 550 gac ggc tta tac att tct gac aag gaa gta aag gac cag ata ttc aaa  1733
Asp Gly Leu Tyr Ile Ser Asp Lys Glu Val Lys Asp Gln Ile Phe Lys
555                 560                 565                 570 att cta gtc cac caa gtt cca atg gag gaa tagtgatggt cttggttgta    1783
Ile Leu Val His Gln Val Pro Met Glu Glu
                575                 580 gttgtctatt atggtatatt gcattgacat ttatgcttaa aggtgtttct taaacgttta  1843
gggcggaccg ttaaataagt tggcaataat taatatctcg ag                    1885

<210> SEQ ID NO 48
<211> LENGTH: 580
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 48

Met Ala Glu Ile Ser Glu Ser Ile Pro Arg Arg Thr Gly Asn His His
 1               5                   10                  15

Gly Asn Val Trp Asp Asp Asp Leu Ile His Ser Leu Asn Ser Pro Tyr
            20                  25                  30

Gly Ala Pro Ala Tyr Tyr Glu Leu Leu Gln Lys Leu Ile Gln Glu Ile
        35                  40                  45

Lys His Leu Leu Leu Thr Glu Met Glu Met Asp Asp Gly Asp His Asp
    50                  55                  60

Leu Ile Lys Arg Leu Gln Ile Val Asp Thr Leu Glu Cys Leu Gly Ile
65                  70                  75                  80

Asp Arg His Phe Glu His Glu Ile Gln Thr Ala Ala Leu Asp Tyr Val
                85                  90                  95

Tyr Arg Trp Trp Asn Glu Lys Gly Ile Gly Glu Gly Ser Arg Asp Ser
            100                 105                 110

```
Phe Ser Lys Asp Leu Asn Ala Thr Ala Leu Gly Phe Arg Ala Leu Arg
        115                 120                 125
Leu His Arg Tyr Asn Val Ser Ser Gly Val Leu Lys Asn Phe Lys Asp
    130                 135                 140
Glu Asn Gly Lys Phe Phe Cys Asn Phe Thr Gly Glu Gly Arg Gly
145                 150                 155                 160
Asp Lys Gln Val Arg Ser Met Leu Ser Leu Leu Arg Ala Ser Glu Ile
                165                 170                 175
Ser Phe Pro Gly Glu Lys Val Met Glu Glu Ala Lys Ala Phe Thr Arg
            180                 185                 190
Glu Tyr Leu Asn Gln Val Leu Ala Gly His Gly Asp Val Thr Asp Val
        195                 200                 205
Asp Gln Ser Leu Leu Arg Glu Val Lys Tyr Ala Leu Glu Phe Pro Trp
    210                 215                 220
His Cys Ser Val Pro Arg Trp Glu Ala Arg Ser Phe Leu Glu Ile Tyr
225                 230                 235                 240
Gly His Asn His Ser Trp Leu Lys Ser Asn Ile Asn Gln Lys Met Leu
                245                 250                 255
Lys Leu Ala Lys Leu Asp Phe Asn Ile Leu Gln Cys Lys His His Lys
            260                 265                 270
Glu Ile Gln Phe Ile Thr Arg Trp Arg Asp Ser Gly Ile Ser Gln
        275                 280                 285
Leu Asn Phe Tyr Arg Lys Arg His Val Glu Tyr Tyr Ser Trp Val Val
    290                 295                 300
Met Cys Ile Phe Glu Pro Glu Phe Ser Glu Ser Arg Ile Ala Phe Ala
305                 310                 315                 320
Lys Thr Ala Ile Leu Cys Thr Val Leu Asp Asp Leu Tyr Asp Thr His
                325                 330                 335
Ala Thr Leu His Glu Ile Lys Ile Met Thr Glu Gly Val Arg Arg Trp
            340                 345                 350
Asp Leu Ser Leu Thr Asp Asp Leu Pro Asp Tyr Ile Lys Ile Ala Phe
    355                 360                 365
Gln Phe Phe Phe Asn Thr Val Asn Glu Leu Ile Val Glu Ile Val Lys
    370                 375                 380
Arg Gln Gly Arg Asp Met Thr Thr Ile Val Lys Asp Cys Trp Lys Arg
385                 390                 395                 400
Tyr Ile Glu Ser Tyr Leu Gln Glu Ala Glu Trp Ile Ala Thr Gly His
                405                 410                 415
Ile Pro Thr Phe Asn Glu Tyr Ile Lys Asn Gly Met Ala Ser Ser Gly
            420                 425                 430
Met Cys Ile Leu Asn Leu Asn Pro Leu Leu Leu Leu Asp Lys Leu Leu
            435                 440                 445
Pro Asp Asn Ile Leu Glu Gln Ile His Ser Pro Ser Lys Ile Leu Asp
    450                 455                 460
Leu Leu Glu Leu Thr Gly Arg Ile Ala Asp Asp Leu Lys Asp Phe Glu
465                 470                 475                 480
Asp Glu Lys Glu Arg Gly Glu Met Ala Ser Ser Leu Gln Cys Tyr Met
                485                 490                 495
Lys Glu Asn Pro Glu Ser Thr Val Glu Asn Ala Leu Asn His Ile Lys
            500                 505                 510
Gly Ile Leu Asn Arg Ser Leu Glu Glu Phe Asn Trp Glu Phe Met Lys
        515                 520                 525
```

-continued

```
Gln Asp Ser Val Pro Met Cys Cys Lys Lys Phe Thr Phe Asn Ile Gly
    530                 535                 540

Arg Gly Leu Gln Phe Ile Tyr Lys Tyr Arg Asp Gly Leu Tyr Ile Ser
545                 550                 555                 560

Asp Lys Glu Val Lys Asp Gln Ile Phe Lys Ile Leu Val His Gln Val
                565                 570                 575

Pro Met Glu Glu
            580

<210> SEQ ID NO 49
<211> LENGTH: 1785
<212> TYPE: DNA
<213> ORGANISM: Artificial Sequence
<220> FEATURE:
<223> OTHER INFORMATION: Description of Artificial Sequence:
      computer-generated nucleic acid sequence encoding
      gamma humulene synthase
<221> NAME/KEY: CDS
<222> LOCATION: (4)..(1782)

<400> SEQUENCE: 49 tcc atg gct cag att tcc gaa acc gta tca ccc tct acc gat ttg aag        48
    Met Ala Gln Ile Ser Glu Thr Val Ser Pro Ser Thr Asp Leu Lys
      1               5                  10                  15 agc acc gaa tct tcc att acc tct aat cga cat gga aat atg tgg gag        96
Ser Thr Glu Ser Ser Ile Thr Ser Asn Arg His Gly Asn Met Trp Glu
                 20                  25                  30 gac gat cgc ata cag tct ctc aac tca cct tat ggg gca cct gca tat       144
Asp Asp Arg Ile Gln Ser Leu Asn Ser Pro Tyr Gly Ala Pro Ala Tyr
             35                  40                  45 caa gaa cgc agc gaa aag ctt att gaa gag atc aaa ctt tta ttt ttg       192
Gln Glu Arg Ser Glu Lys Leu Ile Glu Glu Ile Lys Leu Leu Phe Leu
         50                  55                  60 agt gac atg gac gat agc tgc aat gat agc gat cgt gat tta atc aaa       240
Ser Asp Met Asp Asp Ser Cys Asn Asp Ser Asp Arg Asp Leu Ile Lys
     65                  70                  75 cgt ctt gag atc gtt gat act gtc gag tgt ctg gga att gat cga cat       288
Arg Leu Glu Ile Val Asp Thr Val Glu Cys Leu Gly Ile Asp Arg His
 80                  85                  90                  95 ttt caa cct gag ata aaa tta gct ctg gat tac gtt tac aga tgt tgg       336
Phe Gln Pro Glu Ile Lys Leu Ala Leu Asp Tyr Val Tyr Arg Cys Trp
                100                 105                 110 aac gaa aga ggc atc gga gag gga tca aga gat tcc ctc aag aaa gat       384
Asn Glu Arg Gly Ile Gly Glu Gly Ser Arg Asp Ser Leu Lys Lys Asp
            115                 120                 125 ctg aac gct aca gct ttg gga ttc cgg gct ctc cga ctc cat cga tat       432
Leu Asn Ala Thr Ala Leu Gly Phe Arg Ala Leu Arg Leu His Arg Tyr
        130                 135                 140 aac gta tcc tca ggt gtc ttg gag aat ttc aga gat gat aac ggg cag       480
Asn Val Ser Ser Gly Val Leu Glu Asn Phe Arg Asp Asp Asn Gly Gln
    145                 150                 155 ttc ttc tgc ggt tct aca gtt gaa gaa gaa gga gca gaa gca tat aat       528
Phe Phe Cys Gly Ser Thr Val Glu Glu Glu Gly Ala Glu Ala Tyr Asn
160                 165                 170                 175 aaa cac gta aga tgc atg ctg tca tta tcg cga gct tca aac att tta       576
Lys His Val Arg Cys Met Leu Ser Leu Ser Arg Ala Ser Asn Ile Leu
                180                 185                 190 ttt ccg ggc gaa aaa gtg atg gaa gag gcg aag gca ttc aca aca aat       624
Phe Pro Gly Glu Lys Val Met Glu Glu Ala Lys Ala Phe Thr Thr Asn
            195                 200                 205 tat cta aag aaa gtt tta gca gga cgg gag gct acc cac gtc gat gaa       672
```

```
Tyr Leu Lys Lys Val Leu Ala Gly Arg Glu Ala Thr His Val Asp Glu
            210                 215                 220 agc ctt ttg gga gag gtg aag tac gca ttg gag ttt cca tgg cat tgc        720
Ser Leu Leu Gly Glu Val Lys Tyr Ala Leu Glu Phe Pro Trp His Cys
225                 230                 235 agt gtg cag aga tgg gag gca agg agc ttt atc gaa ata ttt gga caa        768
Ser Val Gln Arg Trp Glu Ala Arg Ser Phe Ile Glu Ile Phe Gly Gln
240                 245                 250                 255 att gat tca gag ctt aag tcg aat ttg agc aaa aaa atg tta gag ttg        816
Ile Asp Ser Glu Leu Lys Ser Asn Leu Ser Lys Lys Met Leu Glu Leu
                260                 265                 270 gcg aaa ttg gac ttc aat att ctg caa tgc aca cat cag aaa gaa ctg        864
Ala Lys Leu Asp Phe Asn Ile Leu Gln Cys Thr His Gln Lys Glu Leu
                275                 280                 285 cag att atc tca agg tgg ttc gca gac tca agt ata gca tcc ctg aat        912
Gln Ile Ile Ser Arg Trp Phe Ala Asp Ser Ser Ile Ala Ser Leu Asn
            290                 295                 300 ttc tat cgg aaa tgt tac gtc gaa ttt tac ttt tgg atg gct gca gcc        960
Phe Tyr Arg Lys Cys Tyr Val Glu Phe Tyr Phe Trp Met Ala Ala Ala
305                 310                 315 atc tcc gag ccg gag ttt tct gga agc aga gtt gcc ttc aca aaa att       1008
Ile Ser Glu Pro Glu Phe Ser Gly Ser Arg Val Ala Phe Thr Lys Ile
320                 325                 330                 335 gct ata ctg atg aca atg cta gat gac ctg tac gat act cac gga acc       1056
Ala Ile Leu Met Thr Met Leu Asp Asp Leu Tyr Asp Thr His Gly Thr
                340                 345                 350 ttg gac caa ctc aaa atc ttt aca gag gga gtg aga cga tgg gat gtt       1104
Leu Asp Gln Leu Lys Ile Phe Thr Glu Gly Val Arg Arg Trp Asp Val
                355                 360                 365 tcg ttg gta gag ggc ctc cca gac ttc atg aaa att gca ttc gag ttc       1152
Ser Leu Val Glu Gly Leu Pro Asp Phe Met Lys Ile Ala Phe Glu Phe
            370                 375                 380 tgg tta aag aca tct aat gaa ttg att gct gaa gct gtt aaa gcg caa       1200
Trp Leu Lys Thr Ser Asn Glu Leu Ile Ala Glu Ala Val Lys Ala Gln
385                 390                 395 ggg caa gat atg gcg gcc tac ata aga aaa aat gca tgg gag cga tac       1248
Gly Gln Asp Met Ala Ala Tyr Ile Arg Lys Asn Ala Trp Glu Arg Tyr
400                 405                 410                 415 ctt gaa gct tat ctg caa gat gcg gaa tgg ata gcc act gga cat gtc       1296
Leu Glu Ala Tyr Leu Gln Asp Ala Glu Trp Ile Ala Thr Gly His Val
                420                 425                 430 ccc acc ttt gat gag tac ttg aat aat ggc aca cca aac act ggg atg       1344
Pro Thr Phe Asp Glu Tyr Leu Asn Asn Gly Thr Pro Asn Thr Gly Met
                435                 440                 445 tgt gta ttg aat ttg att ccg ctt ctg tta atg ggt gaa cat tta cca       1392
Cys Val Leu Asn Leu Ile Pro Leu Leu Leu Met Gly Glu His Leu Pro
            450                 455                 460 atc gac att ctg gag caa ata ttc ttg ccc tcc agg ttc cac cat ctc       1440
Ile Asp Ile Leu Glu Gln Ile Phe Leu Pro Ser Arg Phe His His Leu
465                 470                 475 att gaa ttg gct tcc agg ctc gtc gat gac gcg aga gat ttc cag gcg       1488
Ile Glu Leu Ala Ser Arg Leu Val Asp Asp Ala Arg Asp Phe Gln Ala
480                 485                 490                 495 gag aag gat cat ggg gat tta tcg tgt att gag tgt tat tta aaa gat       1536
Glu Lys Asp His Gly Asp Leu Ser Cys Ile Glu Cys Tyr Leu Lys Asp
                500                 505                 510 cat cct gag tct aca gta gaa gat gct tta aat cat gtt aat ggc ctc       1584
His Pro Glu Ser Thr Val Glu Asp Ala Leu Asn His Val Asn Gly Leu
            515                 520                 525
```

```
ctt ggc aat tgc ctt ctg gaa atg aat tgg aag ttc tta aag aag cag    1632
Leu Gly Asn Cys Leu Leu Glu Met Asn Trp Lys Phe Leu Lys Lys Gln
        530                 535                 540 gac agt gtg cca ctc tcg tgt aag aag tac agc ttc cat gta ttg gca    1680
Asp Ser Val Pro Leu Ser Cys Lys Lys Tyr Ser Phe His Val Leu Ala
545                 550                 555 cga agc atc caa ttc atg tac aat caa ggc gat ggc ttc tcc att tcg    1728
Arg Ser Ile Gln Phe Met Tyr Asn Gln Gly Asp Gly Phe Ser Ile Ser
560                 565                 570                 575 aac aaa gtg atc aag gat caa gtg cag aaa gtt ctt att gtc ccc gtg    1776
Asn Lys Val Ile Lys Asp Gln Val Gln Lys Val Leu Ile Val Pro Val
                580                 585                 590 cct att tga                                                        1785
Pro Ile

<210> SEQ ID NO 50
<211> LENGTH: 593
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 50

Met Ala Gln Ile Ser Glu Thr Val Ser Pro Ser Thr Asp Leu Lys Ser
 1               5                  10                  15

Thr Glu Ser Ser Ile Thr Ser Asn Arg His Gly Asn Met Trp Glu Asp
                20                  25                  30

Asp Arg Ile Gln Ser Leu Asn Ser Pro Tyr Gly Ala Pro Ala Tyr Gln
            35                  40                  45

Glu Arg Ser Glu Lys Leu Ile Glu Ile Lys Leu Leu Phe Leu Ser
        50                  55                  60

Asp Met Asp Asp Ser Cys Asn Asp Ser Asp Arg Asp Leu Ile Lys Arg
 65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
```

```
                        245                 250                 255
Asp Ser Glu Leu Lys Ser Asn Leu Ser Lys Met Leu Glu Leu Ala
                260                 265                 270

Lys Leu Asp Phe Asn Ile Leu Gln Cys Thr His Gln Lys Glu Leu Gln
                275                 280                 285

Ile Ile Ser Arg Trp Phe Ala Asp Ser Ser Ile Ala Ser Leu Asn Phe
                290                 295                 300

Tyr Arg Lys Cys Tyr Val Glu Phe Tyr Phe Trp Met Ala Ala Ile
305                 310                 315                 320

Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
                340                 345                 350

Asp Gln Leu Lys Ile Phe Thr Glu Gly Val Arg Arg Trp Asp Val Ser
                355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
                420                 425                 430

Thr Phe Asp Glu Tyr Leu Asn Asn Gly Thr Pro Asn Thr Gly Met Cys
                435                 440                 445

Val Leu Asn Leu Ile Pro Leu Leu Leu Met Gly Glu His Leu Pro Ile
    450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
                500                 505                 510

Pro Glu Ser Thr Val Glu Asp Ala Leu Asn His Val Asn Gly Leu Leu
                515                 520                 525

Gly Asn Cys Leu Leu Glu Met Asn Trp Lys Phe Leu Lys Lys Gln Asp
                530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Ile
```

```
<210> SEQ ID NO 51
<211> LENGTH: 1785
<212> TYPE: DNA
<213> ORGANISM: Artificial Sequence
<220> FEATURE:
<223> OTHER INFORMATION: Description of Artificial Sequence:
      computer-generated nucleic acid sequence encoding
      gamma humulene synthase
<221> NAME/KEY: CDS
<222> LOCATION: (4)..(1782)
```

```
<400> SEQUENCE: 51 tct atg gct cag att tct gaa tct gta tca ccc tct acc gat ttg aag      48
    Met Ala Gln Ile Ser Glu Ser Val Ser Pro Ser Thr Asp Leu Lys
    1               5                   10                  15 agc acc gaa tct tcc att acc tct aat cga cat gga aat atg tgg gag      96
Ser Thr Glu Ser Ser Ile Thr Ser Asn Arg His Gly Asn Met Trp Glu
                20                  25                  30 gac gat cgc ata cag tct ctc aac tca cct tat ggg gca cct gca tat     144
Asp Asp Arg Ile Gln Ser Leu Asn Ser Pro Tyr Gly Ala Pro Ala Tyr
                35                  40                  45 caa gaa cgc agc gaa aag ctt att gaa gag atc aaa ctt tta ttt ttg     192
Gln Glu Arg Ser Glu Lys Leu Ile Glu Glu Ile Lys Leu Leu Phe Leu
            50                  55                  60 agt gac atg gac gat agc tgc aat gat agc gat cgt gat tta atc aaa     240
Ser Asp Met Asp Asp Ser Cys Asn Asp Ser Asp Arg Asp Leu Ile Lys
65                  70                  75 cgt ctt gag atc gtt gat act gtc gag tgt ctg gga att gat cga cat     288
Arg Leu Glu Ile Val Asp Thr Val Glu Cys Leu Gly Ile Asp Arg His
80                  85                  90                  95 ttt caa cct gag ata aaa tta gct ctg gat tac gtt tac aga tgt tgg     336
Phe Gln Pro Glu Ile Lys Leu Ala Leu Asp Tyr Val Tyr Arg Cys Trp
                100                 105                 110 aac gaa aga ggc atc gga gag gga tca aga gat tcc ctc aag aaa gat     384
Asn Glu Arg Gly Ile Gly Glu Gly Ser Arg Asp Ser Leu Lys Lys Asp
            115                 120                 125 ctg aac gct aca gct ttg gga ttc cgg gct ctc cga ctc cat cga tat     432
Leu Asn Ala Thr Ala Leu Gly Phe Arg Ala Leu Arg Leu His Arg Tyr
        130                 135                 140 aac gta tcc tca ggt gtc ttg gag aat ttc aga gat gat aac ggg cag     480
Asn Val Ser Ser Gly Val Leu Glu Asn Phe Arg Asp Asp Asn Gly Gln
145                 150                 155 ttc ttc tgc ggt tct aca gtt gaa gaa gaa gga gca gaa gca tat aat     528
Phe Phe Cys Gly Ser Thr Val Glu Glu Glu Gly Ala Glu Ala Tyr Asn
160                 165                 170                 175 aaa cac gta aga tgc atg ctg tca tta tcg cga gct tca aac att tta     576
Lys His Val Arg Cys Met Leu Ser Leu Ser Arg Ala Ser Asn Ile Leu
                180                 185                 190 ttt ccg ggc gaa aaa gtg atg gaa gag gcg aag gca ttc aca aca aat     624
Phe Pro Gly Glu Lys Val Met Glu Glu Ala Lys Ala Phe Thr Thr Asn
            195                 200                 205 tat cta aag aaa gtt tta gca gga cgg gag gct acc cac gtc gat gaa     672
Tyr Leu Lys Lys Val Leu Ala Gly Arg Glu Ala Thr His Val Asp Glu
        210                 215                 220 agc ctt ttg gga gag gtg aag tac gca ttg gag ttt cca tgg cat tgc     720
Ser Leu Leu Gly Glu Val Lys Tyr Ala Leu Glu Phe Pro Trp His Cys
225                 230                 235 agt gtg cag aga tgg gag gca agg agc ttt atc gaa ata ttt gga caa     768
Ser Val Gln Arg Trp Glu Ala Arg Ser Phe Ile Glu Ile Phe Gly Gln
240                 245                 250                 255 att gat tca gag ctt aag tcg aat ttg agc aaa aaa atg tta gag ttg     816
Ile Asp Ser Glu Leu Lys Ser Asn Leu Ser Lys Lys Met Leu Glu Leu
                260                 265                 270 gcg aaa ttg gac ttc aat att ctg caa tgc aca cat cag aaa gaa ctg     864
Ala Lys Leu Asp Phe Asn Ile Leu Gln Cys Thr His Gln Lys Glu Leu
            275                 280                 285 cag att atc tca agg tgg ttc gca gac tca agt ata gca tcc ctg aat     912
Gln Ile Ile Ser Arg Trp Phe Ala Asp Ser Ser Ile Ala Ser Leu Asn
        290                 295                 300 ttc tat cgg aaa tgt tac gtc gaa ttt tac ttt tgg atg gct gca gcc     960
```

```
Phe Tyr Arg Lys Cys Tyr Val Glu Phe Tyr Phe Trp Met Ala Ala Ala
    305                 310                 315 atc tcc gag ccg gag ttt tct gga agc aga gtt gcc ttc aca aaa att       1008
Ile Ser Glu Pro Glu Phe Ser Gly Ser Arg Val Ala Phe Thr Lys Ile
320                 325                 330                 335 gct ata ctg atg aca atg cta gat gac ctg tac gat act cac gga acc       1056
Ala Ile Leu Met Thr Met Leu Asp Asp Leu Tyr Asp Thr His Gly Thr
                340                 345                 350 ttg gac caa ctc aaa atc ttt aca gag gga gtg aga cga tgg gat gtt       1104
Leu Asp Gln Leu Lys Ile Phe Thr Glu Gly Val Arg Arg Trp Asp Val
        355                 360                 365 tcg ttg gta gag ggc ctc cca gac ttc atg aaa att gca ttc gag ttc       1152
Ser Leu Val Glu Gly Leu Pro Asp Phe Met Lys Ile Ala Phe Glu Phe
    370                 375                 380 tgg tta aag aca tct aat gaa ttg att gct gaa gct gtt aaa gcg caa       1200
Trp Leu Lys Thr Ser Asn Glu Leu Ile Ala Glu Ala Val Lys Ala Gln
385                 390                 395 ggg caa gat atg gcg gcc tac ata aga aaa aat gca tgg gag cga tac       1248
Gly Gln Asp Met Ala Ala Tyr Ile Arg Lys Asn Ala Trp Glu Arg Tyr
400                 405                 410                 415 ctt gaa gct tat ctg caa gat gcg gaa tgg ata gcc act gga cat gtc       1296
Leu Glu Ala Tyr Leu Gln Asp Ala Glu Trp Ile Ala Thr Gly His Val
                420                 425                 430 ccc acc ttt gat gag tac ttg aat aat ggc aca cca aac act ggg atg       1344
Pro Thr Phe Asp Glu Tyr Leu Asn Asn Gly Thr Pro Asn Thr Gly Met
        435                 440                 445 tgt gta ttg aat ttg att ccg ctt ctg tta atg ggt gaa cat tta cca       1392
Cys Val Leu Asn Leu Ile Pro Leu Leu Leu Met Gly Glu His Leu Pro
    450                 455                 460 atc gac att ctg gag caa ata ttc ttg ccc tcc agg ttc cac cat ctc       1440
Ile Asp Ile Leu Glu Gln Ile Phe Leu Pro Ser Arg Phe His His Leu
465                 470                 475 att gaa ttg gct tcc agg ctc gtc gat gac gcg aga gat ttc cag gcg       1488
Ile Glu Leu Ala Ser Arg Leu Val Asp Asp Ala Arg Asp Phe Gln Ala
480                 485                 490                 495 gag aag gat cat ggg gat tta tcg tgt att gag tgt tat tta aaa gat       1536
Glu Lys Asp His Gly Asp Leu Ser Cys Ile Glu Cys Tyr Leu Lys Asp
                500                 505                 510 cat cct gag tct aca gta gaa gat gct tta aat cat gtt aat ggc ctc       1584
His Pro Glu Ser Thr Val Glu Asp Ala Leu Asn His Val Asn Gly Leu
        515                 520                 525 ctt ggc aat tgc ctt ctg gaa atg aat tgg aag ttc tta aag aag cag       1632
Leu Gly Asn Cys Leu Leu Glu Met Asn Trp Lys Phe Leu Lys Lys Gln
    530                 535                 540 gac agt gtg cca ctc tcg tgt aag aag tac agc ttc cat gta ttg gca       1680
Asp Ser Val Pro Leu Ser Cys Lys Lys Tyr Ser Phe His Val Leu Ala
545                 550                 555 cga agc atc caa ttc atg tac aat caa ggc gat ggc ttc tcc att tcg       1728
Arg Ser Ile Gln Phe Met Tyr Asn Gln Gly Asp Gly Phe Ser Ile Ser
560                 565                 570                 575 aac aaa gtg atc aag gat caa gtg cag aaa gtt ctt att gtc ccc gtg       1776
Asn Lys Val Ile Lys Asp Gln Val Gln Lys Val Leu Ile Val Pro Val
                580                 585                 590 cct gtt tga                                                            1785
Pro Val <210> SEQ ID NO 52
<211> LENGTH: 593
<212> TYPE: PRT
<213> ORGANISM: Artificial Sequence
```

```
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 52
```

| | | | | | | | | | | | | | | |
|---|---|---|---|---|---|---|---|---|---|---|---|---|---|---|
| Met | Ala | Gln | Ile | Ser | Glu | Ser | Val | Ser | Pro | Ser | Thr | Asp | Leu | Lys | Ser |
| 1 | | | | 5 | | | | | 10 | | | | | 15 | |
| Thr | Glu | Ser | Ser | Ile | Thr | Ser | Asn | Arg | His | Gly | Asn | Met | Trp | Glu | Asp |
| | | | 20 | | | | | 25 | | | | | 30 | | |
| Asp | Arg | Ile | Gln | Ser | Leu | Asn | Ser | Pro | Tyr | Gly | Ala | Pro | Ala | Tyr | Gln |
| | | 35 | | | | | 40 | | | | | 45 | | | |
| Glu | Arg | Ser | Glu | Lys | Leu | Ile | Glu | Glu | Ile | Lys | Leu | Leu | Phe | Leu | Ser |
| | 50 | | | | | 55 | | | | | 60 | | | | |
| Asp | Met | Asp | Asp | Ser | Cys | Asn | Asp | Ser | Asp | Arg | Asp | Leu | Ile | Lys | Arg |
| 65 | | | | | 70 | | | | | 75 | | | | | 80 |
| Leu | Glu | Ile | Val | Asp | Thr | Val | Glu | Cys | Leu | Gly | Ile | Asp | Arg | His | Phe |
| | | | | 85 | | | | | 90 | | | | | 95 | |
| Gln | Pro | Glu | Ile | Lys | Leu | Ala | Leu | Asp | Tyr | Val | Tyr | Arg | Cys | Trp | Asn |
| | | | 100 | | | | | 105 | | | | | 110 | | |
| Glu | Arg | Gly | Ile | Gly | Glu | Gly | Ser | Arg | Asp | Ser | Leu | Lys | Lys | Asp | Leu |
| | | 115 | | | | | 120 | | | | | 125 | | | |
| Asn | Ala | Thr | Ala | Leu | Gly | Phe | Arg | Ala | Leu | Arg | Leu | His | Arg | Tyr | Asn |
| | 130 | | | | | 135 | | | | | 140 | | | | |
| Val | Ser | Ser | Gly | Val | Leu | Glu | Asn | Phe | Arg | Asp | Asp | Asn | Gly | Gln | Phe |
| 145 | | | | | 150 | | | | | 155 | | | | | 160 |
| Phe | Cys | Gly | Ser | Thr | Val | Glu | Glu | Glu | Gly | Ala | Glu | Ala | Tyr | Asn | Lys |
| | | | | 165 | | | | | 170 | | | | | 175 | |
| His | Val | Arg | Cys | Met | Leu | Ser | Leu | Ser | Arg | Ala | Ser | Asn | Ile | Leu | Phe |
| | | | 180 | | | | | 185 | | | | | 190 | | |
| Pro | Gly | Glu | Lys | Val | Met | Glu | Glu | Ala | Lys | Ala | Phe | Thr | Thr | Asn | Tyr |
| | | 195 | | | | | 200 | | | | | 205 | | | |
| Leu | Lys | Lys | Val | Leu | Ala | Gly | Arg | Glu | Ala | Thr | His | Val | Asp | Glu | Ser |
| | 210 | | | | | 215 | | | | | 220 | | | | |
| Leu | Leu | Gly | Glu | Val | Lys | Tyr | Ala | Leu | Glu | Phe | Pro | Trp | His | Cys | Ser |
| 225 | | | | | 230 | | | | | 235 | | | | | 240 |
| Val | Gln | Arg | Trp | Glu | Ala | Arg | Ser | Phe | Ile | Glu | Ile | Phe | Gly | Gln | Ile |
| | | | | 245 | | | | | 250 | | | | | 255 | |
| Asp | Ser | Glu | Leu | Lys | Ser | Asn | Leu | Ser | Lys | Met | Leu | Glu | Leu | Ala |
| | | | 260 | | | | | 265 | | | | | 270 | | |
| Lys | Leu | Asp | Phe | Asn | Ile | Leu | Gln | Cys | Thr | His | Gln | Lys | Glu | Leu | Gln |
| | | 275 | | | | | 280 | | | | | 285 | | | |
| Ile | Ile | Ser | Arg | Trp | Phe | Ala | Asp | Ser | Ser | Ile | Ala | Ser | Leu | Asn | Phe |
| | 290 | | | | | 295 | | | | | 300 | | | | |
| Tyr | Arg | Lys | Cys | Tyr | Val | Glu | Phe | Tyr | Phe | Trp | Met | Ala | Ala | Ala | Ile |
| 305 | | | | | 310 | | | | | 315 | | | | | 320 |
| Ser | Glu | Pro | Glu | Phe | Ser | Gly | Ser | Arg | Val | Ala | Phe | Thr | Lys | Ile | Ala |
| | | | | 325 | | | | | 330 | | | | | 335 | |
| Ile | Leu | Met | Thr | Met | Leu | Asp | Asp | Leu | Tyr | Asp | Thr | His | Gly | Thr | Leu |
| | | | 340 | | | | | 345 | | | | | 350 | | |
| Asp | Gln | Leu | Lys | Ile | Phe | Thr | Glu | Gly | Val | Arg | Arg | Trp | Asp | Val | Ser |
| | | 355 | | | | | 360 | | | | | 365 | | | |
| Leu | Val | Glu | Gly | Leu | Pro | Asp | Phe | Met | Lys | Ile | Ala | Phe | Glu | Phe | Trp |

-continued

```
              370                 375                 380
Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
                420                 425                 430

Thr Phe Asp Glu Tyr Leu Asn Asn Gly Thr Pro Asn Thr Gly Met Cys
                435                 440                 445

Val Leu Asn Leu Ile Pro Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
                500                 505                 510

Pro Glu Ser Thr Val Asp Ala Leu Asn His Val Asn Gly Leu Leu
                515                 520                 525

Gly Asn Cys Leu Leu Glu Met Asn Trp Lys Phe Leu Lys Lys Gln Asp
530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Val
```

<210> SEQ ID NO 53
<211> LENGTH: 1785
<212> TYPE: DNA
<213> ORGANISM: Artificial Sequence
<220> FEATURE:
<223> OTHER INFORMATION: Description of Artificial Sequence:
      computer-generated nucleic acid sequence encoding
      gamma humulene synthase
<221> NAME/KEY: CDS
<222> LOCATION: (4)..(1782)

<400> SEQUENCE: 53

```
tcc atg gct cag att tct gaa tct gta tca ccc tct acc gat ttg aag      48
    Met Ala Gln Ile Ser Glu Ser Val Ser Pro Ser Thr Asp Leu Lys
    1               5                   10                  15 agc acc gaa tct tcc att acc tct aat cga cat gga aat atg tgg gag      96
Ser Thr Glu Ser Ser Ile Thr Ser Asn Arg His Gly Asn Met Trp Glu
                20                  25                  30 gac gat cgc ata cag tct ctc aac tca cct tat ggg gca cct gca tat     144
Asp Asp Arg Ile Gln Ser Leu Asn Ser Pro Tyr Gly Ala Pro Ala Tyr
            35                  40                  45 caa gaa cgc agc gaa aag ctt att gaa gag atc aaa ctt tta ttt ttg     192
Gln Glu Arg Ser Glu Lys Leu Ile Glu Glu Ile Lys Leu Leu Phe Leu
        50                  55                  60 agt gac atg gac gat agc tgc aat gat agc gat cgt gat tta atc aaa     240
Ser Asp Met Asp Asp Ser Cys Asn Asp Ser Asp Arg Asp Leu Ile Lys
65                  70                  75 cgt ctt gag atc gtt gat act gtc gag tgt ctg gga att gat cga cat     288
Arg Leu Glu Ile Val Asp Thr Val Glu Cys Leu Gly Ile Asp Arg His
```

-continued

| | | | | | | | | | | | | | | | | |
|---|---|---|---|---|---|---|---|---|---|---|---|---|---|---|---|---|
| | 80 | | | | 85 | | | | 90 | | | | 95 | | | |
| ttt | caa | cct | gag | ata | aaa | tta | gct | ctg | gat | tac | gtt | tac | aga | tgt | tgg | 336 |
| Phe | Gln | Pro | Glu | Ile | Lys | Leu | Ala | Leu | Asp | Tyr | Val | Tyr | Arg | Cys | Trp | |
| | | | | 100 | | | | | 105 | | | | | 110 | | |
| aac | gaa | aga | ggc | atc | gga | gag | gga | tca | aga | gat | tcc | ctc | aag | aaa | gat | 384 |
| Asn | Glu | Arg | Gly | Ile | Gly | Glu | Gly | Ser | Arg | Asp | Ser | Leu | Lys | Lys | Asp | |
| | | | | 115 | | | | | 120 | | | | | 125 | | |
| ctg | aac | gct | aca | gct | ttg | gga | ttc | cgg | gct | ctc | cga | ctc | cat | cga | tat | 432 |
| Leu | Asn | Ala | Thr | Ala | Leu | Gly | Phe | Arg | Ala | Leu | Arg | Leu | His | Arg | Tyr | |
| | | | 130 | | | | | 135 | | | | | 140 | | | |
| aac | gta | tcc | tca | ggt | gtc | ttg | gag | aat | ttc | aga | gat | gat | aac | ggg | cag | 480 |
| Asn | Val | Ser | Ser | Gly | Val | Leu | Glu | Asn | Phe | Arg | Asp | Asp | Asn | Gly | Gln | |
| | | 145 | | | | | 150 | | | | | 155 | | | | |
| ttc | ttc | tgc | ggt | tct | aca | gtt | gaa | gaa | gaa | gga | gca | gaa | gca | tat | aat | 528 |
| Phe | Phe | Cys | Gly | Ser | Thr | Val | Glu | Glu | Glu | Gly | Ala | Glu | Ala | Tyr | Asn | |
| 160 | | | | | 165 | | | | | 170 | | | | | 175 | |
| aaa | cac | gta | aga | tgc | atg | ctg | tca | tta | tcg | cga | gct | tca | aac | att | tta | 576 |
| Lys | His | Val | Arg | Cys | Met | Leu | Ser | Leu | Ser | Arg | Ala | Ser | Asn | Ile | Leu | |
| | | | | 180 | | | | | 185 | | | | | 190 | | |
| ttt | ccg | ggc | gaa | aaa | gtg | atg | gaa | gag | gcg | aag | gca | ttc | aca | aca | aat | 624 |
| Phe | Pro | Gly | Glu | Lys | Val | Met | Glu | Glu | Ala | Lys | Ala | Phe | Thr | Thr | Asn | |
| | | | | 195 | | | | | 200 | | | | | 205 | | |
| tat | cta | aag | aaa | gtt | tta | gca | gga | cgg | gag | gct | acc | cac | gtc | gat | gaa | 672 |
| Tyr | Leu | Lys | Lys | Val | Leu | Ala | Gly | Arg | Glu | Ala | Thr | His | Val | Asp | Glu | |
| | | 210 | | | | | 215 | | | | | 220 | | | | |
| agc | ctt | ttg | gga | gag | gtg | aag | tac | gca | ttg | gag | ttt | cca | tgg | cat | tgc | 720 |
| Ser | Leu | Leu | Gly | Glu | Val | Lys | Tyr | Ala | Leu | Glu | Phe | Pro | Trp | His | Cys | |
| | 225 | | | | | 230 | | | | | 235 | | | | | |
| agt | gtg | cag | aga | tgg | gag | gca | agg | agc | ttt | atc | gaa | ata | ttt | gga | caa | 768 |
| Ser | Val | Gln | Arg | Trp | Glu | Ala | Arg | Ser | Phe | Ile | Glu | Ile | Phe | Gly | Gln | |
| 240 | | | | | 245 | | | | | 250 | | | | | 255 | |
| att | gat | tca | gag | ctt | aag | tcg | aat | ttg | agc | aaa | aaa | atg | tta | gag | ttg | 816 |
| Ile | Asp | Ser | Glu | Leu | Lys | Ser | Asn | Leu | Ser | Lys | Lys | Met | Leu | Glu | Leu | |
| | | | | 260 | | | | | 265 | | | | | 270 | | |
| gcg | aaa | ttg | gac | ttc | aat | att | ctg | caa | tgc | aca | cat | cag | aaa | gaa | ctg | 864 |
| Ala | Lys | Leu | Asp | Phe | Asn | Ile | Leu | Gln | Cys | Thr | His | Gln | Lys | Glu | Leu | |
| | | | 275 | | | | | 280 | | | | | 285 | | | |
| cag | att | atc | tca | agg | tgg | ttc | gca | gac | tca | agt | ata | gca | tcc | ctg | aat | 912 |
| Gln | Ile | Ile | Ser | Arg | Trp | Phe | Ala | Asp | Ser | Ser | Ile | Ala | Ser | Leu | Asn | |
| | | 290 | | | | | 295 | | | | | 300 | | | | |
| ttc | tat | cgg | aaa | tgt | tac | gtc | gaa | ttt | tac | ttt | tgg | atg | gct | gca | gcc | 960 |
| Phe | Tyr | Arg | Lys | Cys | Tyr | Val | Glu | Phe | Tyr | Phe | Trp | Met | Ala | Ala | Ala | |
| | 305 | | | | | 310 | | | | | 315 | | | | | |
| atc | tcc | gag | ccg | gag | ttt | tct | gga | agc | aga | gtt | gcc | ttc | aca | aaa | att | 1008 |
| Ile | Ser | Glu | Pro | Glu | Phe | Ser | Gly | Ser | Arg | Val | Ala | Phe | Thr | Lys | Ile | |
| 320 | | | | | 325 | | | | | 330 | | | | | 335 | |
| gct | ata | ctg | atg | aca | atg | cta | gat | gac | ctg | tac | gat | act | cac | gga | acc | 1056 |
| Ala | Ile | Leu | Met | Thr | Met | Leu | Asp | Asp | Leu | Tyr | Asp | Thr | His | Gly | Thr | |
| | | | | 340 | | | | | 345 | | | | | 350 | | |
| ttg | gac | caa | ctc | aaa | atc | ttt | aca | gag | gga | gtg | aga | cga | tgg | gat | gtt | 1104 |
| Leu | Asp | Gln | Leu | Lys | Ile | Phe | Thr | Glu | Gly | Val | Arg | Arg | Trp | Asp | Val | |
| | | | 355 | | | | | 360 | | | | | 365 | | | |
| tcg | ttg | gta | gag | ggc | ctc | cca | gac | ttc | atg | aaa | att | gca | ttc | gag | ttc | 1152 |
| Ser | Leu | Val | Glu | Gly | Leu | Pro | Asp | Phe | Met | Lys | Ile | Ala | Phe | Glu | Phe | |
| | | 370 | | | | | 375 | | | | | 380 | | | | |
| tgg | tta | aag | aca | tct | aat | gaa | ttg | att | gct | gaa | gct | gtt | aaa | gcg | caa | 1200 |
| Trp | Leu | Lys | Thr | Ser | Asn | Glu | Leu | Ile | Ala | Glu | Ala | Val | Lys | Ala | Gln | |
| | 385 | | | | | 390 | | | | | 395 | | | | | |
| ggg | caa | gat | atg | gcg | gtt | tac | ata | aga | aaa | aat | gca | tgg | gag | cga | tac | 1248 |

```
Gly Gln Asp Met Ala Val Tyr Ile Arg Lys Asn Ala Trp Glu Arg Tyr
400                 405                 410                 415 ctt gaa gct tat ctg caa gat gcg gaa tgg ata gcc act gga cat gtc    1296
Leu Glu Ala Tyr Leu Gln Asp Ala Glu Trp Ile Ala Thr Gly His Val
                420                 425                 430 ccc acc ttt gat gag tac ttg aat aat ggc aca cca aac act ggg atg    1344
Pro Thr Phe Asp Glu Tyr Leu Asn Asn Gly Thr Pro Asn Thr Gly Met
                435                 440                 445 tgt gta ttg aat ttg att ccg ctt ctg tta atg ggt gaa cat tta cca    1392
Cys Val Leu Asn Leu Ile Pro Leu Leu Leu Met Gly Glu His Leu Pro
            450                 455                 460 atc gac att ctg gag caa ata ttc ttg ccc tcc agg ttc cac cat ctc    1440
Ile Asp Ile Leu Glu Gln Ile Phe Leu Pro Ser Arg Phe His His Leu
465                 470                 475 att gaa ttg gct tcc agg ctc gtc gat gac gcg aga gat ttc cag gcg    1488
Ile Glu Leu Ala Ser Arg Leu Val Asp Asp Ala Arg Asp Phe Gln Ala
480                 485                 490                 495 gag aag gat cat ggg gat tta tcg tgt att gag tgt tat tta aaa gat    1536
Glu Lys Asp His Gly Asp Leu Ser Cys Ile Glu Cys Tyr Leu Lys Asp
                500                 505                 510 cat cct gag tct aca gta gaa gat gct tta aat cat gtt aat ggc ctc    1584
His Pro Glu Ser Thr Val Glu Asp Ala Leu Asn His Val Asn Gly Leu
                515                 520                 525 ctt ggc aat tgc ctt ctg gaa atg aat tgg aag ttc tta aag aag cag    1632
Leu Gly Asn Cys Leu Leu Glu Met Asn Trp Lys Phe Leu Lys Lys Gln
            530                 535                 540 gac agt gtg cca ctc tcg tgt aag aag tac agc ttc cat gta ttg gca    1680
Asp Ser Val Pro Leu Ser Cys Lys Lys Tyr Ser Phe His Val Leu Ala
545                 550                 555 cga agc atc caa ttc atg tac aat caa ggc gat ggc ttc tcc att tcg    1728
Arg Ser Ile Gln Phe Met Tyr Asn Gln Gly Asp Gly Phe Ser Ile Ser
560                 565                 570                 575 aac aaa gtg atc aag gat caa gtg cag aaa gtt ctt att gtc ccc gtg    1776
Asn Lys Val Ile Lys Asp Gln Val Gln Lys Val Leu Ile Val Pro Val
                580                 585                 590 cct att tga                                                         1785
Pro Ile <210> SEQ ID NO 54
<211> LENGTH: 593
<212> TYPE: PRT
<213> ORGANISM: Artificial Sequence
<220> FEATURE:
<223> OTHER INFORMATION: Description of Artificial Sequence:
      protein
<221> NAME/KEY: misc_feature
<222> LOCATION: (1)..(817)
<223> OTHER INFORMATION: Computer-generated protein sequence

<400> SEQUENCE: 54

Met Ala Gln Ile Ser Glu Ser Val Ser Pro Ser Thr Asp Leu Lys Ser
1               5                   10                  15

Thr Glu Ser Ser Ile Thr Ser Asn Arg His Gly Asn Met Trp Glu Asp
                20                  25                  30

Asp Arg Ile Gln Ser Leu Asn Ser Pro Tyr Gly Ala Pro Ala Tyr Gln
            35                  40                  45

Glu Arg Ser Glu Lys Leu Ile Glu Ile Lys Leu Leu Phe Leu Ser
        50                  55                  60

Asp Met Asp Asp Ser Cys Asn Ser Asp Arg Asp Leu Ile Lys Arg
65                  70                  75                  80
```

-continued

```
Leu Glu Ile Val Asp Thr Val Glu Cys Leu Gly Ile Asp Arg His Phe
                 85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
            115                 120                 125

Asn Ala Thr Ala Leu Gly Phe Arg Ala Leu Arg Leu His Arg Tyr Asn
130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Ala Lys Ala Phe Thr Thr Asn Tyr
            195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
    275                 280                 285

Ile Ile Ser Arg Trp Phe Ala Asp Ser Ser Ile Ala Ser Leu Asn Phe
    290                 295                 300

Tyr Arg Lys Cys Tyr Val Glu Phe Tyr Phe Trp Met Ala Ala Ile
305                 310                 315                 320

Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
            355                 360                 365

Leu Val Glu Gly Leu Pro Asp Phe Met Lys Ile Ala Phe Glu Phe Trp
    370                 375                 380

Leu Lys Thr Ser Asn Glu Leu Ile Ala Glu Ala Val Lys Ala Gln Gly
385                 390                 395                 400

Gln Asp Met Ala Val Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Met Cys
            435                 440                 445

Val Leu Asn Leu Ile Pro Leu Leu Met Gly Glu His Leu Pro Ile
    450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
```

```
                          500                 505                 510
Pro Glu Ser Thr Val Glu Asp Ala Leu Asn His Val Asn Gly Leu Leu
            515                 520                 525

Gly Asn Cys Leu Leu Glu Met Asn Trp Lys Phe Leu Lys Lys Gln Asp
        530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Ile

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: amino
      acid sequence motif
<221> NAME/KEY: DOMAIN
<222> LOCATION: (1)..(7)
<223> OTHER INFORMATION: conserved amino acid sequence motif wherein
      Xaa at positions 1, 2, 5 and 6 each represent any amino acid

<400> SEQUENCE: 55

Xaa Xaa Asp Asp Xaa Xaa Asp
  1               5
```